(12) United States Patent
Hu et al.

(10) Patent No.: US 7,439,333 B2
(45) Date of Patent: Oct. 21, 2008

(54) VASCULAR ENDOTHELIAL GROWTH FACTOR 2

(75) Inventors: Jing-Shan Hu, Mountain View, CA (US); Craig A. Rosen, Laytonsville, MD (US); Liang Cao, Bethesda, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 130 days.

(21) Appl. No.: 11/067,015

(22) Filed: Feb. 28, 2005

(65) Prior Publication Data

US 2005/0176103 A1 Aug. 11, 2005

Related U.S. Application Data

(60) Division of application No. 09/935,726, filed on Aug. 24, 2001, now Pat. No. 7,153,942, which is a continuation of application No. 09/438,538, filed on Nov. 12, 1999, now abandoned, which is a division of application No. 09/042,105, filed on Mar. 13, 1998, now Pat. No. 6,040,157, which is a continuation-in-part of application No. 08/999,811, filed on Dec. 24, 1997, now Pat. No. 5,932,540, which is a continuation-in-part of application No. 08/465,968, filed on Jun. 6, 1995, now Pat. No. 6,608,182, and a continuation-in-part of application No. 08/207,550, filed on Mar. 8, 1994, now abandoned, said application No. 08/465,968 is a continuation-in-part of application No. 08/207,550.

(51) Int. Cl.
| C07K 1/00 | (2006.01) |
| C07K 14/00 | (2006.01) |
| C07K 16/00 | (2006.01) |
| C07K 17/00 | (2006.01) |
| C07K 2/00 | (2006.01) |
| C07K 4/00 | (2006.01) |
| C07K 5/00 | (2006.01) |
| A61K 38/24 | (2006.01) |
| A61K 38/27 | (2006.01) |

(52) U.S. Cl. .................. 530/399; 530/300; 530/350
(58) Field of Classification Search ....................... None
See application file for complete search history.

(56) References Cited

U.S. PATENT DOCUMENTS

| 5,073,492 A | 12/1991 | Chen et al. |
| 5,194,596 A | 3/1993 | Tischer et al. |
| 5,219,739 A | 6/1993 | Tischer et al. |
| 5,234,908 A | 8/1993 | Szabo et al. |
| 5,240,848 A | 8/1993 | Keck et al. |
| 5,283,354 A | 2/1994 | Lemischka |
| 5,326,695 A | 7/1994 | Andersson et al. |
| 5,607,918 A | 3/1997 | Eriksson et al. |
| 5,633,147 A | 5/1997 | Meissner et al. |
| 5,652,225 A | 7/1997 | Isner |
| 5,661,133 A | 8/1997 | Leiden et al. |
| 5,693,622 A | 12/1997 | Wolff et al. |
| 5,776,755 A * | 7/1998 | Alitalo et al. ............... 435/194 |
| 5,792,453 A | 8/1998 | Hammond et al. |
| 5,840,693 A | 11/1998 | Eriksson et al. |
| 5,861,301 A | 1/1999 | Terman et al. |
| 5,932,540 A | 8/1999 | Hu et al. |
| 5,935,820 A | 8/1999 | Hu et al. |
| 6,040,157 A | 3/2000 | Hu et al. |
| 6,121,246 A | 9/2000 | Isner |
| 6,130,071 A | 10/2000 | Alitalo et al. |
| 6,221,839 B1 * | 4/2001 | Alitalo et al. .................. 514/12 |
| 6,245,530 B1 * | 6/2001 | Alitalo et al. ............... 435/69.4 |
| 6,361,946 B1 | 3/2002 | Alitalo et al. |
| 6,403,088 B1 * | 6/2002 | Alitalo et al. ............. 424/139.1 |
| 6,451,764 B1 | 9/2002 | Lee et al. |
| 6,608,182 B1 | 8/2003 | Rosen et al. |
| 6,645,933 B1 * | 11/2003 | Alitalo et al. .................. 514/2 |
| 6,734,285 B2 | 5/2004 | Hu et al. |
| 7,109,308 B1 | 9/2006 | Rosen et al. |
| 7,115,392 B2 | 10/2006 | Rosen et al. |
| 7,153,827 B1 | 12/2006 | Hu et al. |
| 7,153,942 B2 | 12/2006 | Hu et al. |
| 7,186,688 B1 | 3/2007 | Hu et al. |

(Continued)

FOREIGN PATENT DOCUMENTS

AU          710696          9/1999

(Continued)

OTHER PUBLICATIONS

Joukov, V et al. The EMBO J. 15(7):1751, 1996.*

(Continued)

*Primary Examiner*—Robert Landsman
(74) *Attorney, Agent, or Firm*—Sterne, Kessler, Goldstein & Fox, P.L.L.C.

(57) ABSTRACT

Disclosed are human VEGF2 polypeptides, biologically active, diagnostically or therapeutically useful fragments, analogs, or derivatives thereof, and DNA (RNA) encoding such VEGF2 polypeptides. Also provided are procedures for producing such polypeptides by recombinant techniques and antibodies and antagonists against such polypeptides. Such polypeptides may be used therapeutically for stimulating wound healing and for vascular tissue repair. Also provided are methods of using the antibodies and antagonists to inhibit tumor angiogenesis and thus tumor growth, inflammation, diabetic retinopathy, rheumatoid arthritis, and psoriasis.

5 Claims, 47 Drawing Sheets

U.S. PATENT DOCUMENTS

| | | | |
|---|---|---|---|
| 7,208,582 | B2 | 4/2007 | Rosen et al. |
| 7,223,724 | B1 | 5/2007 | Alderson et al. |
| 7,227,005 | B1 | 6/2007 | Hu et al. |
| 7,273,751 | B2 | 9/2007 | Coleman |
| 2003/0215921 | A1 | 11/2003 | Coleman |
| 2004/0214286 | A1 | 10/2004 | Hu et al. |
| 2005/0059117 | A1 | 3/2005 | Rosen et al. |
| 2005/0181979 | A1 | 8/2005 | Alderson et al. |
| 2005/0192429 | A1 | 9/2005 | Rosen et al. |
| 2005/0232921 | A1 | 10/2005 | Rosen et al. |
| 2005/0287143 | A1 | 12/2005 | Rosen et al. |
| 2006/0014252 | A1 | 1/2006 | Lyman |
| 2006/0025331 | A1 | 2/2006 | Hu et al. |
| 2006/0057117 | A1 | 3/2006 | Coleman |

FOREIGN PATENT DOCUMENTS

| | | |
|---|---|---|
| EP | 0 186 084 A2 | 7/1986 |
| EP | 0 399 816 A1 | 11/1990 |
| EP | 0 476983 | 3/1992 |
| EP | 0 506477 | 9/1992 |
| JP | 64-38100 A | 2/1989 |
| JP | 2-117698 A | 5/1990 |
| WO | WO-91/02058 | 2/1991 |
| WO | WO-92/14748 | 9/1992 |
| WO | WO 94/11506 A1 | 5/1994 |
| WO | WO-95/19985 | 7/1995 |
| WO | WO-95/24414 | 9/1995 |
| WO | WO-95/24473 | 12/1995 |
| WO | WO-96/05856 | 2/1996 |
| WO | WO-96/39515 | 12/1996 |
| WO | WO-97/00271 | 1/1997 |
| WO | WO-97/05250 | 2/1997 |
| WO | WO-97/08320 | 3/1997 |
| WO | WO-97/09427 | 3/1997 |
| WO | WO-97/17442 | 5/1997 |
| WO | WO-97/19694 | 6/1997 |
| WO | WO-98/06844 | 2/1998 |
| WO | WO-98/07832 | 2/1998 |
| WO | WO-98/24811 | 6/1998 |
| WO | WO-98/33917 | 6/1998 |
| WO | WO-98/39035 | 9/1998 |
| WO | WO-98/49300 | 11/1998 |
| WO | WO-98/55619 | 12/1998 |
| WO | WO-98/56936 | 12/1998 |
| WO | WO-99/02545 | 1/1999 |
| WO | WO-99/08522 | 2/1999 |
| WO | WO-99/20749 | 4/1999 |
| WO | WO-99/21590 | 5/1999 |
| WO | WO-99/46364 | 9/1999 |
| WO | WO 00/45835 A1 | 8/2000 |
| WO | WO-00/73430 A3 | 12/2000 |
| WO | WO-00/75163 | 12/2000 |
| WO | WO-01/57226 A1 | 8/2001 |
| WO | WO-01/58956 A3 | 8/2001 |
| WO | WO 02/11769 A1 | 2/2002 |
| WO | WO 02/083704 A1 | 10/2002 |
| WO | WO 02/083849 A2 | 10/2002 |
| WO | WO 02/083850 A2 | 10/2002 |
| WO | WO 03/097660 A1 | 11/2003 |
| ZA | 9-403464 | 1/1996 |

OTHER PUBLICATIONS

U.S. Appl. No. 09/257,272, inventors Hu et al., filed Feb. 25, 1999 (Not Published).

U.S. Appl. No. 09/499,468, inventors Alderson et al., filed Feb. 7, 2000 (Not Published).

U.S. Appl. No. 11/730,696, inventors Rosen et al., filed Apr. 3, 2007 (Not Published).

Anderson, W.F., "Human gene therapy," *Nature* 392:25-30, Macmillan Magazines Ltd. (Apr. 1998).

Borg, J.-P., et al., "Biochemical characterization of two isoforms of FLT4, a VEGF receptor-related tyrosine kinase," *Oncogene* 10:973-984, Stockton Press (Mar. 1995).

Capogrossi, M.C., "Gene Therapy of Coronary Artery Disease," Project No. Z01 AG00811-01, Abstract (Jan. 1994).

Capogrossi, M.C., "Gene Therapy of Coronary Artery Disease," Project No. Z01 AG00811-02, Abstract (Jan. 1995).

Choi, I.H., et al., "Angiogenesis and Mineralization During Distraction Osteogenesis," *J. Korean Med. Sci.* 17:435-447, The Korean Academy of Medical Sciences (Aug. 2002).

Declaration of Dr. Kari Alitalo, In re of: U.S. Appl. No. 08/585,895, Alitalo et al., filed Jan. 12, 1996, submitted Nov. 26, 1997.

Dias, S., et al., "Vascular endothelial growth factor (VEGF)-C signaling through FLT-4 (VEGFR-3) mediates leukemic cell proliferation, survival, and resistance to chemotherapy," *Blood* 99:2179-2184, The American Society of Hematology (Mar. 2002).

English language abstract of JP 64-38100 A, cited as document FP2 on Form PTO/SB/08A, Derwent Accession No. 1989-088700/198912.

English language abstract of JP 2-117698 A, cited as document FP3 on Form PTO/SB/08A, Derwent Accession No. 1990-181364/199024.

Danis, R.P., et al., "Anti-angiogenic therapy of proliferative diabetic retinopathy," *Exp. Opin. Pharma.* 2:395-407, Ashley Publications Ltd. (Mar. 2001).

Enholm, B., et al., "Vascular Endothelial Growth Factor-C: A Growth Factor for Lymphatic and Blood Vascular Endothelial Cells," *Trends Cardiovasc. Med.* 8:292-297, Elsevier Science Inc. (Oct. 1998).

Fan, T.-P.D., et al., "Controlling the vasculature: angiogenesis, anti-angiogenesis and vascular targeting of gene therapy," *Trends Pharmaco. Sci.* 16:57-66, Elsevier Science Ltd. (Feb. 1995).

Ferrara, N., "Vascular Endothelial Growth Factor and the Regulation of Angiogenesis," *Recent Prog. Hormone Res.* 55:15-36, The Endocrine Society (Mar. 2000).

Halin, C. and Neri, D., "Antibody-Based Targeting of Angiogenesis," *Crit. Rev. Ther. Drug Carrier Syst.* 18:299-339, Begell House, Inc. (Aug. 2001).

Isner, J.M., et al., "Arterial Gene Therapy for Therapeutic Angiogenesis in Patients With Peripheral Artery Disease," *Circulation* 91:2687-2692, American Heart Association, Inc. (Jun. 1995).

Isner, J.M. and Feldman, L.J., "Gene therapy for arterial disease," *Lancet* 344:1653-1654, The Lancet Ltd. (Dec. 1994).

Isner, J.M., et al., "Physiologic Assessment of Angiogenesis by Arterial Gene Therapy with Vascular Endothelial Growth Factor," *J. Cell. Biochem. (Suppl. 21A)*:378, Abstract C6-215, Wiley-Liss (Mar.-Apr. 1995).

Isner, J.M., "Therapeutic Angiogenesis in Vascular Medicine," Project No. R01 HL53354-01, Abstract (Mar. 1995).

Kubo, H., et al., "Blockade of vascular endothelial growth factor receptor-3 signaling inhibits fibroblast growth factor-2-induced lymphangiogenesis in mouse cornea," *Proc. Natl. Acad. Sci.* 99:8868-8873, The National Academy of Sciences (Jun. 2002).

Kuzuya, M. and Kinsella, J.L., "Induction of Endothelial Cell Differentiation in Vitro by Fibroblast-Derived Soluble Factors," *Exp. Cell Res.* 215:310-318, Academic Press, Inc. (Dec. 1994).

Longo, R., et al., "Anti-angiogenic therapy: Rationale, challenges and clinical studies," *Angiogenesis* 5:237-256, Kluwer Academic Publishers (Dec. 2002).

Maher, P.A., "Stimulation of Endothelial Cell Proliferation by Vanadate Is Specific for Microvascular Endothelial Cells," *J. Cell. Physiol.* 151:549-554, Wiley-Liss, Inc. (1992).

Maynard, J. and Georgiou, G., "Antibody Engineering," *Annu. Rev. Biomed. Eng.* 2:339-376, Annual Reviews (Aug. 2000).

Mesri, E.A., et al., "Expression of Vascular Endothelial Growth Factor From a Defective Herpes Simplex Virus Type 1 Amplicon Vector Induces Angiogenesis in Mice," *Circulation Res.* 76:161-167, American Heart Association, Inc. (Feb. 1995).

Morea, V., et al., "Antibody Modeling: Implications for Engineering and Design," *Methods* 20:267-279, Academic Press (Mar. 2000).

Mühlhauser, J., et al., "In Vivo Gene Transfer into Porcine Cardiac Cells with a Replication-Deficient Recombinant Adenovirus Vector," *Circulation* 88:I-475, Abstract No. 2558, American Heart Association (Oct. 1993).

Mühlhauser, J., et al., "VEGF$_{165}$ Expressed by a Replication-Deficient Recombinant Adenovirus Vector Induces Angiogenesis In Vivo," *Circulation Res.* 77:1077-1086, American Heart Association, Inc. (Dec. 1995).

Oikawa, T., et al., "Three Isoforms of Platelet-Derived Growth Factors All Have the Capability to Induce Angiogenesis In Vivo," *Biol. Pharm. Bull.* 17:1686-1688, (Dec. 1994).

Pajusola, K., et al., "Signalling properties of FLT4, a proteolytically processed receptor tyrosine kinase related to two VEGF receptors," *Oncogene* 9:3545-3555, Macmillan Press Ltd. (Dec. 1994).

Pepper, M.S., et al., "In Vitro Angiogenic and Proteolytic Properties of Bovine Lymphatic Endothelial Cells," *Exp. Cell Res.* 210:298-305, Academic Press, Inc. (Jan. 1994).

Plate, K.H., "From angiogenesis to lymphangiogenesis," *Nat. Med.* 7:151-152, Nature America, Inc. (Feb. 2001).

Spranger, J. and Pfeiffer, A.F.H., "New concepts in pathogenesis and treatment of diabetic retinopathy," *Exp. Clin. Endocrinol. Diabetes* 109(Suppl. 2):S438-S450, J.A. Barth Verlag (2001).

Symes, J.F. and Sniderman, A.D., "Angiogenesis: potential therapy for ischaemic disease," *Curr. Opin. Lipidol.* 5:305-312, Current Science Ltd. (Aug. 1994).

Takeshita, S., et al., "In Vivo Evidence of Enhanced Angiogenesis Following Direct Arterial Gene Transfer of the Plasmid Encoding Vascular Endothelial Growth Factor," *Circulation* 88:I-476, Abstract No. 2565, American Heart Association (Oct. 1993).

Takeshita, S., et al., "Therapeutic Angiogenesis. A Single Intraarterial Bolus of Vascular Endothelial Growth Factor Augments Revascularization in a Rabbit Ischemic Hind Limb Model," *J. Clin. Invest.* 93:662-670, The American Society for Clinical Investigation, Inc. (Feb. 1994).

Walsh, D.A. and Pearson, C.I., "Angiogenesis in the pathogenesis of inflammatory joint and lung diseases," *Arthritis Res.* 3:147-153, BioMed Central Ltd. (Feb. 2001).

Walsh, D.A., "Angiogenesis and arthritis," *Rheumatology* 38:103-112, British Society for Rheumatology (Feb. 1999).

Williams, R.S., "Southwestern Internal Medicine Conference: Prospects for Gene Therapy of Ischemic Heart Disease," *Am. J. Med. Sci.* 306:129-136, Lippincott Williams & Wilkins (Aug. 1993).

Witzenbichler, B., et al., "Vascular Endothelial Growth Factor-C (VEGF-C/VEGF-2) Promotes Angiogenesis in the Setting of Tissue Ischemia," *Am. J. Pathol.* 153:381-394, American Society for Investigative Pathology, Inc. (Aug. 1998).

Yeung, P.K.F., "VEGF-2," *Curr. Opin. Invest. Drugs* 2:796-800, PharmaPress Ltd. (Jun. 2001).

NCBI Entrez, Accession No. AF010302, Mandriota S.J. and Pepper, M.S. (Jul. 16, 1997).

Letter from John. J. Chicca II, Ph.D., Molecular Diagnostic Services, Inc. regarding a third progress report for a project entitled "Cloning and expression of VEGF-2 gene and the efficacy of VEGF-2 protein utilizing the 3-D collagen angiogenesis assay and proliferation," dated Feb. 16, 2006.

Letter from John. J. Chicca II, Ph.D., Molecular Diagnostic Services, Inc. regarding a fourth progress report for a project entitled "Cloning and expression of VEGF-2 gene and the efficacy of VEGF-2 protein utilizing the 3-D collagen angiogenesis assay and proliferation," dated Mar. 14, 2006.

Achen et al., "Vascular endothelial growth factor D (VEGF-D) is a ligand for the tyrosine kinases VEGF receptor-2 (Flk1) and VEGF receptor 3 (Flt4)," *Proc. Natl. Acad. Sci. (USA)*, 95(2):548-553 (1998).

Alderson et al. (1999) Vascular endothelial cell growth factor (VEGF)-2 enhances the development of rat photoreceptor cells in vitro. Keystone Symposia, Ocular Cell and Molecular Biology, 202. (Abstract provided).

Altshuler et al., "Taurine promotes the differentiation of a vertebrate retinal cell type in vitro," *Development*, 119:1317-1328 (1993).

Andersson et al., "Assignment of interchain disulfide bonds in platelet-derived growth factor (PDGF) and evidence for agonist activity of monomeric PDGF," *J. Biol. Chem.*, 267(16):11260-11266 (1992).

Andersson W.F., "Human gene therapy," *Science*, 256:808-813 (1992).

Aprelikova et al., "FLT4, a novel class III receptor tyrosine kinase in chromosome 5q33-qter," *Cancer Research*, 52:746-748 (1992).

Bell et al., "Human epidermal growth factor precursor: cDNA sequence, expression in vitro and gene organization," *Nucl. Acids Res.* 14(21):8427-8446 (1986).

Bellomo et al., "Mice Lacking the Vascular Endothelial Growth Factor-B Gene (Vegfb) Have Smaller Hearts, Dysfunctional Coronary Vasculature, and Impaired Recovery From Cardiac Ischemia," *Circ. Research* 89(2):e29-e35 (2000).

Berse et al., "Vascular permeability factor (vascular endothelial growth factor) gene is expressed differentially in normal tissues, macrophages, and tumors," *Mol. Biol. Cell.* 3:211-220 (1992).

Betsholtz et al., "cDNA sequence and chromosomal localization of human platelet-derived growth factor A-chain and its expression in tumor cell lines," *Nature* 320:695-699 (1986).

Bocker-Meffert et al., "Erythropoietin and VEGF Promote Neural Outgrowth from Retinal Explants in Postnatal Rats," *Invest. Ophthalmol. Vis. Sci.*, 43(6):2021-2026 (2002).

Breier et al., "Expression of vascular endothelial growth factor during embryonic angiogenesis and endothelial cell differentiation," *Development* 114:521-532 (1992).

Claffey et al., "Vascular endothelial growth factor," *J. Biol. Chem.* 267(23):16317-16322 (1992).

Cockerill et al., "Angiogenesis: Models and Modulators" *Intl. Rev. Cytology* 159:113-160 (1995).

Corson et al., "Fibrillin binds calcium and is coded by cDNAs that reveal a multidomain structure and alternatively spliced exons at the 5' end," *Genomics* 17:476-484 (1993).

Dignam et al., "Balbiani ring 3 in *Chironomus tentans* encodes a 185-kDa secretory protein which is synthesized throughout the fourth larval instar," *Gene* 88:133-140 (1990).

Eichmann et al., "Avian VEGF-C: cloning, embryonic expression pattern and stimulation of the differentiation of VEGFR2-expressing endothelial cell precursors," *Development* 125(4):743-752 (1998).

Ferrara et al., "Molecular and biological properties of the vascular endothelial growth factor family of proteins," *Endocrine Rev.* 13(I):18-32 (1992).

Ferrara et al., "The vascular endothelial growth factor family of polypeptides," *J. Cellular Biochemistry* 47:211-218 (1991).

Finnerty et al., "Molecular cloning of murine FLT and FLT4,"*Oncogene* 8(11):2293-2298 (1993).

Friedman, T., "A brief history of gene therapy," *Nat. Genetics* 2:93-98 (1992).

Gail M. Seigel, "The golden age of retinal cell culture," *Molec. Vis.* 5:4 (1999).

Gamble et al., "Regulation of In Vitro Capillary Tube Formation by Anti-Integrin Antibodies," *J. Cell. Bio.* 121(4):931-943 (1993).

George et al., "Current Methods in Sequence Comparison and Analysis," Macromolecular Seq. and Syn. Selected Meth—Application (Alan R. Liss), pp. 127-149 (1988).

Gerhardinger et al., "Expression of Vascular Endothelial Growth Factor in the Human Retina and in Nonproliferative Diabetic Retinopathy," *Am. J. Pathol.*, 152(6):1453-1462 (Jun. 6, 1998).

Goldspiel et al., "Human Gene Therapy," *Clinical Pharmacy* 12:488-505 (1993).

Grimmond et al., "Cloning and Characterization of a Novel Human Gene Related to Vascular Endothelial Growth Factor," *Genome Research* 6:124-131 (1996).

Guzman et al. "Efficient gene transfer into myocardium by direct injection of adenovirus vectors," *Circ. Res.* 73:1202-1207 (1993).

Hannink et al., "Deletions in the C-Terminal Coding Region of the v-sis Gene: Dimerization Is Required for Transformation" *Mol. And Cellular Biol.* 1304-1314 (1986).

Hirai et al., "Expression of Vascular Endothelial Growth Factors (VEGF-A/VEGF-1 and VEGF-C/VEGF-2) in Postmenopausal Uterine Endometrial Carcinoma," *Gynecol. Oncol.* 80:181-188 (2001).

Heldin et al., "Structure of platelet-derived growth factor: implications for functional properties," *Growth Factors* 8:245-252 (1993).

Hockel et al., "Therapeutic angiogenesis," *Arch. Surg.* 128:423-429 (1993).

Hu et al., "A novel regulatory function of proteolytically cleaved VEGF-2 for vascular endothelial smooth muscle cells," *FASEB J.*, 11:498-504 (1997).

Hyde et al., "Correction of the ion transport defect in cystic fibrosis transgenic mice by gene therapy," *Nature* 362:250-255 (1993).

Joukov et al., "A novel vascular endothelial growth factor, VEGF-C, is a ligand for the Flt4 (VEGFR-3) and KDR (VEGFR-2) receptor tyrosine kinases," *EMBO J.* 15(2):290-298 (1996).

Joukov et al., "Proteolytic processing regulates receptor specificity and activity of VEGF-C," *EMBO J.* 16(13):3898-3911 (1997).

Kaipainen et al., "The related FLT4, FLT1 and KDR receptor tyrosine kinases show distinct expression patterns in human fetal endothelial cells," *J. Exp. Med.* 178:2077-2088 (1993).

Kay et al., "In Vivo Gene Therapy of Hemophilia B: Sustained Partial Correction in Factor IX-Deficient Dogs," *Science* 262:117-119 (1993).

Keck et al., "Vascular permeability factor, an endothelial cell mitogen related to PDGF," *Science* 246:1309 (1989).

Kelley et al., "Regulation of a Proliferation and Photoreceptor Differentiation in Fetal Human Retinal Cell Cultures," *Invest. Ophthalmol. Vis. Sci.* 36(7):1280-1289 (1995).

Kingsley, D., "The TGF-b superfamily: new members, new receptors, and new genetic tests of function in different organisms," *Genes & Development* 8:133-146 (1994).

Kolodka et al., "Hepatic Gene Therapy: Efficient Retroviral-Mediated Gene Transfer into Rat Hepatocytes in Vivo," *Somatic Cell and Molecular Genetics* 19(5):491-497 (1993).

Kukk et al., "VEGF-C receptor binding and pattern of expression with VEGFR-3 suggests a role in lymphatic vascular development," *Development* 122:3829-37 (1996).

Lee et al., "Vascular endothelial growth factor-related protein: a ligand and specific activator of the tyrosine kinase receptor Flt4," *Proc. Natl. Acad. Sci.* (USA), 93:1988-1992 (1996).

Leung et al., "Vascular endothelial growth factor is a secreted angiogenic mitogen," *Science* 246:1306-1309 (1989).

Litwin et al., "Role of Cytokines in Endothelial Cell Functions," *Human Cytokines* pp. 101-129 (1995).

Maglione et al., "Isolation of a human placenta cDNA coding for a protein related to the vascular permeability factor," *Proc. Natl. Acad. Sci.* (USA), 88:9267-9271 (1991).

Maglione et al., "Two alternative mRNAs coding for the angiogenic factor, placenta growth factor (PIGF), are transcribed from a single gene of chromosome 14," *Oncogene* 8:925-931 (1993).

Massague, J., "The transforming growth factor-beta family," *Annu. Rev. Cell Biol.* 6:597-641 (1990).

Matthews et al., "A receptor tyrosine kinase cDNA isolated from a population of enriched primitive hematopoietic cells and exhibiting close genetic linkage to c-kit," *Proc. Natl. Acad. Sci.* (USA), 88:9026-9030 (1991).

Millauer et al., "Glioblastoma growth inhibited in vivo by a dominant-negative Flk-1 mutant," *Nature* 367:576-579 (1994).

Millauer et al., "High affinity VEGF binding and developmental expression suggest FLK-1 as a major regulator of vasculogenesis and angiogenesis," *Cell* 72:835-846 (1993).

Ngo et al., The Protein Folding Problem and Tertiary Structure Prediction, Kenneth Merz, Jr. and Scott LeGrand, eds., Birkhauser, Boston, pp. 492-495 (1994).

Oltvai et al., "Bcl-2 heterodimerizes in vivo with a conserved homolog, bax, that accelerates programmed cell death," *Cell* 74:609-619 (1993).

Pajusola et al., "FLT4 receptor tyrosine kinase contains seven immunoglobulin-like loops and is expressed in multiple human tissues and cell lines," *Cancer Research* 52:5738-5743 (1992).

Pajusola et al., "Two human FLT4 receptor tyrosine kinase isoforms with distinct carboxy terminal tails are produced by alternative processing of primary transcripts," *Oncogene* 8:2931-2937 (1993).

Paulsson et al., "The balbani ring 3 gene in *Chironomus tentans* has a diverged repetitive structure split by many introns," *J. Mol. Biol.* 211:331-349 (1990).

Rudikoff et al., "Single amino acid substitution altering antigen-binding specificity," *Proc. Natl. Acad. Sci. USA*, 79(6):1979-1983 (Mar. 1982).

Schratzberger et al., "Reversal of experimental diabetic neuropathy by VEGF gene transfer," *J. Clin. Invest.* 107(9):1083-1092 (May 2001).

Schulz-Key et al., "Ciliary Neurotrophic Factor as a Transient Negative Regulator of Rod Development in Rat Retina," *Invest. Ophthamol. Vis. Sci.* 43(9):3099-3108 (2002).

Shibuya et al., "Nucleotide sequence and expression of a novel human receptor-type tyrosine kinase gene (*flt*) closely related to the *fms* family," *Oncogene* 519-524 (1990).

Silins et al., "Analysis of the Promoter Region of the Human VEGF-Related Factor Gene," *Biochem. Biophys. Res. Comm.* 230:413-418 (1997).

Stacker et al., "The Vascular Endothelial Growth Factor Family: Signalling for Vascular Development," *Growth Factors*, vol. 17, pp. 1-11 (1999).

Stewart et al., "Insulin delivery by somatic cell gene therapy," *J. of Mol. Endocrinology* 11:335-341 (1993).

Tanaka et al., "DNA sequence encoding the amino-terminal region of the human c-*src* protein: implications of sequence divergence among *src*-type kinase oncogenes," *Mol. Cell Biol.* 7(5):1978-1983 (1987).

Terman et al., "Identification of a new endothelial cell growth factor receptor tyrosine kinase," *Oncogene* 6:1677-1683 (1991).

Terman et al., "Identification of the kdr tyrosine kinase as a receptor for vascular endothelial cell growth factor," *Biochem. Biophys. Res. Commun.* 187(3):1579-1586 (1992).

Tischer et al., "Vascular endothelial growth factor: A new member of the platelet-derived growth factor gene family," *Biochem. & Biophys. Res. Comms.* 165(3):1198-1206 (1989).

Tischer et al., "The Human Gene for Vascular Endothelial Growth Factor," *J. Biol. Chem.* 266(18):11947-11954 (1991).

Townson et al., "Characterization of the Murine VEGF-Related Factor Gene," *Biochem. & Biophys. Res. Comms.* 220:922-928 (1996).

Tsujimoto et al., "Analysis of the structure, transcripts, and protein products of *bcl-2*, the gene involved in human follicular lymphoma," *Proc. Natl. Acad. Sci.* (USA), 83:5214-5218 (1986).

Vale et al., "Percutaneous Electromechanical Mapping Demonstrates Efficacy of pVGI.1 (VEGF2) in an Animal Model of Chronic Myocardial Ischemia," *Circulation* (Supplement), 100(18):I.22 (Nov. 2, 1999).

Vale et al., "Randomized, Single-Blind, Placebo-Controlled Pilot Study of Catheter-Based Myocardial Gene Transfer for Therapeutic Angiogenesis Using Left Ventricular Electromechanical Mapping in Patients with Chronic Myocardial Ischemia," *Circulation*, 103:17:2138-2143 (May 1, 2001).

Walsh et al., "Gene Therapy for Human Hemoglobinopathies," *P.S. E.B.M.* 204:289-300 (1993).

Williams, R.S. "Southwestern internal medicine conference: prospects for gene therapy of ischemic heart disease," *Am. J. Med. Sci.* 306(2):129-136 (1993).

Yang et al., "Flk-1, a Receptor for Vascular Endothelial Growth Factor (VEGF), Is Expressed by Retinal Progenitor Cells," *J. Neuroscience*, 16(19):6089-6099 (Oct. 1, 1996).

Yourey et al., "Vascular Endothelial Cell Growth Factors Promote the In Vitro Development of Rat Photoreceptor Cells," *Molecul. Biol. Cell*, 10(Suppl.):39a (Nov. 1999) and 39th Ann. Mtg. Am. Soc. Cell Biol., Wash, DC, (Dec. 11-15, 1999) (abstract (227) only).

Yourey, et al., "Vascular Endothelial Cell Growth Factors Promote the In Vitro Development of Rat Photoreceptor Cells" *Neuroscience*, 20:6781-6788 (2000).

GenBank Accession No. X68203, Aprelikova et al., "*H.sapiens* mRNA for FLT4, class III receptor tyrosine kinase," Nov. 30, 1993.

GenBank Accession No. M95200, Claffey et al., "Mouse vascular endothelial growth factor mRNA, complete cds," Apr. 27, 1993.

GenBank Accession No. M24160, Dignam et al., "*C.tentans* 185-kd secretory protein (sp185) mRNA, partial cds, clone pCt185," Apr. 26, 1993.

GenBank Accession No. M24276, Dignam et al., "*C.tentans* 140-kd secretory protein (sp140) mRNA, partial cds, clone pCt140.1," Apr. 26, 1993.

GenBank Accession No. M24277, Dignam et al., "*C.tentans* 140-kd secretory protein (sp140) mRNA, partial cds, clone pCt140.2," Apr. 26, 1993.

GenBank Accession No. D88689, Finnerty et al., "*Mus musculus* mRNA for flt-1, complete cds," Apr. 14, 2000.

GenBank Accession No. L07296, Finnerty et al., "*Mus musculus* receptor tyrosine kinase (FLT4) mRNA, complete cds," Aug. 9, 1993.

GenBank Accession No. X54936, Maglione et al., "*H.sapiens* mRNA for placenta growth factor (PIGF)," Nov. 12, 1991.

GenBank Accession No. S57152, Maglione et al., "*Homo sapiens* placenta growth factor 2 (PlGF-2) gene, partial cds," Mar. 5, 2001.
GenBank Accession No. X59397, Matthews et al., "Mouse Flk-1 mRNA for a tyrosine kinase receptor," Nov. 6, 1991.
GenBank Accession No. X52263, Paulsson et al., "*C.tentans* balbiani ring 3 (BR3) gene," Dec. 18, 1992.
GenBank Accession No. M63971, Tischer et al., "Human vascular endothelial growth factor gene, exon 1," Aug. 1993.
GenBank Accession No. M63972, Tischer et al., "Human vascular endothelial growth factor gene, exon 2," Aug. 3, 1993.
GenBank Accession No. M63973, Tischer et al., "Human vascular endothelial growth factor gene, exon 3," Aug. 3, 1993.
GenBank Accession No. M63974, Tischer et al., "Human vascular endothelial growth factor gene, exon 4," Aug. 3, 1993.
GenBank Accession No. M63975, Tischer et al., "Human vascular endothelial growth factor gene, exon 5," Aug. 3, 1993.
GenBank Accession No. M63976, Tischer et al., "Human vascular endothelial growth factor gene, exon 6," Aug. 3, 1993.
GenBank Accession No. M63977, Tischer et al., "Human vascular endothelial growth factor gene, exon 7," Aug. 3, 1993.
GenBank Accession No. M63978, Tischer et al., "Human vascular endothelial growth factor gene, exon 8," Aug. 3, 1993.
GenBank Accession No. M27281, Keck et al., "Human vascular permeability factor mRNA, complete cds," Aug. 3, 1993.
GenBank Accession No. X04571, Bell et al., "Human mRNA for kidney epidermal growth factor (EGF) precursor," Mar. 21, 1995.
GenBank Accession No. X63556, Corson et al., "*H. sapiens* mRNA for fibrillin," Feb. 17, 1997.
GenBank Accession No. L19896, Corson et al., "Human fibrillin (FBN1) gene, 5'end including alternative exons A, B, and C, and exon M," Nov. 8, 1994.
GenBank Accession No. L04947, Terman et al., "*Homo sapiens* (clones BT3.081.8, BT3.129.5 and BT4.169," Jan. 6, 1995.
GenBank Accession No. M16237, Tanaka et al., "Human c-src-1 proto-oncogene, exon 2," Jan. 13, 1995.
GenBank Accession No. M16243, Tanaka et al., "Human c-src-1 proto-oncogene, exon 3," Jan. 13, 1995.
GenBank Accession No. M16244, Tanaka et al., Human c-src-1 proto-oncogene, exon 4, Jan. 13, 1995.
GenBank Accession No. M16245, Tanaka et al., "Human c-src-1 proto-oncogene, exon 5," Jan. 13, 1995.
GenBank Accession No. K03212, Anderson et al., "Human c-src-1 proto-oncogene, exon 6," Jan. 13, 1995.
GenBank Accession No. K03213, Anderson et al., "Human c-src-1 proto-oncogene, exon 7," Jan. 13, 1995.
GenBank Accession No. K03214, Anderson et al., "Human c-src-1 proto-oncogene, exon 8", Jan. 13, 1995.
GenBank Accession No. K03215, Anderson et al., "Human c-src-1 proto-oncogene, exon 9", Jan. 13, 1995.
GenBank Accession No. K03216, Tanaka et al., Human c-src-1 proto-oncogene, exon 10, Jan. 13, 1995.
GenBank Accession No. K03217, Tanaka et al., "Human c-src-1 proto-oncogene, exon 11," Jan. 13, 1995.
GenBank Accession No. K03219, Tanaka et al., "Human c-src-1 proto-oncogene, exon 12," Jan. 13, 1995.
GenBank Accession No. M13994, Tsujimoto et al., "Human B-cell leukemia/lymphoma 2 (bcl-2) proto-oncogene mRNA encoding bcl-2-alpha protein, complete cds," Oct. 31, 1994.
GenBank Accession No. M13995, Tsujimoto et al., "Human B-cell leukemia/lymphoma 2 (bcl-2) proto-oncogene mRNA encoding bcl-3-beta protein, complete cds," Oct. 31, 1994.
GenBank Accession No. L22473, Oltvai et al., "Human Bax alpha mRNA, complete cds," Dec. 15, 1993.
GenBank Accession No. L22474, Oltvai et al., "Human Bax beta mRNA, complete cds," Dec. 13, 1993.
GenBank Accession No. AJ000185, Achen et al., "*Homo sapiens* mRNA for vascular endothelial growth factor-D," Feb. 11, 1998.
GenBank Accession No. S08167, Paulsson et al., "Balbiani ring 3 protein—midge (*Chironomus tentans*)," 1990.
International Search Report, Application No. PCT/US99/05021.
International Search Report, Application No. PCT/US94/05291.
International Search Report, Application No. PCT/US01/24658.

International Search Report, Application No. PCT/US02/26246, mailed May 21, 2003.
Statutory Declaration of Kari Alitalo, executed on Aug. 14, 2002, and accompanying Exhibits KA-1 and KA-2.
Statutory Declaration of Peter Adrian Walton Rogers, executed on Aug. 9, 2002.
Statutory Declaration of Francis John Ballard, executed on Jul. 16, 2002.
Statutory Declaration of Kari Alitalo, executed on Jul. 16, 2002, and accompanying Exhibit 1.
Statutory Declaration of Susan Power, executed on Mar. 22, 2002, and accompanying Appendices I to IV.
Statutory Declaration of Nicholas Kim Hayward, executed on Mar. 26, 2002.
Statutory Declaration of Stuart A. Aaronson, executed on Mar. 22, 2002, and accompanying Appendices I to III.
Statutory Declaration of Gary Baxter Cox, executed on Mar. 22, 2002, and accompanying Exhibit GBC24 (Statutory Declaration of Peter Adrian Walters, executed on Oct. 26, 2001).
Statutory Declaration of Frances John Ballard, executed on Dec. 12, 2001, and accompanying Exhibit 1.
Statutory Declaration of Kari Alitalo, executed on Sep. 24, 2001, and accompanying Exhibits 1 and 2.
Statutory Declaration of Peter Adrian Walton Rogers, executed on Nov. 12, 2001, and accompanying Exhibits PAWR1 to PAWR14.
Statutory Declaration of John Stanley Mattick, executed on Dec. 12, 2000, and accompanying Exhibits JSM1 to JSM4.
Statutory Declaration of Nicholas Kim Hayward, executed on Dec. 8, 2000, and accompanying Exhibits NKH 1 and 2.
Statutory Declaration of Jennifer Ruth Gamble, executed on Dec. 12, 2000, and accompany Exhibits JRG 1 to 3.
Statutory Declaration of Tom Rapoport, executed on Dec. 13, 2000, and accompanying Exhibits TP 1 and 2.
Statutory Declaration of Stuart A. Aaronson, executed on Dec. 14, 2000, and accompanying CV.
Statutory Declaration of Susan Power, executed on Dec. 13, 2000, and accompanying Appendices 1 to 2 and Figure 1.
Statutory Declaration of Gary Baxter Cox, executed on Dec. 13, 2000, and accompanying Exhibits GBC 1 to 23.
Statutory Declaration of Peter Adrian Walton Rogers, executed on Feb. 16, 2000, and accompanying Exhibit 1.
Statutory Declaration of Frances John Ballard, executed on Feb. 16, 2000, and accompanying Exhibit 1.
Statutory Declaration of Kari Alitalo, executed on Feb. 15, 2000, and accompanying Exhibits 1 to 3.
European Supplementary Search Report, Application No. EP 01 96 3814, mailed Jul. 14, 2004.
Supplementary Partial European Search Report, Application No. EP 02 72 6730, mailed Aug. 4, 2004.
Supplementary Partial European Search Report, Application No. EP 02 72 1715, mailed Jan. 10, 2005.
Supplementary Partial European Search Report, Application No. EP 02 72 1715, mailed Oct. 22, 2004.
EBI Accession No. AAW27553, Knappik et al., "Human Ab heavy chain variable region VH3 consensus" (Jan. 23, 1998).
Supplementary European Search Report, Application No. EP 02 72 6730, mailed Oct. 25, 2004.
Supplementary European Search Report, Application No. EP 00 90 5992, mailed Nov. 8, 2004.
Joosten et al., "The production of antibody fragments and antibody fusion proteins by yeasts and filamentous fungi," *Microbial Cell Factories* 2:1 (Jan. 30, 2003).
Skerra et al., "Assembly of a functional immunoglobulin Fv fragment in *Escherichia coli*," *Science* 240(4855):1038-1041 (May 20, 1988).
Better et al., "*Escherichia coli* secretion of an active chimeric antibody fragment," *Science* 240(4855):1041-1043 (May 20, 1988).
Verma et al., "Gene therapy—promises, problems and prospects," Nature 389:239-242 (1997).
Houck, et al., "The vascular endothelial growth factor family: identification of a fourth molecular species and characterization of alternative splicing of RNA." Molecular Endocrinology. 5(12):1806-14 (1991).

Colwell, et al., "Method for generating a high frequency of hybridomas producing monoclonal IgA antibodies." Methods Enzymol. 121:42-51 (1986).

Schlaeppi, et al., "Characterization of a new potent, in vivo neutralizing monoclonal antibody to human vascular endothelial growth factor." J Cancer Res. Clin. Oncol. 125:336-342 (1999).

Van Der Flier, et al., "Antibody neutralization of vascular endothelial growth factor (VEGF) fails to attenuate vascular permeability and brain edema in experimental pneumococcal meningitis." J. Neuroimmunology 160:170-177 (2005).

Winkler, et al., "Changing the antigen binding specificity by single point mutations of an Anti-p24 (HIV-1) antibody." J Immunology 165:4505-4514 (2000).

U.S. Appl. No. 11/980,495, inventors Rosen et al., filed Oct. 31, 2007 (Not Published).

* cited by examiner

```
      GTCCTTCCACCATGCACTGCTGGGCTTCTTCTCTGTGGCGTGTTCTCTGCTCCGCCGCTG
  1   ------+---------+---------+---------+---------+---------+   60
      CAGGAAGGTGGTACGTGACGACCCGAAGAAGAGACACCGCACAAGAGACGAGGGCCGAC
                   M  H  S  L  G  F  F  S  V  A  C  S  L  L  A  A  -

CGCTGCTCCGGGTCTCCGGAGGCGCTCCTCCCGGGCCCGCGCCTTCCAGTCCGGACTCG
 61   ------+---------+---------+---------+---------+---------+  120
      GCGACGAGGGCCCAGAGGCCTCCGCGAGGAGGGCCCGGGCGCGGAAGGTCAGGCCTGAGC
        L  L  P  G  P  R  E  A  P  A  A  A  A  A  F  E  S  G  L  D  -

ACCTCTCGGACGCGGAGCCCGACGCGGCGAGGCCACGGCTTATGCAAGCAAAGATCTGG
121   ------+---------+---------+---------+---------+---------+  180
      TGGAGAGCCTGCGCCTCGGGCTGCGCCGCTCCGGTGCCGAATACGTTCGTTTCTAGACC
        L  S  D  A  E  P  D  A  G  E  A  T  A  Y  A  S  K  D  L  E  -

AGGAGCAGTTACGGTCTCTGTGTCCAGTGTAGATGAACTCATGACTGTACTCTACCCAGAAT
181   ------+---------+---------+---------+---------+---------+  240
      TCCTCGTCAATGCCAGACACAGTCACATCTACTTGAGTACTGACATGAGATGGGTCTTA
        E  Q  L  R  S  V  S  S  V  D  E  L  M  T  V  L  Y  P  E  Y  -

ATTGGAAAATGTACAAGTGTCAGCTAAGGAAAGGAGGCTGGCAACATAACAGAGAACAGG
241   ------+---------+---------+---------+---------+---------+  300
      TAACCTTTTACATGTTCACAGTCGATTCCTTTCCTCCGACCGTTGTATTGTCTCTTGTCC
        W  K  M  Y  K  C  Q  L  R  K  G  G  W  Q  H  N  R  E  Q  A  -

CCAACCTCAACTCAAGGACAGAAGAGACTATAAAATTGCTGCAGCACATTATAATACAG
```

FIG. 1A

```
301 ----------+---------+---------+---------+---------+---------+ 360
    GGTTGGAGTTGAGTTCCTGTCTCTTCTGATATTTAAACGACGTCGTGTAATATTATGTC
     N  L  N  S  R  T  E  E  T  I  K  F  A  A  A  H  Y  N  T  E  -

AGATCTTGAAAAGTATTGATAATGAGTGGAGAAAGACTCAATGCCACGGGAGGTGT
361 ----------+---------+---------+---------+---------+---------+ 420
    TCTAGAACTTTTCATAACTATTACTCACCTCTTTCTGAGTTACGGTGCCCTCCACA
     I  L  K  S  I  D  N  E  W  R  K  T  Q  C  M  P  R  E  V  C  -

GTATAGATGTGGGAAGGAGTTTGGAGTCGGACAAACACCTTCTTTAAACCTCCATGTG
421 ----------+---------+---------+---------+---------+---------+ 480
    CATATCTACACCCTTCCTCAAACCTCAGCGCTGTTTGTGGAAGAAATTTGGAGGTACAC
     I  D  V  G  K  E  F  G  V  A  T  N  T  F  F  K  P  P  C  V  -

TGTCCGTCTACAGATGTGGGGCTTGCTGCAATAGTGAGGGCTGCAGTGCATGAACACCA
481 ----------+---------+---------+---------+---------+---------+ 540
    ACAGGCAGATGTCTACACCCCGAACGACGTTATCACTCCCGACGTCACGTACTGTGGT
     S  V  Y  R  C  G  G  C  C  N  S  E  G  L  Q  C  M  N  T  S  -

GCACGAGCTACCTCAGCAAGACGTTATTGAAATTACAGTGCCTCTCTCTCAAGGCCCCA
541 ----------+---------+---------+---------+---------+---------+ 600
    CGTGCTCGATGGAGTCGTTCTGCAATAAACTTTAATGTCACGGAGAGAGTTCCGGGT
     T  S  Y  L  S  K  T  L  F  E  I  T  V  P  L  S  Q  G  P  K  -

AACCAGTAACAATCAGTTTTGCCAATCACACTTCCTGCCGATGCATGTCTAAACTGGATG
601 ----------+---------+---------+---------+---------+---------+ 660
    TTGGTCATTGTTAGTCAAAACGGTTAGTGTGAAGGACGGCTACGTACAGATTTGACCTAC
     P  V  T  I  S  F  A  N  H  T  S  C  R  C  M  S  K  L  D  V
```

FIG. 1B

```
       TTTACAGACAAGTTCATTCCATTATTAGACGTTCCCTGCCAGCAACACTACCACAGTGTC
661    ------+---------+---------+---------+---------+---------+ 720
       AAATGTCTGTTCAAGTAAGGTAATAATCTGCAAGGACGGTCGTTGTGATGGTGTCACAG
           Y  R  Q  V  H  S  I  I  R  R  S  L  P  A  T  L  P  Q  C  Q  -

AGGCAGCGAACAAGACCTGCCCACCAATTACATGTGGAATAATCACATCTGCAGATGCC
721    ------+---------+---------+---------+---------+---------+ 780
       TCCGTCGCTTGTTCTGGACGGGTGGTTAATGTACACCTTATTAGTGTAGACGTCTACGG
           A  A  N  K  T  C  P  T  N  Y  M  W  N  N  H  I  C  R  C  L  -

TGGCTCAGGAAGATTTTATGTTTTCCTCGGATGCTGGAGATGACTCAACAGATGGATTCC
781    ------+---------+---------+---------+---------+---------+ 840
       ACCGAGTCCTTCTAAAATACAAAAGGAGCCTACGACCTCTACTGAGTTGTCTACCTAAGG
           A  Q  E  D  F  M  F  S  S  D  A  G  D  D  S  T  D  G  F  H  -

ATGACATCTGTGGACCAAACAAGGAGCTGGATGAAGAGACCTGTCAGTGTGTCTGCAGAG
841    ------+---------+---------+---------+---------+---------+ 900
       TACTGTAGACACCTGGTTTGTTCCTCGACCTACTTCTCTGGACCAGTCACACAGACGTCTC
           D  I  C  G  P  N  K  E  L  D  E  E  T  C  Q  C  V  C  R  A  -

CGGGGCTTCGGCCTGCCCAGCTGTGGACCCCACAAAGAACTAGACAGAAACTCATGCCAGT
901    ------+---------+---------+---------+---------+---------+ 960
       GCCCCGAAGCCGGACGGTCGACACCTGGGGTGTTCTTGATCTGTCTTTGAGTACGGTCA
           G  L  R  P  A  S  C  G  P  H  K  E  L  D  R  N  S  C  Q  C  -

GTGTCTGTAAAAACAAACTCTTCCCAGCCAATGTGGGCCAACCGAGAATTTGATGAAA
961    ------+---------+---------+---------+---------+---------+ 1020
       CACAGACATTTTTGTTTGAGAAGGGGTCGGTTACACCCCGGTTGGCTCTTAAACTACTTT
```

FIG. 1C

```
        V  C  K  N  K  L  F  P  S  Q  C  G  A  N  R  E  F  D  E  N  -
       ACACATGCCAGTGTAAAGAACCTGCCCCAGAAATCAACCCCTAAATCCTGGAA
1021   ------+---------+---------+---------+---------+---------+   1080
       TGTGTACGGTCACACATACATTTTCTTGGACGGGGTCTTTAGTTGGGGATTTAGGACCTT
        T  Q  Q  V  C  K  R  T  C  P  R  N  Q  P  L  N  P  G  K  -

AATGTGCCTGTGAATGTACAGAAAGTCCACAGAAATGCTTGTTAAAGGAAAGAAGTTCC
1081   ------+---------+---------+---------+---------+---------+   1140
       TTACACGGACACTTACATGTCTTTCAGGTGTCTTTACGAACAATTTCCTTTCTTCAAGG
        C  A  C  E  C  T  E  S  P  Q  K  C  L  L  K  G  K  K  F  H  -

ACCACCAAACATGCAGCTGTTACAGACGGCCATGTACGAACCGCCAGAAGGCTGTGAGC
1141   ------+---------+---------+---------+---------+---------+   1200
       TGGTGGTTTGTACGTCGACAATGTCTGCCGGTACATGCTTGGCGGTCTTCCGACACTCG
        H  Q  T  C  S  C  Y  R  R  P  C  T  N  R  Q  K  A  C  E  P  -

CAGGATTTTCATATAGTGAAGAAGTGTGTCGTTGTCCCTTCATATTGGCAAAGACCAC
1201   ------+---------+---------+---------+---------+---------+   1260
       GTCCTAAAAGTATATCACTTCTTCACACAGCAACAGGAAGTATAACCGTTTCTGGTG
        G  F  S  Y  S  E  E  V  C  R  C  V  P  S  Y  W  Q  R  P  Q  -

AAATGAGCTAAGATTGTACTGTTTCCAGTTCATCGATTTTCTATTATGGAAAACTGTGT
```

FIG. 1D

```
1261 ----------+---------+---------+---------+---------+---------+ 1320
     TTTACTCGATTCTAACATGACAAAAGGTCAAGTAGCTAAAGATAATACCTTTGACACA
                       M  S

1321 ----------+---------+---------+---------+---------+---------+ 1380
     TGCCACAGTAGAACTGTCTGTGAACAGAGAGACCCTTGTGGGTCCATGCTAACAAAGACA
     ACGGTGTCATCTTGACAGACACTTGTCTCTCTGGGAACACCCAGGTACGATTGTTTCTGT

1381 ----------+---------+---------+---------+---------+---------+ 1440
     AAAGTCTGTCTTCCTGAACCATGTGGATAACTTTACAGAAATGGACTGGAGCTCATCTG
     TTTCAGACAGAAGGACTTGGTACACCTATTGAAATGTCTTTACCTGACCTCGAGTAGAC

1441 ----------+---------+---------+---------+---------+---------+ 1500
     CAAAAGGCCTCTTGTAAAGACTGGTTTTCTGCCAATGACCAAACAGCCAAGATTTCCTC
     GTTTTCCGGAGAACATTTCTGACCAAAGACGGTTACTGGTTGTCGGTTCTAAAGGAG

1501 ----------+---------+---------+---------+---------+---------+ 1560
     TTGTGATTCTTTAAAGAATGACTATATAATTTATTCCACTAAAAATATTGTTTCTGC
     AACACTAAGAAATTTTCTACTGATATATTAAATAAGGTGATTTTATAACAAGACG

1561 ----------+---------+---------+---------+---------+---------+ 1620
     ATTCATTTTTATAGCAACAACAATTGGTAAAACTCACTGTGATCAATATTTTATATCAT
     TAAGTAAAAATATCGTTGTTGTTAACCATTTGAGTGACACTAGTTATAAAATATAGTA

1621 ----------+---------+---------+--- 1674
     GCAAAATATGTTTAAAATAATGAAAATTGTATTTATAAAAAAAAAAAA
     CGTTTTATACAAATTTTATTTACTTTAACATAAATATTTTTTTTTTTT
```

FIG.1E

```
  1 CGAGGCCACGGCTTATGCAAGCAAAGATCTGGAGGAGCAGTTACGGTCTGTGTCCAGTGT
    ------------+---------+---------+---------+---------+---------+

61 AGATGAACTCATGACTGTACTCTACCCAGAATATTGGAAAATGTACAAGTGTCAGCTAAG
    ------------+---------+---------+---------+---------+---------+
           M  T  V  L  Y  P  E  Y  W  K  M  Y  K  C  Q  L  R

121 GAAAGGAGGCTGGCAACATAACAGAGAACAGGCCAACCTCAACTCAAGGACAGAGAGAC
    ------------+---------+---------+---------+---------+---------+
       K  G  G  W  Q  H  N  R  E  Q  A  N  L  N  S  R  T  E  E  T

181 TATAAAATTGCTGCAGCACATTATAATACAGAGATCTTGAAAAGTATTGATAATGAGTG
    ------------+---------+---------+---------+---------+---------+
       I  K  F  A  A  A  H  Y  N  T  E  I  L  K  S  I  D  N  E  W

241 GAGAAAGACTCAATGCCATGCCACGGGAGGTGTGTATAGATGTGGGGAAGGAGTTTGGAGT
    ------------+---------+---------+---------+---------+---------+
       R  K  T  Q  C  M  P  R  E  V  C  I  D  V  G  K  E  F  G  V

301 CCGACAAACACCTTCTTTAAACCTCCATGTGTCCGTTCTACAGATGTGGGGTTGCTG
    ------------+---------+---------+---------+---------+---------+
       A  T  N  T  F  F  K  P  P  C  V  S  V  Y  R  C  G  G  C

FIG. 2A
```

```
361  CAATAGTGAGGGGCTGCAGTGCATGAACACCAGCACGAGCTACCTCAGCAAGACGTTATT
      N  S  E  G  L  Q  C  M  N  T  S  T  S  Y  L  S  K  T  L  F

421  TGAAATTACAGTGCCCTCTCTCAAGGCCCCCAAACCAGTAACAATCAGTTTGCCAATCA
      E  I  T  V  P  L  S  Q  G  P  K  P  V  T  I  S  F  A  N  H

481  CACTTCCTGCCGATGCATGTCTAAACTGGATGTTTACAGACAAGTTCATTCCATTATTAG
      T  S  C  R  C  M  S  K  L  D  V  Y  R  Q  V  H  S  I  I  R

541  ACGTTCCCTGCCAGCAACACTACCAGTGTCTCAGGCCAGCGAACAAGACCTGCCCCACCAA
      R  S  L  P  A  T  L  P  Q  C  Q  A  A  N  K  T  C  P  T  N

601  TTACATGTGGAATAATCACATCTGCAGATGCCTGGCTCAGGAAGATTTATGTTTTCCTC
      Y  M  W  N  N  H  I  C  R  C  L  A  Q  E  D  F  M  F  S  S

661  GGATGCTGGAGATGACTCAACAGATGGATTCCATGACATCTGTGGACCAAACAAGGAGCT
      D  A  G  D  D  S  T  D  G  F  H  D  I  C  G  P  N  K  E  L
```

FIG. 2B

```
 721  GGATGAAGAGACCTGTCAGTGTGTCTGCAGAGCGGGGGCTTCGGCCTGCCAGCTGTGGACC
       ---------+---------+---------+---------+---------+---------+
        D  E  E  T  C  Q  C  V  C  R  A  G  L  R  P  A  S  C  G  P

781  CCACAAAGAACTAGACAGAAACTCATGCCAGTGTGTCTGTAAAACAAACTCTTCCCCAG
       ---------+---------+---------+---------+---------+---------+
        H  K  E  L  D  R  N  S  C  Q  C  V  C  K  N  K  L  F  P  S

841  CCAATGTGGGCCAACCGAGAATTTGATGAAAACACACATGCCAGTGTGTATGTAAAGAAC
       ---------+---------+---------+---------+---------+---------+
        Q  C  G  A  N  R  E  F  D  E  N  T  C  Q  C  V  C  K  R  T

901  CTGCCCCAGAAATCAACCCCTAAATCCTGGAAATGTGCCTGTGAATGTACAGAAAGTCC
       ---------+---------+---------+---------+---------+---------+
        C  P  R  N  Q  P  L  N  P  G  K  C  A  C  E  C  T  E  S  P

961  ACAGAAATGCTTGTTAAAAGGAAAGAAGTTCCACCACCAAACATGCCAGCTGTTACAGACG
       ---------+---------+---------+---------+---------+---------+
        Q  K  C  L  L  K  G  K  K  F  H  H  Q  T  C  S  C  Y  R  R

1021  GCCATGTGTACGAACCGCCAGAAGGCTTGTGAGCCAGGATTTTCATATAGTGAAGAAGTGTG
       ---------+---------+---------+---------+---------+---------+
        P  C  T  N  R  Q  K  A  C  E  P  G  F  S  Y  S  E  E  V  C
```

FIG. 2C

```
1081  TCGTTGTGTCCCTTCATATTGGCAAAGACCACAAATGAGCTAAGATTGTACTGTTTCCA
       R   C   V   P   S   Y   W   Q   R   P   Q   M   S

1141  GTTCATCGATTTCTATTATGGAAAACTGTGTTGCCACAGTAGAACTGTCTGTGAACAGA

1201  GAGACCCTTGTGGGTCCATGCTAACAAAGACAAAGTCTGTCTTTCCTGAACCATGTGGA

1261  TAACTTTACAGAAATGGACTGGAGCTCATCTGCAAAAGGCCCTCTTGTAAAGACTGGTTT

1321  CTGCCCAATGACCAAACAGCCAAGATTTTCCTCTTGTGATTCTTTAAAAGAATGACTATA

1381  TAATTTATTCCACTAAAAATATGTTTCTGCATTCATTTTTATATCATGCAAAATATGTTTAAAATAAAATGAAAA

1441  AAAACTCACTGTGATCAATATTTTTATATCATGCAAAATATGTTTAAAATAAAATGAAAA

1501  TTGTATTATAAAAAAAAAAAAA
```

FIG. 2D

```
1                                                                        50
Pdgfa  .MRTLACLLL LGCGYLAHVL AEEAEIPREV IERLARSQIH SIRDLQRLLE
Pdgfb  MNRCWA LFL SLCCYLRLVS AEGDPIPEEL YEMLSDHSIR SFDDLQRLLH
Vegf   .....MNFLL SWVHWSLALL LY................. .LHHAKWSQA
Vegf2  ........MTV LYPEYWKMYK CQ.................. .LRKGGWQHN 51                                                                       100
Pdgfa  IDSVGSEDSL DTSLRAHGVH ATKHVPEKRP LPIRRKRSI. ......EEAVP
Pdgfb  GDP.GEEDGA ELDLNMTRSH SGGELES... .LARGRRSLG SLTIAEPAMI
Vegf   APMAE..... ......GGGQ NHHEVVKFMD .VYQR..... ..........
Vegf2  REQANLNSRT EETIKFAAAH YNTEILKSID NEWRK..... ..........

101                                                                      150
Pdgfa  AVCKTRTVIY EIPRSQVDPT SANFLIWPPC VEVKRCTGCC NTSSVKCQPS
Pdgfb  AECKTRTEVF EISRRLIDRT NANFLVWPPC VEVQRCSGCC NNRNVQCRPT
Vegf   SYCHPIETLV DIFQEYPDEI ..EYIFKPSC VPLMRCGGCC NDEGLECVPT
Vegf2  TQCMPREVCI DVGKEFGVAT ..NTFFKPPC VSVYRCGGCC NSEGLQCMNT 151                                                                      200
Pdgfa  RVHHRSVKVA KVEYVRKKPK LKEVQVRLEE HLECAC.... ......AT..
Pdgfb  QVQLRPVQVR KIEIVRKKPI FKKATVTLED HLACKC.... ETVAAARPVT
Vegf   EESNITMQIM RIK.PH..QC QHIGEMSFLQ HNKCECRPKK DRARQEKKSV
Vegf2  STSYLSKTLF EIT.VPLSQG PKPVTISFAN HTSCRCMSKL DVYRQVHSII
```

FIG. 3A

```
      201                                                             250
Pdgfa     TSLNPD YREEDTDVR. .......... .......... ..........
Pdgfb RSPGGSQEQR AKTPQTRVTI RTVRVRRPPK GKHRKFKHTH DKTALKETLG
Vegf  RGK....... .GKGQKRKRK KSRYKSWSVY VGARCCLMPW SLPGPHP...
Vegf2 RRSLPATLPQ CQAANKTCPT NYMWNNHICR CLAQEDFMFS SDAGDDSTDG 251                                                             300
Pdgfa ........ .......... .......... .......... ..........
Pdgfb A......CGP .......... .......... .......... ..........
Vegf  .......... .......... ....CSE RRKHLFVQDP QTCKCSCKNT
Vegf2 FHDICGPNKE LDEETCQCVC RAGLRPASCG PHKEL...DR NSCQCVCKNK 301                                                             350
Pdgfa .......... .......... .......... .......... ..........
Pdgfb .......... .......... .......... .......... ..........
Vegf  .DSRCKARQ LELNERTCRC DKPRR. .......... ..........
Vegf2 LFPSQCGANR EFDENTCQC VCKRTCPRNQ PLNPGKCACE CTESPQKCLL 351                                             398
Pdgfa .......... .......... .......... ........
Pdgfb .......... .......... .......... ........
Vegf  .......... .......... .......... ........
Vegf2 KGKKFHHQTC SCYRRPCTNR QKACEPGFSY SEEVCRCVPS YWQRPQMS
```

FIG. 3B

PERCENTAGE (%) OF AMINO ACID IDENTITIES BETWEEN EACH PAIR OF GENES IS SHOWN IN THE FOLLWING TABLE

| | PDGFα | PDGFβ | VEGF | VEGF2 |
|---|---|---|---|---|
| PDGFα | | | | |
| PDGFβ | 48.0 | | | |
| VEGF | 20.7 | 22.7 | | |
| VEGF2 | 23.5 | 22.4 | 30.0 | |

FIG. 4

Expression of VEGF2 mRNA in Human Breast Tumor Cells

Lane 1. normal breast tissue
Lane 2. breast tumor tissue
Lane 3-9. breast tumor cell lines.

Lane 1:   14-C and rainbow M.W. marker
Lane 2:   FGF control
Lane 3:   VEGF2 (M13-reverse $ forward primers)
Lane 4:   VEGF2 (M13-reverse & VEGF-F4 primers)
Lane 5:   VEGF2 (M13-reverse & VEGF-F5 primers)

Lane 1: Molelular weight marker
Lane 2: Precipitates containing VEGF2.

| | fetal kidney | fetal lung | fetal liver | brain | kidney | lung | liver | spleen | thymus | bone marrow | testes | placenta | skeletal muscle |
|---|---|---|---|---|---|---|---|---|---|---|---|---|---|
| | 1 | 2 | 3 | 4 | 5 | 6 | 7 | 8 | 9 | 10 | 11 | 12 | 13 |

◄ 2.4 kb VEGF-2

M B 1 2 3 4 5 6 7 8 9 10 11 12 13

◄ β-actin

1. Molecular Weight Marker
2. umbelical vein endothelial cells
3. aortic smooth muscle cells
4. Dermal fibroblast 1. m.w. marker
2. blank
3. control protein-HA
4. vector control
5. VEGF2-HA 1. m.w. marker
2. blank
3. control protein-HA
4. VEGF2-HA
5. vector control

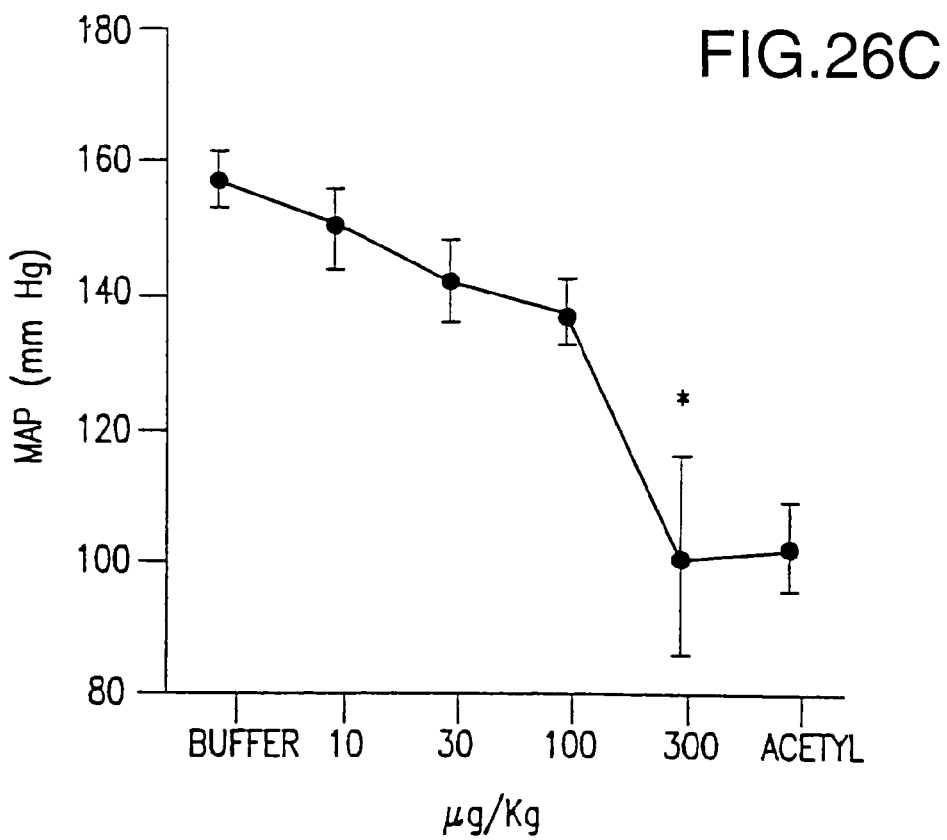
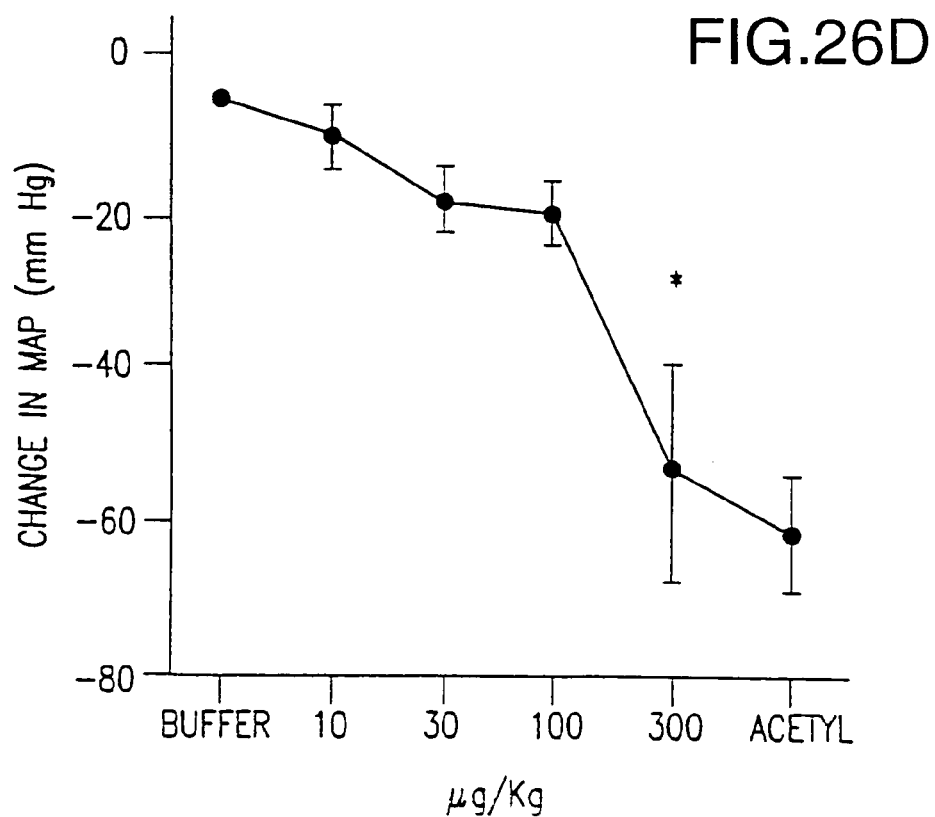

1 AAGCTTAAAAAAAACTGCAAAAATAGT TTGACT TGTGAGCGGATAAGAAT

-35

OPERATOR 1

50 TAAGAT GTACCCA ATTGTGAGCGGATAACAAT TTCACACATTAA

-10

OPERATOR 2

94 A AGAGGAG AAATTA CATATG

VASCULAR ENDOTHELIAL GROWTH FACTOR 2

CROSS-REFERENCE TO RELATED APPLICATIONS

This application is a divisional of U.S. application Ser. No. 09/935,726, filed Aug. 24, 2001, which is a continuation of U.S. application Ser. No. 09/438,538, filed Nov. 12, 1999 (now abandoned), which is a division of U.S. application Ser No. 09/042,105, filed Mar. 13, 1998 (now U.S. Pat. No. 6,040, 157, issued on Mar. 21, 2000), which is a continuation-in-part of U.S. application Ser. No. 08/999,811, filed Dec. 24, 1997 (now U.S. Pat. No. 5,932,540, issued on Aug. 3, 1999), which is a continuation-in-part of both U.S. application Ser. No. 08/465,968, filed Jun. 6, 1995 (now U.S. Pat. No. 6,608,182, issued on Aug. 19, 2003) and U.S. application Ser. No. 08/207,550, filed Mar. 8, 1994 (now abandoned), said U.S. application Ser. No. 08/465,968 is a continuation-in-part of U.S. application Ser. No. 08/207,550, filed Mar. 8, 1994 (now abandoned), all of which claim priority under 35 U.S.C. § 120, and all are hereby incorporated by reference in their entirety.

REFERENCE TO SEQUENCE LISTING ON COMPACT DISC

This application refers to a "Sequence Listing" listed below, which is provided as an electronic document on two identical compact discs (CD-R), labeled "Copy 1" and "Copy 2." These compact discs each contain the file "PF112P3D1C1D1 Seq List.txt" (41,192 bytes. created on Feb. 24, 2005), which is incorporated by reference in its entirety.

BACKGROUND OF THE INVENTION

1. Field of the Invention

The present invention relates to newly identified polynucleotides, polypeptides encoded by such polynucleotides, the use of such polynucleotides and polypeptides, as well as the production of such polynucleotides and polypeptides. The polypeptides of the present invention have been identified as members of the vascular endothelial growth factor family. More particularly, the polypeptides of the present invention are human vascular endothelial growth factor 2 (VEGF2). The invention also relates to inhibiting the action of such polypeptides.

2. Related Art

The formation of new blood vessels, or angiogenesis, is essential for embryonic development, subsequent growth, and tissue repair. Angiogenesis is also an essential part of certain pathological conditions, such as neoplasia (i.e., tumors and gliomas). Abnormal angiogenesis is associated with other diseases such as inflammation, rheumatoid arthritis, psoriasis, and diabetic retinopathy (Folkman, J. and Klagsbrun, M., Science 235:442-447 (1987)).

Both acidic and basic fibroblast growth factor molecules are mitogens for endothelial cells and other cell types. Angiotropin and angiogenin can induce angiogenesis, although their functions are unclear (Folkman, J., Cancer Medicine, Lea and Febiger Press, pp. 153-170 (1993)). A highly selective mitogen for vascular endothelial cells is vascular endothelial growth factor or VEGF (Ferrara, N. et al., Endocr. Rev. 13:19-32 (1992)), which is also known as vascular permeability factor (VPF).

Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifunctional regulator of endothelial cell growth and differentiation (Breier, G. et al., Development 114:521-532 (1992)).

VEGF shares sequence homology with human platelet-derived growth factors, PDGFα and PDGFβ (Leung, D. W., et al., Science 246:1306-1309, (1989)). The extent of homology is about 21% and 23%, respectively. Eight cysteine residues contributing to disulfide-bond formation are strictly conserved in these proteins. Although they are similar, there are specific differences between VEGF and PDGF. While PDGF is a major growth factor for connective tissue, VEGF is highly specific for endothelial cells. Alternatively spliced mRNAs have been identified for both VEGF, PLGF, and PDGF and these different splicing products differ in biological activity and in receptor-binding specificity. VEGF and PDGF function as homo-dimers or hetero-dimers and bind to receptors which elicit intrinsic tyrosine kinase activity following receptor dimerization.

VEGF has four different forms of 121, 165, 189 and 206 amino acids due to alternative splicing. VEGF121 and VEGF165 are soluble and are capable of promoting angiogenesis, whereas VEGF189 and VEGF206 are bound to heparin containing proteoglycans in the cell surface. The temporal and spatial expression of VEGF has been correlated with physiological proliferation of the blood vessels (Gajdusek, C. M., and Carbon, S. J., Cell Physiol. 139:570-579 (1989); McNeil, P. L., et al., J. Cell. Biol. 109:811-822 (1989)). Its high affinity binding sites are localized only on endothelial cells in tissue sections (Jakeman, L. B., et al., Clin. Invest. 89:244-253 (1989)). The factor can be isolated from pituitary cells and several tumor cell lines, and has been implicated in some human gliomas (Plate, K. H., Nature 359:845-848 (1992)). Interestingly, expression of VEGF121 or VEGF165 confers on Chinese hamster ovary cells the ability to form tumors in nude mice (Ferrara, N. et al., J. Clin. Invest. 91:160-170 (1993)). The inhibition of VEGF function by anti-VEGF monoclonal antibodies was shown to inhibit tumor growth in immune-deficient mice (Kim, K. J., Nature 362:841-844 (1993)). Further, a dominant-negative mutant of the VEGF receptor has been shown to inhibit growth of glioblastomas in mice.

Vascular permeability factor (VPF) has also been found to be responsible for persistent microvascular hyperpermeability to plasma proteins even after the cessation of injury, which is a characteristic feature of normal wound healing. This suggests that VPF is an important factor in wound healing. Brown, L. F. et al., J. Exp. Med. 176:1375-1379 (1992).

The expression of VEGF is high in vascularized tissues, (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sep. 30, 1992.

SUMMARY OF INVENTION

The polypeptides of the present invention have been putatively identified as a novel vascular endothelial growth factor based on amino acid sequence homology to human VEGF.

In accordance with one aspect of the present invention, there are provided novel mature polypeptides, as well as biologically active and diagnostically or therapeutically useful fragments, analogs, and derivatives thereof. The polypeptides of the present invention are of human origin.

In accordance with another aspect of the present invention, there are provided isolated nucleic acid molecules comprising polynucleotides encoding full length or truncated VEGF2 polypeptides having the amino acid sequences shown in SEQ ID NOS:2 or 4, respectively, or the amino acid sequences encoded by the cDNA clones deposited in bacterial hosts as ATCC Deposit Number 97149 on May 12, 1995 or ATCC Deposit Number 75698 on Mar. 4, 1994

The present invention also relates to biologically active and diagnostically or therapeutically useful fragments, analogs, and derivatives of VEGF2.

In accordance with still another aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said proteins and subsequent recovery of said proteins.

In accordance with yet a further aspect of the present invention, there are provided processes for utilizing such polypeptides, or polynucleotides encoding such polypeptides for therapeutic purposes, for example, to stimulate angiogenesis, wound-healing, growth of damaged bone and tissue, and to promote vascular tissue repair.

In accordance with yet another aspect of the present invention, there are provided antibodies against such polypeptides and processes for producing such polypeptides.

In accordance with yet another aspect of the present invention, there are provided antagonists to such polypeptides, which may be used to inhibit the action of such polypeptides, for example, to prevent tumor angiogenesis and thus inhibit the growth of tumors, to treat diabetic retinopathy, inflammation, rheumatoid arthritis and psoriasis.

In accordance with another aspect of the present invention, there are provided nucleic acid probes comprising nucleic acid molecules of sufficient length to specifically hybridize to nucleic acid sequences of the present invention.

In accordance with another aspect of the present invention, there are provided methods of diagnosing diseases or a susceptibility to diseases related to mutations in nucleic acid sequences of the present invention and proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A-1E show the full length nucleotide (SEQ ID NO:1) and the deduced amino acid (SEQ ID NO:2) sequence of VEGF2. The polypeptide comprises approximately 419 amino acid residues of which approximately 23 represent the leader sequence. The standard one letter abbreviations for amino acids are used. Sequencing was performed using the Model 373 Automated DNA Sequencer (Applied Biosystems, Inc.). Sequencing accuracy is predicted to be greater than 97%.

FIGS. 2A-2D show the nucleotide (SEQ ID NO:3) and the deduced amino acid (SEQ ID NO:4) sequence of a truncated, biologically active form of VEGF2. The polypeptide comprises approximately 350 amino acid residues of which approximately the first 24 amino acids represent the leader sequence.

FIGS. 3A-3B are an illustration of the amino acid sequence homology between PDGFα (SEQ ID NO:5), PDGFβ (SEQ ID NO:6), VEGF (SEQ ID NO:7), and VEGF2 (SEQ ID NO:4). The boxed areas indicate the conserved sequences and the location of the eight conserved cysteine residues.

FIG. 4 shows, in table-form, the percent homology between PDGFα, PDGFβ, VEGF, and VEGF2.

FIGS. 26A-G depicts ability of VEGF2 to affect the diastolic blood pressure in spontaneously hypertensive rats (SHR). FIGS. 26$a$ and $b$ depict the dose-dependent decrease in diastolic blood pressure achieved with VEGF2. (FIGS. 26$c$ and $d$ depict the decreased mean arterial pressure (MAP) observed with VEGF2. Panel E shows the effect of increasing doses of VEGF-2 on the mean arterial pressure (MAP) of SHR rats. Panel F shows the effect of VEGF-2 on the diastolic pressure of SHR rats. Panel G shows the effect of VEGF-2 on the diastolic blood pressure of SHR rats.

FIG. 29 shows the nucleotide sequence of the regulatory elements of the pHE4a promoter (SEQ ID NO:17). The two lac operator sequences, the Shine-Delgarno sequence (S/D), and the terminal HindIII and NdeI restriction sites (italicized) are indicated.

DETAILED DESCRIPTION OF THE PREFERRED EMBODIMENTS

Figure 5:
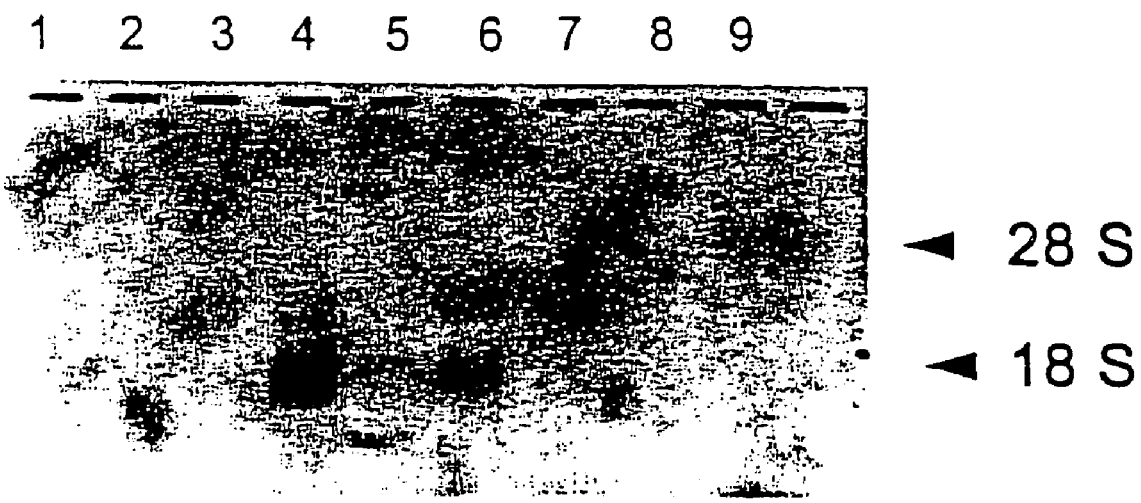
FIG. 5 shows the presence of VEGF2 mRNA in human breast tumor cell lines.

In accordance with one aspect of the present invention, there are provided isolated nucleic acid molecules comprising a polynucleotide encoding a VEGF2 polypeptide having the deduced amino acid sequence of FIG. 1 (SEQ ID NO:2), which was determined by sequencing a cloned cDNA. The nucleotide sequence shown in SEQ ID NO: 1 was obtained by sequencing a cDNA clone, which was deposited on May 12, 1995 at the American Type Culture Collection (ATCC), Patent Depository, 10801 University Boulevard, Manassas, Va. 20110-2209, and given ATCC Deposit No. 97149.

In accordance with another aspect of the present invention, there are provided isolated nucleic acid molecules comprising a polynucleotide encoding a truncated VEGF2 polypeptide having the deduced amino acid sequence of FIG. 2 (SEQ ID NO:4), which was determined by sequencing a cloned cDNA. The nucleotide sequence shown in SEQ ID NO:3 was obtained by sequencing a cDNA clone, which was deposited on Mar. 4, 1994 at the American Type Culture Collection (ATCC), Patent Depository, 10801 University Boulevard, Manassas, Va. 20110-2209, and given ATCC Deposit Number 75698.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 419 amino acid residues of which approximately the first 23 amino acid residues are the putative leader sequence such that the mature protein comprises 396 amino acids, and which protein exhibits the highest amino acid sequence homology to human vascular endothelial growth factor (30% identity), followed by PDGFα (24%) and PDGFβ (22%). (See FIG. 4). It is particularly important that all eight cysteines are conserved within all four members of the family (see boxed areas of FIG. 3). In addition, the signature for the PDGF/VEGF family, PXCVXXXRCXGCCN, (SEQ ID NO: 8) is conserved in VEGF2 (see FIG. 3). The homology between VEGF2, VEGF and the two PDGFs is at the protein sequence level. No nucleotide sequence homology can be detected, and therefore, it would be difficult to isolate the VEGF2 through simple approaches such as low stringency hybridization.

The VEGF2 polypeptide of the present invention is meant to include the full length polypeptide and polynucleotide sequence which encodes for any leader sequences and for active fragments of the full length polypeptide. Active fragments are meant to include any portions of the full length amino acid sequence which have less than the full 419 amino acids of the full length amino acid sequence as shown in SEQ ID NO:2, but still contain the eight cysteine residues shown conserved in FIG. 3 and that still have VEGF2 activity.

There are at least two alternatively spliced VEGF2 mRNA sequences present in normal tissues. The two bands in FIG. 7, lane 5 indicate the presence of the alternatively spliced mRNA encoding the VEGF2 polypeptide of the present invention.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or FIG. 2, or that of the deposited clones, or may be a different coding sequence which, as a result of the redundancy or degeneracy of the genetic code, encodes the same, mature polypeptide as the DNA of FIG. 1, FIG. 2, or the deposited cDNAs.

The polynucleotide which encodes for the mature polypeptide of FIG. 1 or FIG. 2 or for the mature polypeptides encoded by the deposited cDNAs may include: only the coding sequence for the mature polypeptide; the coding sequence for the mature polypeptide and additional coding sequences such as a leader or secretory sequence or a proprotein sequence; the coding sequence for the mature polypeptide (and optionally additional coding sequences) and non-coding sequences, such as introns or non-coding sequence 5' and/or 3' of the coding sequence for the mature polypeptide.

Thus, the term "polynucleotide encoding a polypeptide" encompasses a polynucleotide which includes only coding sequences for the polypeptide as well as a polynucleotide which includes additional coding and/or non-coding sequences.

The present invention further relates to variants of the hereinabove described polynucleotides which encode for fragments, analogs and derivatives of the polypeptide having the deduced amino acid sequence of FIG. 1 or 2, or the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or 2 or the same mature polypeptide encoded by the cDNA of the deposited clones as well as variants of such polynucleotides which variants encode for a fragment, derivative, or analog of the polypeptides of FIG. 1 or 2, or the polypeptide encoded by the cDNA of the deposited clones. Such nucleotide variants include deletion variants, substitution variants, and addition or insertion variants.

As hereinabove indicated, the polynucleotide may have a coding sequence which is a naturally occurring allelic variant of the coding sequence shown in FIG. 1 or 2, or of the coding sequence of the deposited clones. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell 37:767 (1984)).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 396 in SEQ ID NO:2; (d) a nucleotide sequence encoding the polypeptide having the amino acid sequence encoded by the cDNA clone contained in ATCC Deposit No. 97149; (e) a nucleotide sequence encoding the mature VEGF2 polypeptide having the amino acid sequence encoded by the cDNA clone contained in ATCC Deposit No. 97149; or (f) a nucleotide sequence complementary to any of the nucleotide sequences in (a), (b), (c), (d), or (e).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:4; (b) a nucleotide sequence encoding the polypeptide having the amino acid sequence in SEQ ID NO:4, but lacking the N-terminal methionine; (c) a nucleotide sequence encoding the polypeptide having the amino acid sequence at positions from about 1 to about 326 in SEQ ID NO:4; (d) a nucleotide sequence encoding the polypeptide having the amino acid sequence encoded by the cDNA clone contained in ATCC Deposit No. 75698; (e) a nucleotide sequence encoding the mature VEGF2 polypeptide having the amino acid sequence encoded by the cDNA clone contained in ATCC Deposit No. 75698; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a VEGF2 polypeptide is intended that the nucleotide sequence of the polynucleotide is identical to the reference sequence except that the polynucleotide sequence may include up to five point mutations per each 100 nucleotides of the reference nucleotide sequence encoding the VEGF2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NOS:1 or 3, or to the nucleotides sequence of the deposited cDNA clone(s) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As described in detail below, the polypeptides of the present invention can be used to raise polyclonal and monoclonal antibodies, which are useful in diagnostic assays for detecting VEGF-2 protein expression as described below or as agonists and antagonists capable of enhancing or inhibiting VEGF-2 protein function. Further, such polypeptides can be used in the yeast two-hybrid system to "capture" VEGF-2 protein binding proteins which are also candidate agonist and antagonist according to the present invention. The yeast two hybrid system is described in Fields and Song, Nature 340: 245-246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic e epitopes. See, for instance, Geysen et al., Proc. Natl. Acad. Sci. USA 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., Cell 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate VEGF-2-specific antibodies include the following: a polypeptide comprising amino acid residues from about leu-37 to about glu-45 in SEQ ID NO:2, from about Tyr-58 to about Gly-66 in SEQ ID NO:2, from about Gln-73 to about Glu-81 in SEQ ID NO:2, from about Asp-100 to about Cys-108 in SEQ ID NO:2, from about Gly-140 to about Leu-148 in SEQ ID NO:2, from about Pro-168 to about Val-176 in SEQ ID NO:2, from about His-183 to about Lys-191 in SEQ ID NO:2, from about Ile-201 to about Thr-209 in SEQ ID NO:2, from about Ala-216 to about Tyr-224 in SEQ ID NO:2, from about Asp-244 to about His-254 in SEQ ID NO:2, from about Gly-258 to about Glu-266 in SEQ ID NO:2, from about Cys-272 to about Ser-280 in SEQ ID NO:2, from about Pro-283 to about Ser-291 in SEQ ID NO:2, from about Cys-296 to about Gln-304 in SEQ ID NO:2, from about Ala-307 to about Cys-316 in SEQ ID NO:2, from about Val-319 to about Cys-335 in SEQ ID NO:2, from about Cys-339 to about Leu-347 in SEQ ID NO:2, from about Cys-360 to about Glu-373 in SEQ ID NO:2, from about Tyr-378 to about Val-386 in SEQ ID NO:2, and from about Ser-388 to about Ser-396 in SEQ ID NO:2. These polypeptide fragments have been determined to bear antigenic epitopes of the VEGF-2 protein by the analysis of the Jameson-Wolf antigenic index.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131-5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general lining agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, VEGF-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)).

In accordance with the present invention, novel variants of VEGF-2 are also described. These can be produced by deleting or substituting one or more amino acids of VEGF-2. Natural mutations are called allelic variations. Allelic variations can be silent (no change in the encoded polypeptide) or may have altered amino acid sequence.

In order to attempt to improve or alter the characteristics of native VEGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

Amino Terminal and Carboxy Terminal Deletions

Figure 6:
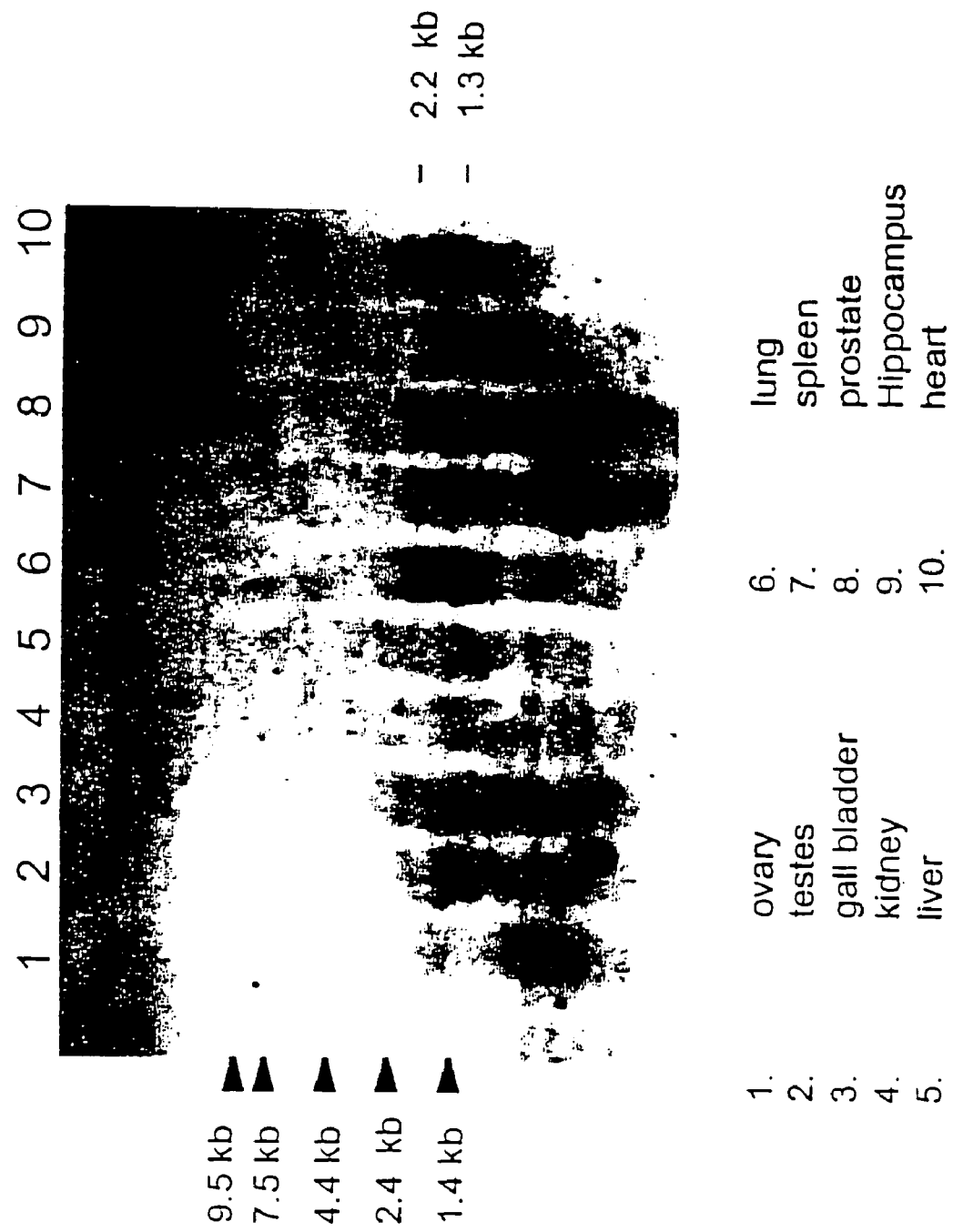
FIG. 6 depicts the results of a Northern blot analysis of VEGF2 in human adult tissues.

Furthermore, VEGF-2 appears to be proteolytically cleaved upon expression resulting in polypeptide fragments of the following sizes when run on a SDS-PAGE gel (sizes are approximate) (See, FIGS. 6-8, for example): 80, 59, 45, 43, 41, 40, 39, 38, 37, 36, 31, 29, 21, and 15 kDa These polypeptide fragments are the result of proteolytic cleavage at both the N-terminal and C-terminal portions of the protein. These proteolytically generated fragments appears to have activity, particularly the 21 kDa fragment.

In addition, protein engineering may be employed in order to improve or alter one or more characteristics of native VEGF-2. The deletion of carboxyterminal amino acids can enhance the activity of proteins. One example is interferon gamma that shows up to ten times higher activity by deleting ten amino acid residues from the carboxy terminus of the protein (Döbeli et al., J. of Biotechnology 7:199-216 (1988)). Thus, one aspect of the invention is to provide polypeptide analogs of VEGF-2 and nucleotide sequences encoding such analogs that exhibit enhanced stability (e.g., when exposed to typical pH, thermal conditions or other storage conditions) relative to the native VEGF-2 polypeptide.

Particularly preferred VEGF-2 polypeptides are shown below (numbering starts with the first amino acid in the protein (Met) (FIG. 1 (SEQ ID NO: 18)):

| | |
|---|---|
| Ala(residue 24)-Ser(residue 419) | Glu(32)-Ser(419) |
| Pro(25)-Ser(419) | Ser(33)-Ser(419) |
| Ala(26)-Ser(419) | Gly(34)-Ser(419) |
| Ala(27)-Ser(419) | Leu(35)-Ser(419) |
| Ala(28)-Ser(419) | Asp(36)-Ser(419) |
| Ala(29)-Ser(419) | Leu(37)-(Ser(419)) |
| Ala(30)-Ser(419) | Ser(38)-Ser(419) |
| Phe(31)-Ser(419) | Asp(39)-Ser(419) |
| | Ala(40)-Ser(419) |
| Glu(41)-Ser(419) | Met(1), Glu(23), or Ala(24)-Gln(414) |
| Pro(42)-Ser(419) | Met(1), Glu(23), or Ala(24)-Trp(413) |
| Asp(43)-Ser(419) | Met(1), Glu(23), or Ala(24)-Tyr(412) |
| Ala(44)-Ser(419) | Met(1), Glu(23), or Ala(24)-Ser(411) |
| Gly(45)-Ser(419) | Met(1), Glu(23), or Ala(24)-Pro(410) |
| Glu(46)-Ser(419) | Met(1), Glu(23), or Ala(24)-Val(409) |
| Ala(47)-Ser(419) | Met(1), Glu(23), or Ala(24)-Cys(408) |
| Thr(48)-Ser(419) | Met(1), Glu(23), or Ala(24)-Arg(407) |
| Ala(49)-Ser(419) | Met(1), Glu(23), or Ala(24)-Cys(406) |
| Tyr(50)-Ser(419) | Met(1), Glu(23), or Ala(24)-Val(405) |
| Ser(52)-Ser(419) | Met(1), Glu(23), or Ala(24)-Glu(404) |
| Asp(54)-Ser(419) | Met(1), Glu(23), or Ala(24)-Glu(403) |
| Val(62)-Ser(419) | Met(1), Glu(23), or Ala(24)-Ser(402) |
| Val(65)-Ser(419) | Met(1), Glu(23), or Ala(24)-Gly(398) |
| Met(1), Glu(23), or Ala(24)-Met(418) | Met(1), Glu(23), or Ala(24)-Pro(397) |
| Met(1), Glu(23), or Ala(24)-Gln(417) | Met(1), Glu(23), or Ala(24)-Lys(393) |
| Met(1), Glu(23), or Ala(24)-Pro(416) | Met(1), Glu(23), or Ala(24)-Met(263) |
| Met(1), Glu(23), or Ala(24)-Arg(415) | |
| Met(1), Glu(23), or Ala(24)-Asp(311) | Tyr(114)-Ser(228) |
| Met(1), Glu(23), or Ala(24)-Pro(367) | Asn(115)-Ser(228) |
| Met(1)-Ser(419) | Thr(116)-Ser(228) |
| Met(1)-Ser(228) | Thr(103)-Leu(229) |
| Glu(47)-Ser(419) | Glu(104)-Leu(229) |
| Ala(111)-Lys(214) | Thr(103)-Arg(227) |
| Ala(112)-Lys(214) | Glu(104)-Arg(227) |
| His(113)-Lys(214) | Glu(105)-Arg(227) |
| Tyr(114)-Lys(214) | Thr(106)-Arg(227) |
| Asn(115)-Lys(214) | Ile(107)-Arg(227) |
| Thr(116)-Lys(214) | Lys(108)-Arg(227) |
| Thr(103)-Leu(215) | Phe(109)-Arg(227) |
| Glu(104)-Leu(215) | Ala(110)-Arg(227) |
| Glu(105)-Leu(215) | Ala(111)-Arg(227) |
| Thr(106)-Leu(215) | Ala(112)-Arg(227) |
| Ile(107)-Leu(215) | His(113)-Arg(227) |
| Lys(108)-Leu(215) | Tyr(114)-Arg(227) |
| Phe(109)-Leu(215) | Asn(115)-Arg(227) |
| Ala(110)-Leu(215) | Thr(116)-Arg(227) |
| Ala(111)-Leu(215) | Thr(103)-Ser(213) |
| Ala(112)-Leu(215) | Glu(104)-Ser(213) |
| His(113)-Leu(215) | Glu(105)-Ser(213) |
| Tyr(114)-Leu(215) | Thr(106)-Ser(213) |
| Asn(115)-Leu(215) | Ile(107)-Ser(213) |
| Thr(116)-Leu(215) | Lys(108)-Ser(213) |
| Thr(103)-Ser(228) | Phe(109)-Ser(213) |
| Glu(104)-Ser(228) | Ala(110)-Ser(213) |
| Glu(105)-Ser(228) | Ala(111)-Ser(213) |
| Thr(106)-Ser(228) | Ala(112)-Ser(213) |
| Ile(107)-Ser(228) | His(113)-Ser(213) |
| Lys(108)-Ser(228) | Tyr(114)-Ser(213) |
| Phe(109)-Ser(228) | Asn(115)-Ser(213) |
| Ala(110)-Ser(228) | Thr(116)-Ser(213) |
| Ala(111)-Ser(228) | Thr(103)-Lys(214) |
| Ala(112)-Ser(228) | Glu(104)-Lys(214) |
| His(113)-Ser(228) | Glu(105)-Lys(214) |
| Thr(106)-Lys(214) | |
| Ile(107)-Lys(214) | |
| Lys(108)-Lys(214) | |
| Phe(109)-Lys(214) | |
| Ala(110)-Lys(214) | |
| Glu(105)-Leu(229) | |
| Thr(106)-Leu(229) | |
| Ile(107)-Leu(229) | |
| Lys(108)-Leu(229) | |
| Phe(109)-Leu(229) | |
| Ala(110)-Leu(229) | |
| Ala(111)-Leu(229) | |
| Ala(112)-Leu(229) | |
| His(113)-Leu(229) | |
| Tyr(114)-Leu(229) | |
| Asn(115)-Leu(229) | |
| Thr(116)-Leu(229) | |

Preferred embodiments include the following deletion mutants: Thr(103)-Arg(227); Glu(104)-Arg(227); Ala(112)-Arg (227); Thr(103)-Ser(213); Glu(104)-Ser(213); Thr(103)-Leu(215); Glu(47)-Ser(419); Met(1), Glu (23), or Ala (24)-Met(263); Met(1), Glu (23), or Ala (24)-Asp(311); Met(1), Glu (23), or Ala (24)-Pro (367); Met(1)-Ser(419); and Met (1)-Ser(228) of FIG. 1 (SEQ ID NO:18)).

Also included by the present invention are deletion mutants having amino acids deleted from both the N terminus and the C-terminus. Such mutants include all combinations of the N-terminal deletion mutants and C-terminal deletion mutants described above. Those combinations can be made using recombinant techniques known to those skilled in the art.

Thus, in one aspect, N-terminal deletion mutants are provided by the present invention. Such mutants include those comprising the amino acid sequence shown in FIG. 1 (SEQ ID NO: 18) except for a deletion of at least the first 24 N-terminal amino acid residues (i.e., a deletion of at least Met (1)-Glu (24)) but not more than the first 115 N-terminal amino acid residues of FIG. 1 (SEQ ID NO: 18). Alternatively, first 24 N-terminal amino acid residues (i.e., a deletion of at least Met (1)-Glu (24)) but not more than the first 103 N-terminal amino acid residues of FIG. 1 (SEQ ID NO: 18),etc, etc.

In another aspect, C-terminal deletion mutants are provided by the present invention. Such mutants include those comprising the amino acid sequence shown in FIG. 1 (SEQ ID NO: 18) except for a deletion of at least the last C-terminal amino acid residue (Ser (419)) but not more than the last 220

C-terminal amino acid residues (i.e., a deletion of amino acid residues Val (199)-Ser (419)) of FIG. 1 (SEQ ID NO:18). Alternatively, the deletion will include at least the last C-terminal amino acid residue but not more than the last 216 C-terminal amino acid residues of FIG. 1 (SEQ ID NO:18). Alternatively, the deletion will include at least the last C-terminal amino acid residue but not more than the last 204 C-terminal amino acid residues of FIG. 1 (SEQ ID NO:18). Alternatively, the deletion will include at least the last C-terminal amino acid residues but not more than the last 192 C-terminal amino acid residues of FIG. 1 (SEQ ID NO: 18). Alternatively, the deletion will include at least the last C-terminal amino acid residues but not more than the last 156 C-terminal amino acid residues of FIG. 1 (SEQ ID NO:18). Alternatively, the deletion will include at least the last C-terminal amino acid residues but not more than the last 108 C-terminal amino acid residues of FIG. 1 (SEQ ID NO:18). Alternatively, the deletion will include at least the last C-terminal amino acid residues but not more than the last 52 C-terminal amino acid residues of FIG. 1 (SEQ ID NO:18).

In yet another aspect, also included by the present invention are deletion mutants having amino acids deleted from both the N-terminal and C-terminal residues. Such mutants include all combinations of the N-terminal deletion mutants and C-terminal deletion mutants described above.

The term "gene" means the segment of DNA involved in producing a polypeptide chain; it includes regions preceding and following the coding region (leader and trailer) as well as intervening sequences (introns) between individual coding segments (exons).

The present invention is further directed to fragments of the isolated nucleic acid molecules described herein. By a fragment of a isolated nucleic acid molecule having the nucleotide sequence of the deposited cDNA(s) or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650 or 1674 nt in length are also useful according to the present invention as are fragments corresponding to most, if not all, of the nucleotide sequence of the deposited cDNA(s) or as shown in SEQ ID NO: 1 or SEQ ID NO:3. By a fragment at least 20 nt in length, for example, is intended fragments which include 20 or more contiguous bases from the nucleotide sequence of the deposited cDNA(s) or the nucleotide sequence as shown in SEQ ID NOS:1 or 3.

Moreover, representative examples of VEGF2 polynucleotide fragments include, for example, fragments having a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950-, or 951 to the end of SEQ ID NO:1 or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

A VEGF2 "polynucleotide" also includes those polynucleotides capable of hybridizing, under stringent hybridization conditions, to sequences contained in SEQ ID NO: 1 or for instance, the cDNA clone(s) contained in ATCC Deposit Nos. 97149 or 75698, the complement thereof. "Stringent hybridization conditions" refers to an overnight incubation at 42° C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the VEGF2 polynucleotides at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g. the deposited cDNA or the nucleotide sequence as shown in SEQ ID NO:1). Of course, a polynucleotide which hybridizes only to a poly A sequence (such as the 3' terminal poly(A) tract of the VEGF2 cDNA shown in SEQ ID NOS:1 or 3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The present application is directed to nucleic acid molecules at least 95%, 96%, 97%, 98% or 99% identical to the nucleic acid sequence shown in SEQ ID NOS:1 or 3 or to the nucleic acid sequence of the deposited cDNA(s), irrespective of whether they encode a polypeptide having VEGF2 activity. This is because even where a particular nucleic acid molecule does not encode a polypeptide having VEGF2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having VEGF2 activity include, inter alia, (1) isolating the VEGF2 gene or allelic variants thereof in a cDNA library; (2) in situ hybridization (e.g., "FISH") to metaphase chromosomal spreads to provide precise chromosomal location of the VEGF2 gene, as described in Verma et al., Human Chromosomes: A Manual of Basic Techniques, Pergamon Press, New York (1988); and Northern Blot analysis for detecting VEGF2 mRNA expression in specific tissues.

Preferred, however, are nucleic acid molecules having sequences at least 95%, 96%, 97%, 98% or 99% identical to a nucleic acid sequence shown in SEQ ID NOS:1 or 3 or to a nucleic acid sequence of the deposited cDNA(s) which do, in fact, encode a polypeptide having VEGF2 protein activity. By "a polypeptide having VEGF2 activity" is intended polypeptides exhibiting VEGF2 activity in a particular biological assay. For example, VEGF2 protein activity can be measured using, for example, mitogenic assays and endothelial cell migration assays. See, e.g., Olofsson et al., Proc. Natl. Acad Sci. USA 93:2576-2581 (1996) and Joukov et al., EMBO J. 5:290-298 (1996).

Of course, due to the degeneracy of the genetic code, one of ordinary skill in the art will immediately recognize that a large number of the nucleic acid molecules having a sequence at least 90%, 95%, 96%, 97%, 98%, or 99% identical to a nucleic acid sequence of the deposited cDNA(s) or the nucleic acid sequence shown in SEQ ID NO:1 or SEQ ID NO:3 will encode a polypeptide "having VEGF2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having VEGF2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990), wherein the authors indicate that proteins are surprisingly tolerant of amino acid substitutions.

Thus, the present invention is directed to polynucleotides having at least a 70% identity, preferably at least 90% and more preferably at least a 95%, 96%, 97%, or 98% identity to a polynucleotide which encodes the polypeptides of SEQ ID NOS:2 or 4, as well as fragments thereof, which fragments have at least 30 bases and preferably at least 50 bases and to polypeptides encoded by such polynucleotides.

"Identity" per se has an art-recognized meaning and can be calculated using published techniques. (See, e.g.: COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991).) While there exists a number of methods to measure identity between two polynucleotide or polypeptide sequences, the term "identity" is well known to skilled artisans. (Carillo, H., and Lipton, D., SIAM J Applied Math 48:1073 (1988).) Methods commonly employed to determine identity or similarity between two sequences include, but are not limited to, those disclosed in Guide to Huge Computers, Martin J. Bishop, ed., Academic Press, San Diego, (1994), and Carillo, H., and Lipton, D., SIAM J Applied Math 48:1073 (1988). Methods for aligning polynucleotides or polypeptides are codified in computer programs, including the GCG program package (Devereux, J., et al., Nucleic Acids Research (1984) 12(1):387 (1984)), BLASTP, BLASTN, FASTA (Atschul, S. F. et al., J. Molec. Biol. 215:403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, Advances in Applied Mathematics 2:482-489 (1981).)

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the VEGF2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence SEQ ID NO: 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not-matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

VEGF-2 Polypeptides

The present invention further relates to polypeptides which have the deduced amino acid sequence of FIG. 1 or 2, or which has the amino acid sequence encoded by the deposited cDNAs, as well as fragments, analogs, and derivatives of such polypeptides.

The terms "fragment," "derivative" and "analog" when referring to the polypeptide of FIG. 1 or 2 or that encoded by the deposited cDNA, means a polypeptide which retains the conserved motif of VEGF proteins as shown in FIG. 3 and essentially the same biological function or activity.

In the present invention, a "polypeptide fragment" refers to a short amino acid sequence contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1-20, 21-40, 41-60, 61-80, 81-100, 102-120, 121-140, 141-160, 161-180, 181-200, 201-220, 221-240, 241-260, 261-280, or 281 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted VEGF2 protein as well as the mature form. Further preferred polypeptide fragments include the secreted VEGF2 protein or the mature form having a continuous series of deleted residues from the amino or the carboxy terminus, or both. For example, any number of amino acids, ranging from 1-60, can be deleted from the amino terminus of either the secreted VEGF2 polypeptide or the mature form. Similarly, any number of amino acids, ranging from 1-30, can be deleted from the carboxy terminus of the secreted VEGF2 protein or mature form. Furthermore, any combination of the above amino and carboxy terminus deletions are preferred. Similarly, polynucleotide fragments encoding these VEGF2 polypeptide fragments are also preferred.

Also preferred are VEGF2 polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. (See FIG. 2.) Moreover, polynucleotide fragments encoding these domains are also contemplated.

Other preferred fragments are biologically active VEGF2 fragments. Biologically active fragments are those exhibiting activity similar, but not necessarily identical, to an activity of the VEGF2 polypeptide. The biological activity of the fragments may include an improved desired activity, or a decreased undesirable activity.

The polypeptides of the present invention may be recombinant polypeptides, natural polypeptides, or synthetic polypeptides, preferably recombinant polypeptides.

It will be recognized in the art that some amino acid sequences of the VEGF2 polypeptide can be varied without significant effect of the structure or function of the protein. If such differences in sequence are contemplated, it should be remembered that there will be critical areas on the protein which determine activity.

Thus, the invention further includes variations of the VEGF2 polypeptide which show substantial VEGF2 polypeptide activity or which include regions of VEGF2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," Science 247:1306-1310 (1990).

Thus, the fragments, derivatives, or analogs of the polypeptides of FIG. 1 or 2, or that encoded by the deposited cDNAs may be: (I) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence; or (v) one in which comprises fewer amino acid residues shown in SEQ ID NOS: 2 or 4, and retains the conserved motif and yet still retains activity characteristics of the VEGF family of polypeptides. Such fragments, derivatives, and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the VEGF2 protein. The prevention of aggregation is highly desirable. Aggregation of proteins not only results in a loss of activity but can also be problematic when preparing pharmaceutical formulations, because they can be immunogenic. (Pinckard et al., Clin. Exp. Immunol. 2:331-340 (1967); Robbins et al., Diabetes 36:838-845 (1987); Cleland et al. Crit. Rev. Therapeutic Drug Carrier Systems 10:307-377 (1993)).

The replacement of amino acids can also change the selectivity of binding to cell surface receptors. Ostade et al., Nature 361:266-268 (1993) describes certain mutations resulting in selective binding of TNF-α to only one of the two known types of TNF receptors. Thus, the VEGF2 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions | |
|---|---|
| Aromatic | Phenylalanine<br>Tryptophan<br>Tyrosine |

TABLE 1-continued Conservative Amino Acid Substitutions

| | |
|---|---|
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given VEGF-2 polypeptide will not be more than 50, 40, 30, 25, 20, 15, 10, 5 or 3.

Amino acids in the VEGF2 protein of the present invention that are essential for function can be identified by methods known in the art, such as site-directed mutagenesis or alanine-scanning mutagenesis (Cunningham and Wells, Science 244: 1081-1085 (1989)), The later procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photo affinity labeling (Smith et al., J. Mol. Biol. 224:899-904 (1992) and de Vos et al. Science 255:306-312 (1992)).

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The polypeptides of the present invention include the polypeptides of SEQ ID NOS:2 and 4 (in particular the mature polypeptide) as well as polypeptides which have at least 70% similarity (preferably at least 70% identity) to the polypeptides of SEQ ID NOS:2 and 4, and more preferably at least 90% similarity (more preferably at least 95% identity) to the polypeptides of SEQ ID NOS:2 and 4, and still more preferably at least 95% similarity (still more preferably at least 90% identity) to the polypeptides of SEQ ID NOS:2 and 4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The polypeptides of the present invention include the polypeptide encoded by the deposited cDNA including the leader; the mature polypeptide encoded by the deposited the cDNA minus the leader (i.e., the mature protein); a polypeptide comprising amino acids about −23 to about 396 in SEQ ID NO:2; a polypeptide comprising amino acids about −22 to about 396 in SEQ ID NO:2; a polypeptide comprising amino acids about 1 to about 396 in SEQ ID NO:2; as well as polypeptides which are at least 95% identical, and more preferably at least 96%, 97%, 98% or 99% identical to the polypeptides described above and also include portions of such polypeptides with at least 30 amino acids and more preferably at least 50 amino acids.

Fusion Proteins

Any VEGF2 polypeptide can be used to generate fusion proteins. For example, the VEGF2 polypeptide, when fused to a second protein, can be used as an antigenic tag. Antibodies raised against the VEGF2 polypeptide can be used to indirectly detect the second protein by binding to the VEGF2. Moreover, because secreted proteins target cellular locations based on trafficking signals, the VEGF2 polypeptides can be used as a targeting molecule once fused to other proteins.

Examples of domains that can be fused to VEGF2 polypeptides include not only heterologous signal sequences, but also other heterologous functional regions. The fusion does not necessarily need to be direct, but may occur through linker sequences.

Moreover, fusion proteins may also be engineered to improve characteristics of the VEGF2 polypeptide. For instance, a region of additional amino acids, particularly charged amino acids, may be added to the N-terminus of the VEGF2 polypeptide to improve stability and persistence during purification from the host cell or subsequent handling and storage. Also, peptide moieties may be added to the VEGF2 polypeptide to facilitate purification. Such regions may be removed prior to final preparation of the VEGF2 polypeptide. The addition of peptide moieties to facilitate handling of polypeptides are familiar and routine techniques in the art.

Moreover, VEGF2 polypeptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).

Moreover, the VEGF2 polypeptides can be fused to marker sequences, such as a peptide which facilitates purification of VEGF2. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the VEGF2 polynucleotides or the polypeptides.

Biological Activities of VEGF2

VEGF2 polynucleotides and polypeptides can be used in assays to test for one or more biological activities. If VEGF2 polynucleotides and polypeptides do exhibit activity in a particular assay, it is likely that VEGF2 may be involved in the diseases associated with the biological activity. Therefore, VEGF2 could be used to treat the associated disease.

Immune Activity

VEGF2 polypeptides or polynucleotides may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, VEGF2 polynucleotides or polypeptides can be used as a marker or detector of a particular immune system disease or disorder.

VEGF2 polynucleotides or polypeptides may be useful in treating or detecting deficiencies or disorders of hematopoietic cells. VEGF2 polypeptides or polynucleotides could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobimuria.

Moreover, VEGF2 polypeptides or polynucleotides can also be used to modulate hemostatic (the stopping of bleeding) or thrombolytic activity (clot formation). For example, by increasing hemostatic or thrombolytic activity, VEGF2 polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, VEGF2 polynucleotides or polypeptides that can decrease hemostatic or thrombolytic activity could be used to inhibit or dissolve clotting, important in the treatment of heart attacks (infarction), strokes, or scaning.

VEGF2 polynucleotides or polypeptides may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of VEGF2 polypeptides or polynucleotides that can inhibit an immune response, particularly the proliferation, differentiation, or chemotaxis of T-cells, may be an effective therapy in preventing autoimmune disorders.

Examples of autoimmune disorders that can be treated or detected by VEGF2 include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by VEGF2 polypeptides or polynucleotides. Moreover, VEGF2 can be used to treat anaphylaxis, hypersensitivity to an antigenic molecule, or blood group incompatibility.

VEGF2 polynucleotides or polypeptides may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of VEGF2 polypeptides or polynucleotides that inhibits an immune response, particularly the proliferation, differentiation, or chemotaxis of T-cells, may be an effective therapy in preventing organ rejection or GVHD.

Similarly, VEGF2 polypeptides or polynucleotides may also be used to modulate inflammation. For example, VEGF2 polypeptides or polynucleotides may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1)

Hyperproliferative Disorders

VEGF2 polypeptides or polynucleotides can be used to treat or detect hyperproliferative disorders, including neoplasms. VEGF2 antagonist polypeptides or polynucleotides may inhibit the proliferation of the disorder through direct or indirect interactions. Alternatively, VEGF2 antagonist polypeptides or polynucleotides may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by VEGF2 antagonist polynucleotides or polypeptides include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by VEGF2 antagonist polynucleotides or polypeptides. Examples of such hyperproliferative disorders include, but are not limited to: hypergammaglobulinemia, lymphoproliferative disorders, paraproteinemias, purpura, sarcoidosis, Sezary Syndrome, Waldenstrons Macroglobulinemia, Gauchers Disease, histiocytosis, and any other hyperproliferative disease, besides neoplasia, located in an organ system listed above.

Infectious Disease

VEGF2 polypeptides or polynucleotides can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, VEGF2 polypeptides or polynucleotides may also directly inhibit the infectious agent, without necessarily eliciting an immune response.

Viruses are one example of an infectious agent that can cause disease or symptoms that can be treated or detected by VEGF2 polynucleotides or polypeptides. Examples of viruses, include, but are not limited to the following DNA and RNA viral families: Arbovirus, Adenoviridae, Arenaviridae, Arterivirus, Bimraviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. VEGF2 polypeptides or polynucleotide can be used to treat or detect any of these symptoms or diseases.

Similarly, bacterial or fungal agents that can cause disease or symptoms and that can be treated or detected by VEGF2 polynucleotides or polypeptides include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiters Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. VEGF2 polypeptides or polynucleotides can be used to treat or detec any of these symptoms or diseases.

Moreover, parasitic agents causing disease or symptoms that can be treated or detected by VEGF2 polynucleotides or polypeptides include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. VEGF2 polypeptides or polynucleotides can be used to treat or detect any of these symptoms or diseases.

Preferably, treatment using VEGF2 polypeptides or polynucleotides could either be by administering an effective amount of VEGF2 polypeptide to the patient, or by removing cells from the patient, supplying the cells with VEGF2 polynucleotide, and returning the engineered cells to the patient (ex vivo therapy). Moreover, the VEGF2 polypeptide or polynucleotide can be used as an antigen in a vaccine to raise an immune response against infectious disease.

Regeneration

VEGF2 polynucleotides or polypeptides can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), lymphatic (including lymphatic endothelium), nervous, hematopoietic, and skeletal (bone, cartilage, tendon, and ligament) tissue. Preferably, regeneration occurs without or decreased scarring. Regeneration also may include angiogenesis.

Moreover, VEGF2 polynucleotides or polypeptides may increase regeneration of tissues difficult to heal. For example, increased tendon/ligament regeneration would quicken recovery time after damage. VEGF2 polynucleotides or polypeptides of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using VEGF2 polynucleotides or polypeptides to proliferate an differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the VEGF2 polynucleotides or polypeptides.

Chemotaxis

VEGF2 polynucleotides or polypeptides may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

VEGF2 polynucleotides or polypeptides may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. As a chemotactic molecule, VEGF2 could also attract fibroblasts, which can be used to treat wounds.

It is also contemplated that VEGF2 polynucleotides or polypeptides may inhibit chemotactic activity. These molecules could also be used to treat disorders. Thus, VEGF2 polynucleotides or polypeptides could be used as an inhibitor of chemotaxis.

Binding Activity

VEGF2 polypeptides may be used to screen for molecules that bind to VEGF2 or for molecules to which VEGF2 binds. The binding of VEGF2 and the molecule may activate (agonist), increase, inhibit (antagonist), or decrease activity of the VEGF2 or the molecule bound. Examples of such molecules include antibodies, oligonucleotides, proteins (e.g., receptors),or small molecules.

Preferably, the molecule is closely related to the natural ligand of VEGF2, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which VEGF2 binds (i.e., Flt4), or at least, a fragment of the receptor capable of being bound by VEGF2 (e.g., active site). In either case, the molecule can be rationally designed using known techniques.

Preferably, the screening for these molecules involves producing appropriate cells which express VEGF2, either as a secreted protein or on the cell membrane. Preferred cells include cells from mammals, yeast, *Drosophila,* or *E. coli.* Cells expressing VEGF2 (or cell membrane containing the expressed polypeptide) are then preferably contacted with a test compound potentially containing the molecule to observe binding, stimulation, or inhibition of activity of either VEGF2 or the molecule.

The assay may simply test binding of a candidate compound to VEGF2, wherein binding is detected by a label, or in an assay involving competition with a labeled competitor. Further, the assay may test whether the candidate compound results in a signal generated by binding to VEGF2.

Alternatively, the assay can be carried out using cell-free preparations, polypeptide/molecule affixed to a solid support, chemical libraries, or natural product mixtures. The assay may also simply comprise the steps of mixing a candidate compound with a solution containing VEGF2, measuring VEGF2/molecule activity or binding, and comparing the VEGF2/molecule activity or binding to a stantard.

Preferably, an ELISA assay can measure VEGF2 level or activity in a sample (e.g., biological sample) using a monoclonal or polyclonal antibody. The antibody can measure VEGF2 level or activity by either binding, directly or indirectly, to VEGF2 or by competing with VEGF2 for a substrate.

All of these above assays can be used as diagnostic or prognostic markers. The molecules discovered using these assays can be used to treat disease or to bring about a particular result in a patient (e.g., blood vessel growth) by activating or inhibiting the VEGF2/molecule. Moreover, the assays can discover agents which may inhibit or enhance the production of VEGF2 from suitably manipulated cells or tissues.

Therefore, the invention includes a method of identifying compounds which bind to VEGF2 comprising the steps of: (a) incubating a candidate binding compound with VEGF2; and (b) determining if binding has occurred. Moreover, the invention includes a method of identifying agonists/antagonists comprising the steps of: (a) incubating a candidate compound with VEGF2, (b) assaying a biological activity, and (b) determining if a biological activity of VEGF2 has been altered.

Other Activities

VEGF2 polypeptides or polynucleotides may also increase or decrease the differentiation or proliferation of embryonic stem cells, besides, as discussed above, hematopoietic lineage.

VEGF2 polypeptides or polynucleotides may also be used to modulate mammalian characteristics, such as body height, weight, hair color, eye color, skin, percentage of adipose tissue, pigmentation, size, and shape (e.g., cosmetic surgery). Similarly, VEGF2 polypepties or polynucleotides may be used to modulate mammalian metabolism affecting catabolism, anabolism, processing, utilization, and storage of energy.

VEGF2 polypeptides or polynucleotides may be used to change a mammals mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

VEGF2 polypeptides or polynucleotides may also be used as a food additive or preservative, such as to increase or decrease storage capabilities, fat content, lipid, protein, carbohydrate, vitamins, minerals, cofactors or other nutritional components.

Vectors and Host Cells

The present invention also relates to recombinant vectors, which include the isolated nucleic acid molecules of the present invention, and to host cells containing the recombinant vectors, as well as to methods of making such vectors and host cells and for using them for production of VEGF2 polypeptides or peptides by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting tansformants, or amplifying the VEGF2 genes of the invention. The culture conditions, such as temperature, pH and the like, are those previously used with the host cell selected for expression, and will be apparent to the skilled artisan.

The polynucleotides of the present invention may be employed for producing polypeptides by recombinant techniques. Thus, for example, the polynucleotide sequence may be included in any one of a variety of expression vectors for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain at least one selectable marker gene to provide a phenotypic trait for selection of transformed host cells. Such markers include dihydrofolate reductase (DHFR) or neomycin resistance for eukaryotic cell culture, and tetracycline or ampicillin resistance for culturing in *E. coli* and other bacteria.

The vector containing the appropriate DNA sequence as herein above described, as well as an appropriate promoter or control sequence, may be employed to transform an appropriate host to permit the host to express the protein. Representative examples of appropriate hosts, include but are not limited to: bacterial cells, such as *E. coli, Salmonella typhimurium,* and *Streptomyces;* fungal cells, such as yeast; insect cells, such as *Drosophila* S2 and *Spodoptera* Sf9; animal cells such as CHO, COS, and Bowes melanoma; and plant cells. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example—bacterial: pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figure 28:
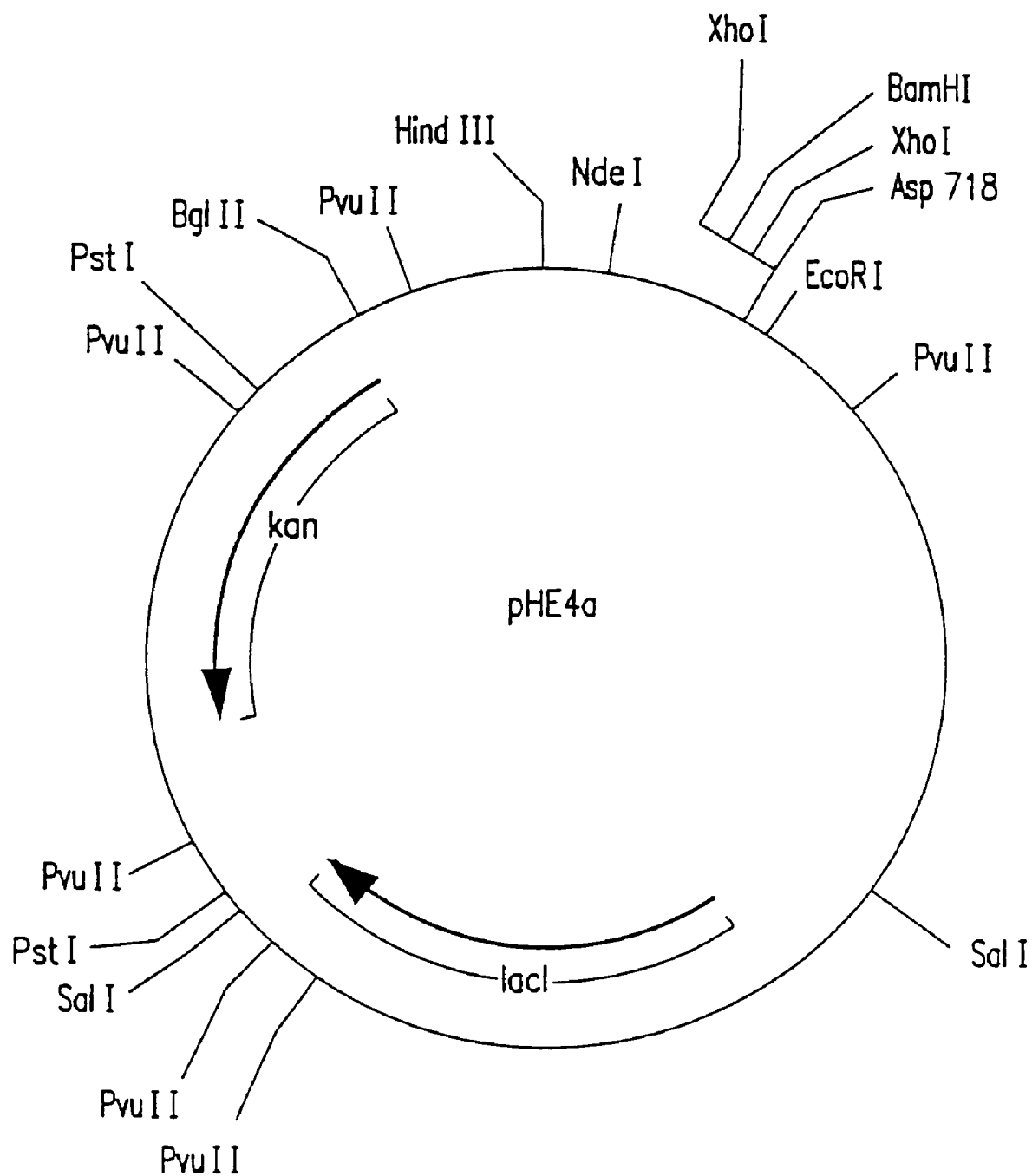
FIG. 28 shows a schematic representation of the pHE4a expression vector (SEQ ID NO:16). The locations of the kanamycin resistance marker gene, the multiple cloning site linker region, the oriC sequence, and the lacIq coding sequence are indicated.

As summarized in FIGS. 28 and 29, components of the pHE4a vector (SEQ ID NO:16) include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215-216, CLONTECH, 1020 East Meadow Circle, Palo Alto, Calif. 94303. The pHE4a vector was deposited with the ATCC on Feb. 25, 1998, and given accession number209645.

A nucleotide sequence encoding VEGF-2 (SEQ ID NO: 1), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding VEGF-2 (SEQ ID NO:1) having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al, *Gene* 69:301-315 (1988); Stark, M., *Gene* 51:255-267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). VEGF-2 thus is not produced in appreciable quantities in uninduced host cells containing the pHE4a vector. Induction of these host cells by the addition of an agent such as IPTG, however, results in the expression of the VEGF-2 coding sequence.

The promoter/operator sequences of the pHE4a vector (SEQ ID NO:17) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG.

Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802-807.

The pHE4 series of vectors contain all of the components of the pHE4a vector except for the VEGF-2 coding sequence. Features of the pHE4a vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO:16).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, electroporation, transduction, infection, or other methods (Davis, L., et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., *Molecular Cloning: A Laboratory Manual,* Second Edition, Cold Spring Harbor Laboratory, Cold Spring Harbor, N.Y. (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, well known to those skilled in the art, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

The polypeptides can be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1-5 mM) of calcium ion present during purification (Price et al., *J. Biol. Chem.* 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

Therapeutic Uses

Figure 12:
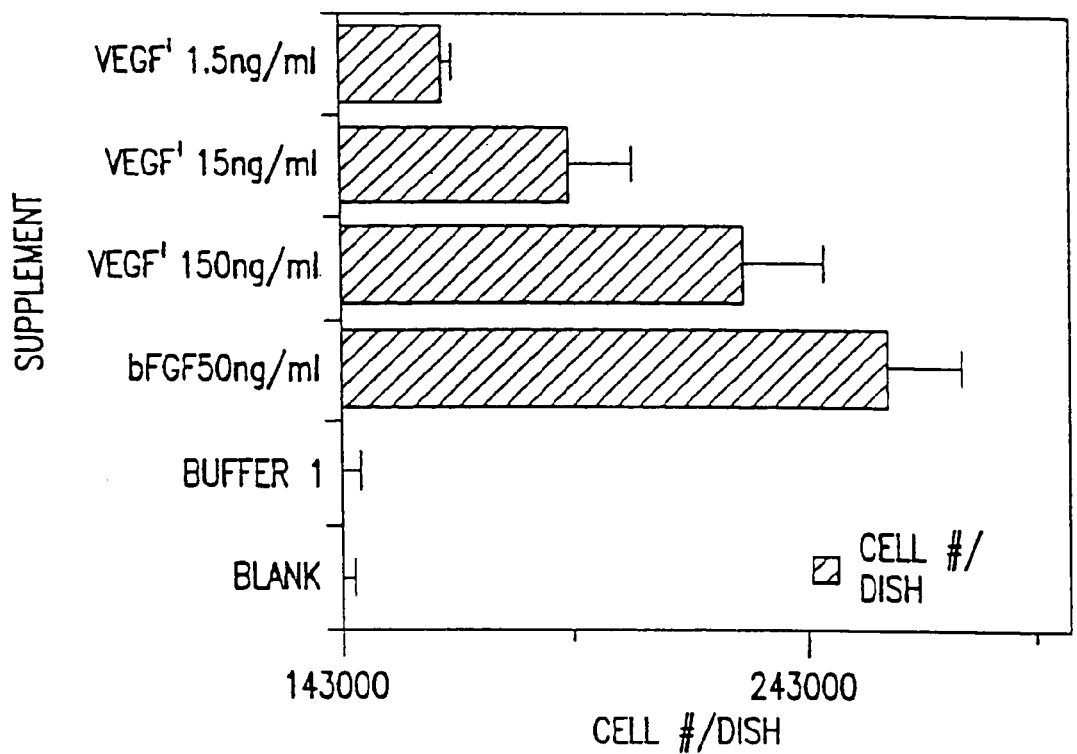
FIG. 12 is a bar graph illustrating the effect of partially-purified VEGF2 protein on the growth of vascular endothelial cells in comparison to basic fibroblast growth factor.
Figure 13:
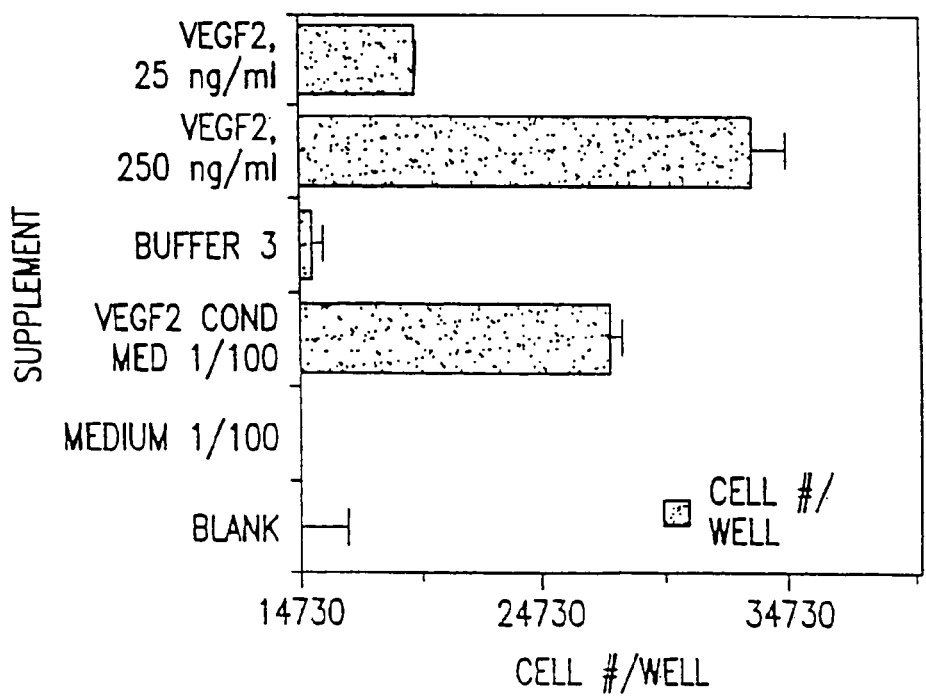
FIG. 13 is a bar graph illustrating the effect of purified VEGF2 protein on the growth of vascular endothelial cells.

The VEGF-2 polypeptide of the present invention is a potent mitogen for vascular and lymphatic endothelial cells. As shown in FIGS. 12 and 13, the VEGF2 polypeptide of SEQ ID NO:2, minus the initial 46 amino acids, is a potent mitogen for vascular endothelial cells and stimulates their growth and proliferation. The results of a Northern blot analysis performed for the VEGF2 nucleic acid sequence encoding this polypeptide wherein 20 μg of RNA from several human tissues were probed with $^{32}$P-VEGF2, illustrates that this protein is activity expressed in the heart and lung which is further evidence of mitogenic activity.

Accordingly, VEGF2, or biologically active portions thereof, may be employed to treat vascular trauma by promoting angiogenesis. For example, to stimulate the growth of transplanted tissue where coronary bypass surgery is performed. VEGF2, or biologically active portions thereof, may also be employed to promote wound healing, particularly to re-vascularize damaged tissues or stimulate collateral blood flow during ischemia and where new capillary angiogenesis is desired. VEGF2, or biologically active portions thereof, may be employed to treat full-thickness wounds such as dermal ulcers, including pressure sores, venous ulcers, and diabetic ulcers. In addition, VEGF2, or biologically active portions thereof, may be employed to treat full-thickness burns and injuries where a skin graft or flap is used to repair such burns and injuries. VEGF2, or biologically active portions thereof, may also be employed for use in plastic surgery, for example, for the repair of lacerations, burns, or other trauma. In addition, VEGF-2 can be used to promote healing of wounds and injuries to the eye as well as to treat eye diseases.

Along these same lines, VEGF2, or biologically active portions thereof, may also be employed to induce the growth of damaged bone, periodontium or ligament tissue. VEGF2, or biologically active portions thereof, may also be employed for regenerating supporting tissues of the teeth, including cementum and periodontal ligament, that have been damaged by, e.g., periodental disease or trauma Since angiogenesis is important in keeping wounds clean and non-infected, VEGF2, or biologically active portions thereof, may be employed in association with surgery and following the repair of incisions and cuts. VEGF2, or biologically active portions thereof, may also be employed for the treatment of abdominal wounds where there is a high risk of infection.

VEGF2, or biologically active portions thereof, may be employed for the promotion of endothelialization in vascular graft surgery. In the case of vascular grafts using either transplanted or synthetic material, VEGF2, or biologically active portions thereof, can be applied to the surface of the graft or at the junction to promote the growth of vascular endothelial cells. VEGF2, or biologically active portions thereof, may also be employed to repair damage of myocardial tissue as a result of myocardial infarction. VEGF2, or biologically active portions thereof, may also be employed to repair the cardiac vascular system after ischemia VEGF2, or biologically active portions thereof, may also be employed to treat damaged vascular tissue as a result of coronary artery disease and peripheral and CNS vascular disease.

VEGF2, or biologically active portions thereof, may also be employed to coat artificial prostheses or natural organs which are to be transplanted in the body to minimize rejection of the transplanted material and to stimulate vascularization of the transplanted materials.

VEGF2, or biologically active portions thereof, may also be employed for vascular tissue repair of injuries resulting from trauma, for example, that occurring during arteriosclerosis and required following balloon angioplasty where vascular tissues are damaged.

VEGF2, or biologically active portions thereof, may also be used to treat peripheral arterial disease. Accordingly, in a further aspect, there is provided a process for utilizing VEGF2 polypeptides to treat peripheral arterial disease. Preferably, a VEGF-2 polypeptide is administered to an individual for the purpose of alleviating or treating peripheral arterial disease. Suitable doses, formulations, and administration routes are described below.

VEGF2, or biologically active portions thereof, may also to promote the endothelial function of lymphatic tissues and vessels, such as to treat the loss of lymphatic vessels, occlusions of lymphatic vessels, and lymphangiomas. VEGF-2 may also be used to stimulate lymphocyte production.

VEGF2, or biologically active portions thereof, may also be used to treat hemangioma in newborns. Accordingly, in a further aspect, there is provided a process for utilizing VEGF2 polypeptides to treat hemangioma in newborns. Preferably, a VEGF-2 polypeptide is administered to an individual for the purpose of alleviating or treating hemangioma in newborns. Suitable doses, formulations, and administration routes are described below.

VEGF2, or biologically active portions thereof, may also be used to prevent or treat abnormal retinal development in premature newborns. Accordingly, in a further aspect, there is provided a process for utilizing VEGF2 polypeptides to treat abnormal retinal development in premature newborns. Preferably, a VEGF-2 polypeptide is administered to an individual for the purpose of alleviating or treating abnormal retinal development in premature newborns. Suitable doses, formulations, and administration routes are described below.

VEGF2, or biologically active portions thereof, may be used to treat primary (idiopathic) lymphademas, including Milroy's disease and Lymphedema praecox. Accordingly, in a further aspect, there is provided a process for utilizing VEGF2 polypeptides to treat primary (idiopathic) lymphademas, including Milroy's disease and Lymphedema praecox. Preferably, a VEGF-2 polypeptide is administered to an individual for the purpose of alleviating or treating primary (idiopathic) lymphademas, including Milroy's disease and Lymphedema praecox. VEGF-2 or biologically active portions thereof, may also be used to treat edema as well as to effect blood pressure in an animal. Suitable doses, formulations, and administration routes are described below.

VEGF2, or biologically active portions thereof, may also be used to treat secondary (obstructive) lyphademas including those that result from (I) the removal of lymph nodes and vessels, (ii) radiotherapy and surgery in the treatment of cancer, and (iii) trauma and infection. Accordingly, in a further aspect, there is provided a process for utilizing VEGF2 polypeptides to treat secondary (obstructive) lyphademas including those that result from (I) the removal of lymph nodes and vessels, (ii) radiotherapy and surgery in the treatment of cancer, and (iii) trauma and infection. Preferably, a VEGF-2 polypeptide is administered to an individual for the purpose of secondary (obstructive) lyphademas including those that result from (I) the removal of lymph nodes and vessels, (ii) radiotherapy and surgery in the treatment of cancer, and (iii) trauma and infection Suitable doses, formulations, and administration routes are described below.

VEGF2, or biologically active portions thereof, may also be used to treat Kaposi's Sarcoma. Accordingly, in a further aspect, there is provided a process for utilizing VEGF2 polypeptides to treat Kaposi's Sarcoma. Preferably, a VEGF-2 polypeptide is administered to an individual for the purpose of alleviating or treating Kaposi's Sarcoma. Suitable doses, formulations, and administration routes are described below.

VEGF-2 antagonists can be used to treat cancer by inhibiting the angiogenesis necessary to support cancer and tumor growth.

Gene Therapy Methods

Another aspect of the present invention is to gene therapy methods to treat disorders, diseases and conditions. The gene therapy method relates to the introduction of naked nucleic acid (DNA, RNA and antisense DNA or RNA) sequences into an animal to achieve expression of the VEGF-2 polypeptide of the present invention. This method requires polynucleotide which codes for a VEGF-2 polypeptide operatively linked to a promoter and any other genetic elements necessary for the expression of the polypeptide by the target tissue. Such gene therapy and delivery techniques are known in the art, see, for example, WO90/11092, which is herein incorporated by reference.

As discussed in more detail below, the VEGF-2 polynucleotide constructs can be delivered by any method that delivers injectable materials to the cells of an animal, such as, injection into the interstitial space of tissues (heart, muscle, skin, lung, liver, and the like). The VEGF-2 polynucleotide constructs are delivered in a pharmaceutically acceptable liquid or aqueous carrier.

The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the VEGF-2 polynucleotides can also be delivered in liposome formulations and lipofectin formulations and the like can be prepared by methods well known to those skilled in the art.

The VEGF-2 polynucleotide vector constructs used in the gene therapy method are preferably constructs that will not integrate into the host genome nor will they contain sequences that allow for replication. Any strong promoter known to those skilled in the art can be used for driving the expression of VEGF-2 DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The VEGF-2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, macopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 µg/kg body weight to about 50 mg/kg body weight Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked VEGF-2 DNA constructs can be delivered to arteries during angioplasty by the catheter used in the procedure.

As is evidenced by Example 18, naked VEGF-2 nucleic acid sequences can be administered in vivo results in the successful expression of VEGF-2 polypeptide in the femoral arteries of rabbits.

Nucleic Acid Utilities

VEGF2 nucleic acid sequences and VEGF2 polypeptides may also be employed for in vitro purposes related to scientific research, synthesis of DNA and manufacture of DNA vectors, and for the production of diagnostics and therapeutics to treat human disease. For example, VEGF2 may be employed for in vitro culturing of vascular endothelial cells, where it is added to the conditional medium in a concentration from 10 pg/ml to 10 ng/ml.

Fragments of the full length VEGF2 gene may be used as a hybridization probe for a cDNA library to isolate other genes which have a high sequence similarity to the gene or similar biological activity. Probes of this type generally have at least 50 base pairs, although they may have a greater number of bases. The probe may also be used to identify a cDNA clone corresponding to a full length transcript and a genomic clone or clones that contain the complete VEGF2 gene including regulatory and promotor regions, exons, and introns. An example of a screen comprises isolating the coding region of the VEGF2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides methods for identification of VEGF2 receptors. The gene encoding the receptor can be identified by numerous methods known to those of skill in the art, for example, ligand panning and FACS sorting (Coligan et al., Current Protocols in Immun., 1(2), Chapter 5, (1991)). Preferably, expression cloning is employed wherein polyadenylated RNA is prepared from a cell responsive to VEGF2, and a cDNA library created from this RNA is divided into pools and used to transfect COS cells or other cells that are not responsive to VEGF2. Transfected cells which are grown on glass slides are exposed to labeled VEGF2. VEGF2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VEGF2 can be photoaffinity linked with cell membrane or extract preparations that express the receptor molecule. Cross-linked material is resolved by PAGE and exposed to X-ray film. The labeled complex containing VEGF2 is then excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

VEGF-2 Agonist and Antagonists

This invention is also related to a method of screening compounds to identify those which are VEGF2 agonists or antagonists. An example of such a method takes advantage of the ability of VEGF2 to significantly stimulate the proliferation of human endothelial cells in the presence of the cornitogen Con A. Endothelial cells are obtained and cultured in 96-well flat-bottomed culture plates (Costar, Cambridge, Mass.) in a reaction mixture supplemented with Con-A (Calbiochem, La Jolla, Calif.). Con-A, polypeptides of the present invention and the compound to be screened are added. After incubation at 37° C., cultures are pulsed with 1 μCi of $^3$[H] thymidine (5 Ci/mmol; 1 Ci=37 BGq; NEN) for a sufficient time to incorporate the $^3$[H] and harvested onto glass fiber filters (Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]thymidine incorporation, as compared to a control assay where the compound is excluded, indicates stimulation of endothelial cell proliferation.

To assay for antagonists, the assay described above is performed and the ability of the compound to inhibit .sup.3[H] thymidine incorporation in the presence of VEGF2 indicates that the compound is an antagonist to VEGF2. Alternatively, VEGF2 antagonists may be detected by combining VEGF2 and a potential antagonist with membrane-bound VEGF2 receptors or recombinant receptors under appropriate conditions for a competitive inhibition assay. VEGF2 can be labeled, such as by radioactivity, such that the number of VEGF2 molecules bound to the receptor can determine the effectiveness of the potential antagonist.

Alternatively, the response of a known second messenger system following interaction of VEGF2 and receptor would be measured and compared in the presence or absence of the compound. Such second messenger systems include but are not limited to, cAMP guanylate cyclase, ion channels or phosphoinositide hydrolysis. In another method, a mammalian cell or membrane preparation expressing the VEGF2 receptor is incubated with labeled VEGF2 in the presence of the compound. The ability of the compound to enhance or block this interaction could then be measured.

Potential VEGF2 antagonists include an antibody, or in some cases, an oligonucleotide, which bind to the polypeptide and effectively eliminate VEGF2 function. Alternatively, a potential antagonist may be a closely related protein which binds to VEGF2 receptors, however, they are inactive forms of the polypeptide and thereby prevent the action of VEGF2. Examples of these antagonists include a negative dominant mutant of the VEGF2 polypeptide, for example, one chain of the hetero-dimeric form of VEGF2 may be dominant and may be mutated such that biological activity is not retained. An example of a negative dominant mutant includes truncated versions of a dimeric VEGF2 which is capable of interacting with another dimer to form wild type VEGF2, however, the resulting homo-dimer is inactive and fails to exhibit characteristic VEGF activity.

Another potential VEGF2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription(triple helix—see Lee et al., Nucl. Acids Res. 6:3073(1979); Cooney et al., Science 241:456 (1988); and Dervan et al., Science 251:1360 (1991)), thereby preventing transcription and the production of VEGF2. The antisense RNA oligonucleotide hybridizes to the mRNA in vivo and blocks translation of the mRNA molecule into the VEGF2 polypeptide (Antisense—Okano, J. Neurochem. 56:560 (1991); Oligodeoxynucleotides as Antisense inhibitors of Gene Expression, CRC Press, Boca Raton, Fla. (1988)). The oligonucleotides described above can also be delivered to cells such that the antisense RNA or DNA may be expressed in vivo to inhibit production of VEGF2.

Potential VEGF2 antagonists also include small molecules which bind to and occupy the active site of the polypeptide thereby making the catalytic site inaccessible to substrate such that normal biological activity is prevented. Examples of small molecules include but are not limited to small peptides or peptide-like molecules.

The antagonists may be employed to limit angiogenesis necessary for solid tumor metastasis. The identification of VEGF2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF2 is extremely low in normal tissues including breast, it can be found expressed at moderate levels in at least two breast tumor cell lines that are derived from malignant tumors. It is, therefore, possible that VEGF2 is involved in tumor angiogenesis and growth.

Gliomas are also a type of neoplasia which may be treated with the antagonists of the present invention.

The antagonists may also be used to treat chronic inflammation caused by increased vascular permeability. In addition to these disorders, the antagonists may also be employed to treat retinopathy associated with diabetes, rheumatoid arthritis and psoriasis.

The antagonists may be employed in a composition with a pharmaceutically acceptable carrier, e.g., as hereinafter described.

The VEGF2 polypeptides and agonists and antagonists may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the pharmaceutical compositions are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The VEGF2 polypeptides, and agonists or antagonists which are polypeptides may also be employed in accordance with the present invention by expression of such polypeptide in vivo, which is often referred to as "gene therapy."

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of a polypeptide in vivo, for example, by procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., Biotechniques 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter, or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, Human Gene Therapy 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s)

encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the VEGF2 gene as part of a diagnostic assay for detecting diseases or susceptibility to diseases related to the presence of mutations in VEGF2 nucleic acid sequences.

Individuals carrying mutations in the VEGF2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature 324:163-166 (1986)) prior to analysis. RNA or cDNA may also be used for the same purpose. As an example, PCR primers complementary to the nucleic acid encoding VEGF2 can be used to identify and analyze VEGF2 mutations. For example, deletions and insertions can be detected by a change in size of the amplified product in comparison to the normal genotype. Point mutations can be identified by hybridizing amplified DNA to radiolabeled VEGF2 RNA or alternatively, radiolabeled VEGF2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:1242 (1985)).

Sequence changes at specific locations may also be revealed by nuclease protection assays, such as RNase and S1 protection or the chemical cleavage method (e.g., Cotton et al., PNAS, USA 85:4397-4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of VEGF2 protein in various tissues since an over-expression of the proteins compared to normal control tissue samples may detect the presence of a disease or susceptibility to a disease, for example, abnormal cellular differentiation. Assays used to detect levels of VEGF2 protein in a sample derived from a host are well-known to those of skill in the art and include radioimmunoassays, competitive-binding assays, Western Blot analysis, ELISA assays and "sandwich" assay. An ELISA assay (Coligan et al., Current Protocols in Immunology 1(2), Chapter 6, (1991)) initially comprises preparing an antibody specific to the VEGF2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, such as, bovine serum albumen. Next, the monoclonal antibody is incubated in the dish during which time the monoclonal antibodies attach to any VEGF2 proteins attached to the polystyrene dish. All unbound monoclonal antibody is washed out with buffer. The reporter antibody linked to horseradish peroxidase is placed in the dish resulting in binding of the reporter antibody to any monoclonal antibody bound to VEGF2. Unattached reporter antibody is then washed out. Peroxidase substrates are then added to the dish and the amount of color developed in a given time period is a measurement of the amount of VEGF2 protein present in a given volume of patient sample when compared against a standard curve.

A competition assay may be employed wherein antibodies specific to VEGF2 are attached to a solid support. Polypeptides of the present invention are then labeled, for example, by radioactivity, and a sample derived from the host are passed over the solid support and the amount of label detected, for example by liquid scintillation chromatography, can be correlated to a quantity of VEGF2 in the sample.

A "sandwich" assay is similar to an ELISA assay. In a "sandwich" assay VEGF2 is passed over a solid support and binds to antibody attached to a solid support. A second antibody is then bound to the VEGF2. A third antibody which is labeled and specific to the second antibody is then passed over the solid support and binds to the second antibody and an amount can then be quantified.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with probes from the cDNA as short as 50 or 60 base pairs. For a review of this technique, see Verma et al, Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting VEGF2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al., Nucl. Acids Res. 6:3073 (1979); Cooney et al., Science 241:456 (1988); and Dervan et al. Science, 251:1360 (1991), thereby preventing transcription and the production of VEGF2. The antisense RNA oligonucleotide hybridizes to the mRNA in vivo and blocks translation of an mRNA molecule into the VEGF2 (antisense—Okano, J. Neurochem. 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the antisense RNA or DNA may be expressed in vivo to inhibit production of VEGF2 in the manner described above.

Antisense constructs to VEGF2, therefore, may inhibit the angiogenic activity of the VEGF2 and prevent the further growth or even regress solid tumors, since angiogenesis and neovascularization are essential steps in solid tumor growth.

These antisense constructs may also be used to treat rheumatoid arthritis, psoriasis, diabetic retinopathy and Kaposi's sarcoma which are all characterized by abnormal angiogenesis.

The polypeptides, their fragments or other derivatives, or analogs thereof, or cells expressing them can be used as an immunogen to produce antibodies thereto. These antibodies can be, for example, polyclonal or monoclonal antibodies.

The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, Nature 256:495-497 (1975)), the trioma technique, the human B-cell hybridoma technique (Kozbor et al., Immunology Today 4:72 (1983)), and the EBV-hybridoma technique to produce human monoclonal antibodies (Cole et al., in Monoclonal Antibodies and Cancer Therapy, Alan R. Liss, Inc. (1985), pp. 77-96).

Techniques described for the production of single chain antibodies (U.S. Pat. No. 4,946,778) can be adapted to produce single chain antibodies to immunogenic polypeptide products of this invention.

Neutralization antibodies can be identified and applied to mask the vascular endothelial growth factor, and that has been shown in mice model systems against VEGF. VEGF2 can also be inactivated by certain dominant negative mutants within the gene itself. It is known that both PDGFα and β form either heterodimers or homodimers, and VEGF forms homodimers. Similar interaction between VEGF2 could be expected. These antibodies therefore may be used to block the angiogenic activity of VEGF2 and retard the growth of solid tumors. These antibodies may also be used to treat inflammation caused by the increased vascular permeability which results from the presence of VEGF2.

These antibodies may further be used in an immunoassay to detect the presence of tumors in certain individuals. Enzyme immunoassay can be performed from the blood sample of an individual. Elevated levels of VEGF2 can be considered diagnostic of cancer.

The present invention is also directed to antagonist/inhibitors of the polypeptides of the present invention. The antagonist/inhibitors are those which inhibit or eliminate the function of the polypeptide.

Thus, for example, antagonists bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Truncated versions of VEGF2 can also be produced that are capable of interacting with wild type VEGF2 to form dimers that fail to activate endothelial cell growth, therefore inactivating the endogenous VEGF2. Or, mutant forms of VEGF2 form dimers themselves and occupy the ligand binding domain of the proper tyrosine kinase receptors on the target cell surface, but fail to activate cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF2 since receptor sites are occupied. In these ways, the action of the VEGF2 is prevented and the antagonist/inhibitors may be used therapeutically as an anti-tumor drug by occupying the receptor sites of tumors which are recognized by VEGF2 or by inactivating VEGF2 itself. The antagonist/inhibitors may also be used to prevent inflammation due to the increased vascular permeability action of VEGF2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res. 8:4057 (1980).

"Oligonucleotides" refer to either a single stranded polydeoxynucleotide or two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook et al., Molecular Cloning: A Laboratory Manual, Second Edition, Cold Spring Harbor Laboratory, Cold Spring Harbor, N.Y. (1989), p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described by the method of Graham, F. and Van der Eb, A., Virology 52:456-457 (1973).

EXAMPLE 1

Expression Pattern of VEGF2 in Human Tissues and Breast Cancer Cell Lines

Northern blot analysis was carried out to examine the levels of expression of VEGF2 in human tissues and breast cancer cell lines in human tissues. Total cellular RNA samples were isolated with RNAzol™ B system (Biotecx Laboratories, Inc.). About 10 µg of total RNA isolated from each breast tissue and cell line specified was separated on 1% agarose gel and blotted onto a nylon filter, (Sambrook et al., Molecular Cloning: A Laboratory Manual, Second Edition, Cold Spring Harbor Laboratory, Cold Spring Harbor, N.Y. (1989)). The labeling reaction was done according to the Stratagene Prime-It kit with 50 ng DNA fragment. The labeled DNA was purified with a Select-G-50 column from 5 Prime→3 Prime, Inc (Boulder, Colo.). The filter was then hybridized with a radioactive labeled full length VEGF2 gene at 1,000,000 cpm/ml in 0.5 M NaPO$_4$ and 7% SDS overnight at 65° C. After washing twice at room temperature and twice at 60° C. with 0.5×SSC, 0.1% SDS, the filters were then exposed at −70° C. overnight with an intensifying screen. A message of 1.6 Kd was observed in 2 breast cancer cell lines. FIG. 5, lane #4 represents a very tumorigenic cell line that is estrogen independent for growth.

Also, 10 µg of total RNA from 10 human adult tissues were separated on an agarose gel and blotted onto a nylon filter was then hybridized with radioactively labeled VEGF2 probe in 7% SDS, 0.5 M NaPO$_4$, pH 7.2; 1% BSA overnight at 65° C. Following washing in 0.2×SSC at 65° C., the filter was exposed to film for 24 days at −70° C. with intensifying screen. See FIG. 6.

EXAMPLE 2

Expression of the Truncated Form of VEGF2 (SEQ ID NO:4) by in vitro Transcription and Translation The VEGF2 cDNA was transcribed and translated in vitro to determine the size of the translatable polypeptide encoded by the truncated form of VEGF2 and a partial VEGF2 cDNA. The two inserts of VEGF2 in the pBluescript SK vector were amplified by PCR with three pairs of primers, 1) M13-reverse and forward primers; 2) M13-reverse primer and VEGF primer F4; and 3) M13-reverse primer and VEGF primer F5. The sequence of these primers are as follows.

M13-2 reverse primer:
5'-ATGCTTCCGGCTCGTATG-3' (SEQ ID NO: 9)

This sequence is located upstream of the 5' end of the VEGF2 cDNA insert in the pBluescript vector and is in an anti-sense orientation as the cDNA. A T3 promoter sequence is located between this primer and the VEGF2 cDNA.

M13-2 forward primer:
5'GGGT-MTCCCAGTCACGAC-3' (SEQ ID NO: 10)

This sequence is located downstream of the 3' end of the VEGF2 cDNA insert in the pBluescript vector and is in an anti-sense orientation as the cDNA insert.

VEGF primer F4:
5'-CCACATGGTTCAGGAAAGACA-3' (SEQ ID NO: 11)

This sequence is located within the VEGF2 cDNA in an anti-sense orientation from bp 1259-1239, which is about 169 bp away from the 3' end of the stop codon and about 266 bp before the last nucleotide of the cDNA.

PCR reaction with all three pairs of primers produce amplified products with T3 promoter sequence in front of the cDNA insert. The first and third pairs of primers produce PCR products that encode the polypeptide of VEGF2 shown in SEQ ID NO:4. The second pair of primers produce PCR product that misses 36 amino acids coding sequence at the C-terminus of the VEGF2 polypeptide.

Approximately 0.5 µg of PCR product from first pair of primers, 1 µg from second pair of primers, 1 µg from third pair of primers were used for in vitro transcription/translation. The in vitro transcription/translation reaction was performed in a 25 µl of volume, using the $T_N T^{TM}$ Coupled Reticulocyte Lysate Systems (Promega, CAT #LA950). Specifically, the reaction contains 12.5 µl of $T_N T$ rabbit reticulocyte lysate 2 µl of $T_N T$ reaction buffer, 1 µl of T3 polymerase, 1 µl of 1 mM amino acid mixture (minus methionine), 4 µl of $^{35}$S-methionine (>1000 Ci/mmol, 10 mCi/ml), 1 µl of 40 U/ul; RNasin ribonuclease inhibitor, 0.5 or 1 µg of PCR products. Nuclease-free $H_2O$ was added to bring the volume to 25 µl. The reaction was incubated at 30° C. for 2 hours. Five microliters of the reaction product was analyzed on a 4-20% gradient SDS-PAGE gel. After fixing in 25% isopropanol and 10% acetic acid, the gel was dried and exposed to an X-ray film overnight at 70° C.

Figure 7:
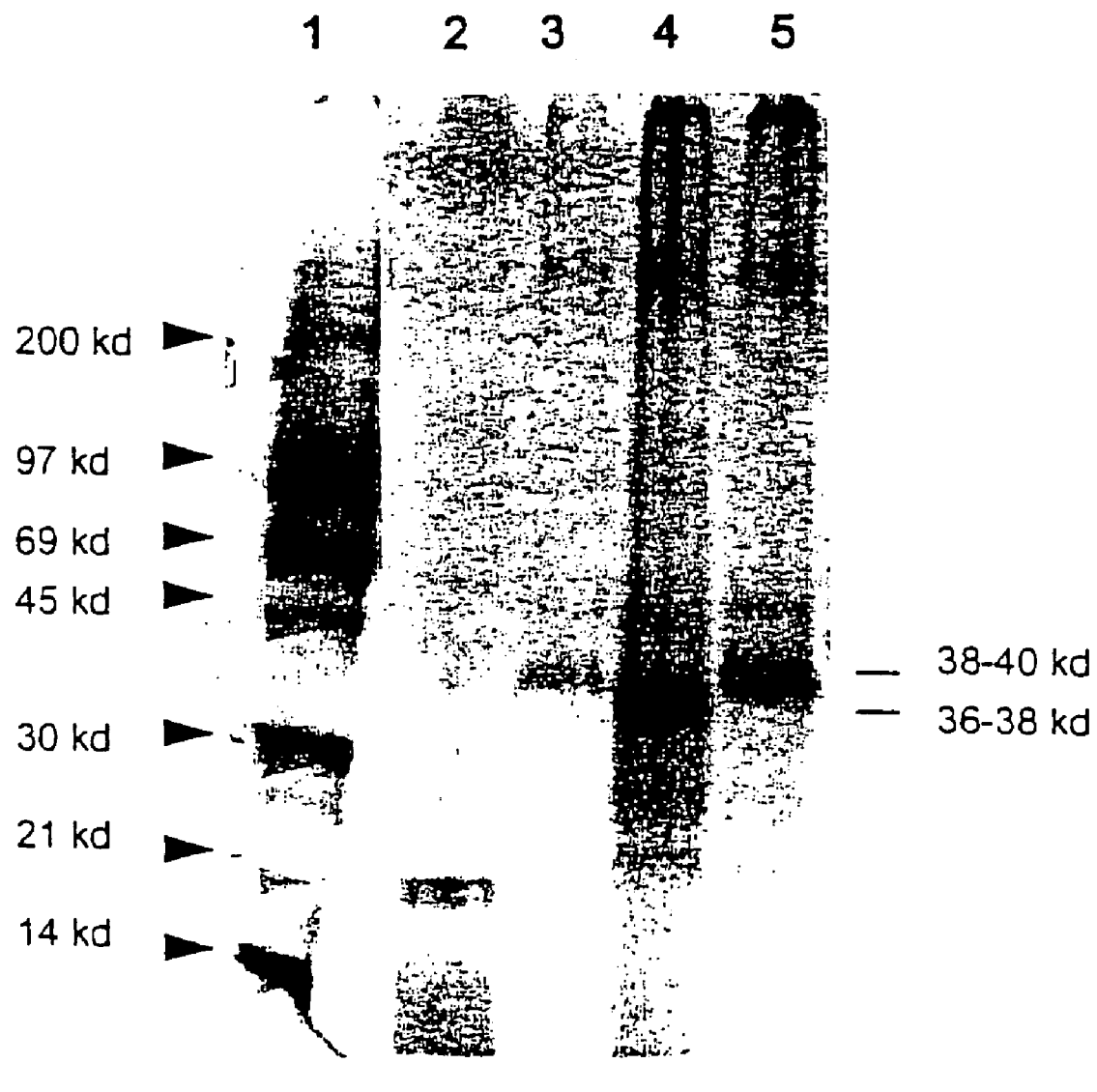
FIG. 7 shows a photograph of an SDS-PAGE gel after in vitro transcription, translation and electrophoresis of the polypeptide of the present invention. Lane 1: $^{14}$C and rainbow M. W. marker; Lane 2: FGF control; Lane 3: VEGF2 produced by M13-reverse and forward primers; Lane 4: VEGF2 produced by M13 reverse and VEGF-F4 primers; Lane 5: VEGF2 produced by M13 reverse and VEGF-F5 primers.
Figure 8:
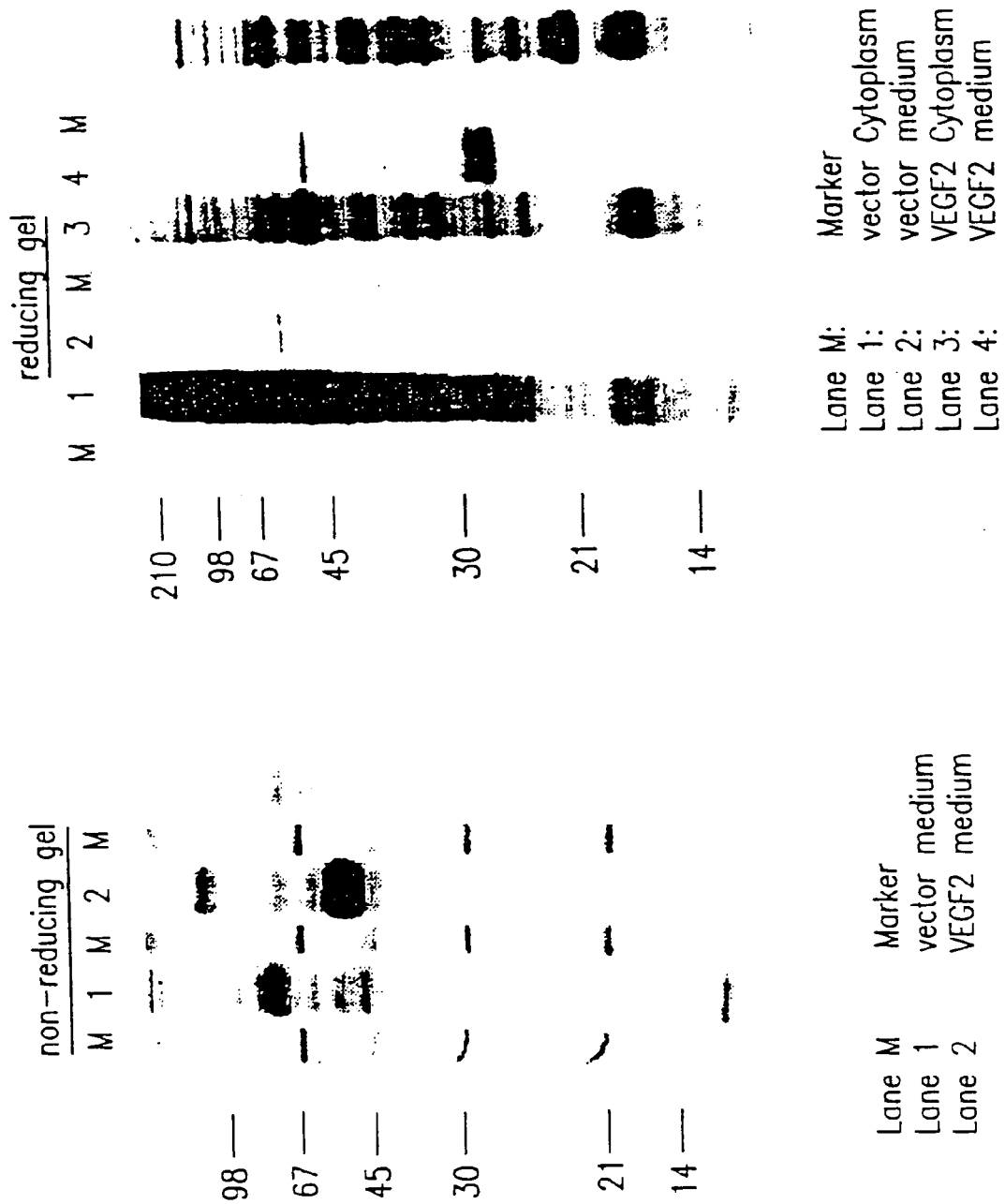
FIGS. 8A and 8B depict photographs of SDS-PAGE gels. VEGF2 polypeptide was expressed in a baculovirus system consisting of Sf9 cells. Protein from the medium and cytoplasm of cells were analyzed by SDS-PAGE under non-reducing (FIG. 8A) and reducing (FIG. 8B) conditions.

As shown in FIG. 7, PCR products containing the truncated VEGF2 cDNA (i.e., as depicted in SEQ ID NO:3) and the cDNA missing 266 bp in the 3' un-translated region (3'-UTR) produced the same length of translated products, whose molecular weights are estimated to be 38-40 kd (lanes 1 and 3 The cDNA missing all the 3'UTR and missing sequence encoding the C-terminal 36 amino acids was translated into a polypeptide with an estimated molecular weight of 36-38 kd (lane 2).

EXAMPLE 3

Cloning and Expression of VEGF2 Using the Baculovirus Expression System

The DNA sequence encoding the VEGF2 protein without 46 amino acids at the N-terminus, see ATCC No. 97149, was amplified using PCR oligonucleotide primers corresponding to the 5' and 3' sequences of the gene:

The 5' primer has the sequence TGT AAT ACG ACT CAC TAT AGG GAT CCC GCC ATG GAG GCC ACG GCT TAT GC (SEQ ID NO:12) and contains a BamHI restriction enzyme site (in bold) and 17 nucleotide sequence complementary to the 5' sequence of VEGF2 (nt. 150-166).

The 3' primer has the sequence GATC TCT AGA TTA GCT CAT TTG TGG TCT (SEQ ID NO:13) and contains the cleavage site for the restriction enzyme XbaI and 18 nucleotides complementary to the 3' sequence of VEGF2, including the stop codon and 15 nt sequence before stop codon.

The amplified sequences were isolated from a 1% agarose gel using a commercially available kit ("Geneclean," BIO 101, Inc., La Jolla, Calif.). The fragment was then digested with the endonuclease BamHI and XbaI and then purified again on a 1% agarose gel. This fragment was ligated to pAcGP67A baculovirus transfer vector (Pharmingen) at the BamH1 and XbaI sites. Through this ligation, VEGF2 cDNA was cloned in frame with the signal sequence of baculovirus gp67 gene and was located at the 3' end of the signal sequence in the vector. This is designated pAcGP67A-VEGF2.

To clone VEGF2 with the signal sequence of gp67 gene to the pRG1 vector for expression, VEGF2 with the signal sequence and some upstream sequence were excised from the pAcGP67A-VEGF2 plasmid at the Xho restriction endonuclease site located upstream of the VEGF2 cDNA and at the XbaI restriction endonuclease site by XhoI and XbaI restriction enzyme. This fragment was separated from the rest of vector on a 1% agarose gel and was purified using "Geneclean" kit. It was designated F2.

The PRG1 vector (modification of pVL941 vector) is used for the expression of the VEGF2 protein using the baculovirus expression system (for review see: Summers, M. D. and Smith, G. E., "A Manual of Methods for Baculovirus Vectors and Insect Cell Culture Procedures," Texas Agricultural Experimental Station Bulletin No. 1555, (1987)). This expression vector contains the strong polyhedrin promoter of the *Autographa californica* nuclear polyhedrosis virus (AcMNPV) followed by the recognition sites for the restriction endonucleases BamH1, Sma1, XbaI, BglII and Asp718. A site for restriction endonuclease XhoI is located upstream of BamH1 site. The sequence between Xho1 and BamHI is the same as that in PAcGp67A (static on tape) vector. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology 170: 31-39 (1989).

The plasmid was digested with the restriction enzymes XboI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E. coli* HB101 cells were then transformed and bacteria identified that contained the plasmid (pBac gp67-VEGF2) with the VEGF2 gene using the enzymes BamH1 and XbaI. The sequence of the cloned fragment was confirmed by DNA sequencing.

5 µg of the plasmid pBac gp67-VEGF2 was cotransfected with 1.0 µg of a commercially available linearized baculovirus ("BaculoGold™ baculovirus DNA", Pharmingen, San Diego, Calif.) using the lipofectin method (Feigner et al. Proc. Natl. Acad. Sci. USA, 84:7413-7417 (1987)).

1 µg of BaculoGold™ virus DNA and 5 µg of the plasmid pBac gp67-VEGF2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith, supra. As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the virus was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-gp67-VEGF2 at a multiplicity of infection (MOI) of 1. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

Figure 9:
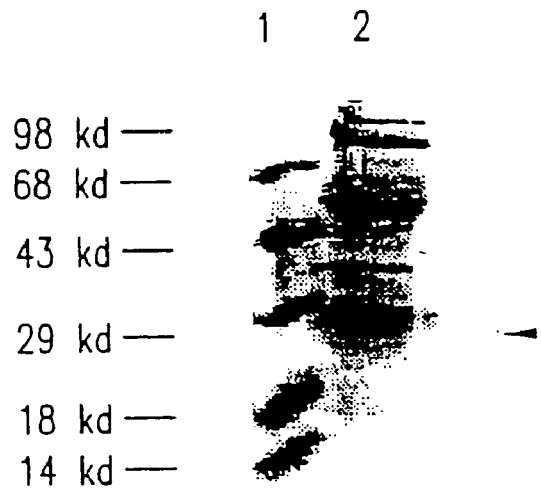
FIG. 9 depicts a photograph of an SDS-PAGE gel. The medium from Sf9 cells infected with a nucleic acid sequence of the present invention was precipitated. The resuspended precipitate was analyzed by SDS-PAGE and stained with coomassie brilliant blue.

Protein from the medium and cytoplasm of the Sf9 cells was analyzed by SDS-PAGE under non-reducing and reducing conditions. See FIGS. 8A and 8B, respectively. The medium was dialyzed against 50 mM MES, pH 5.8. Precipitates were obtained after dialysis and resuspended in 100 mM NaCitrate, pH 5.0. The resuspended precipitate was analyzed again by SDS-PAGE and was stained with Coomassie Brilliant Blue. See FIG. 9.

Figure 10:
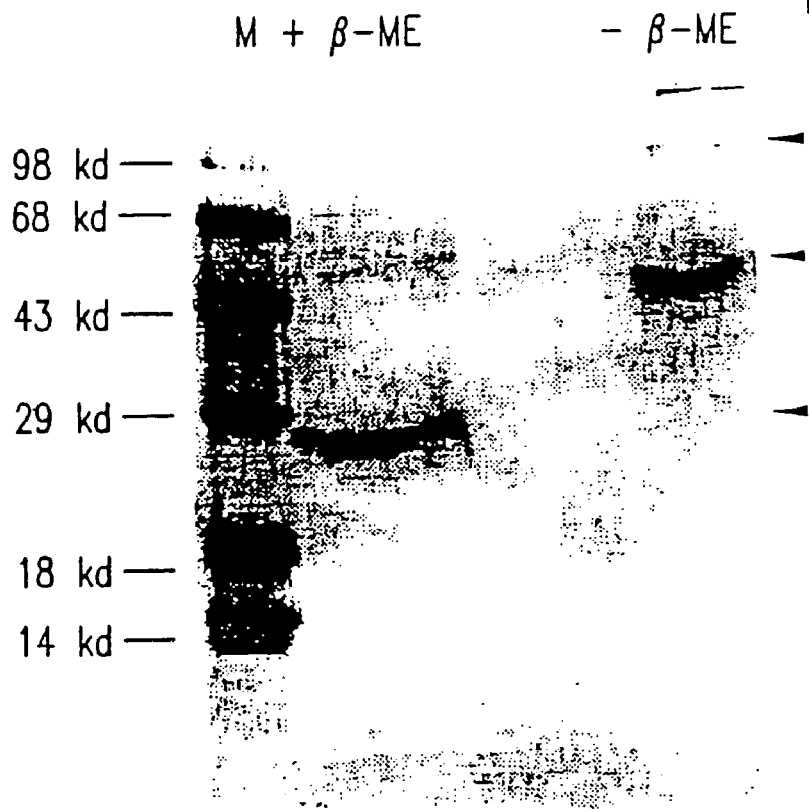
FIG. 10 depicts a photograph of an SDS-PAGE gel. VEGF2 was purified from the medium supernatant and analyzed by SDS-PAGE in the presence or absence of the reducing agent β-mercaptoethanol and stained by coomassie brilliant blue.
Figure 11:
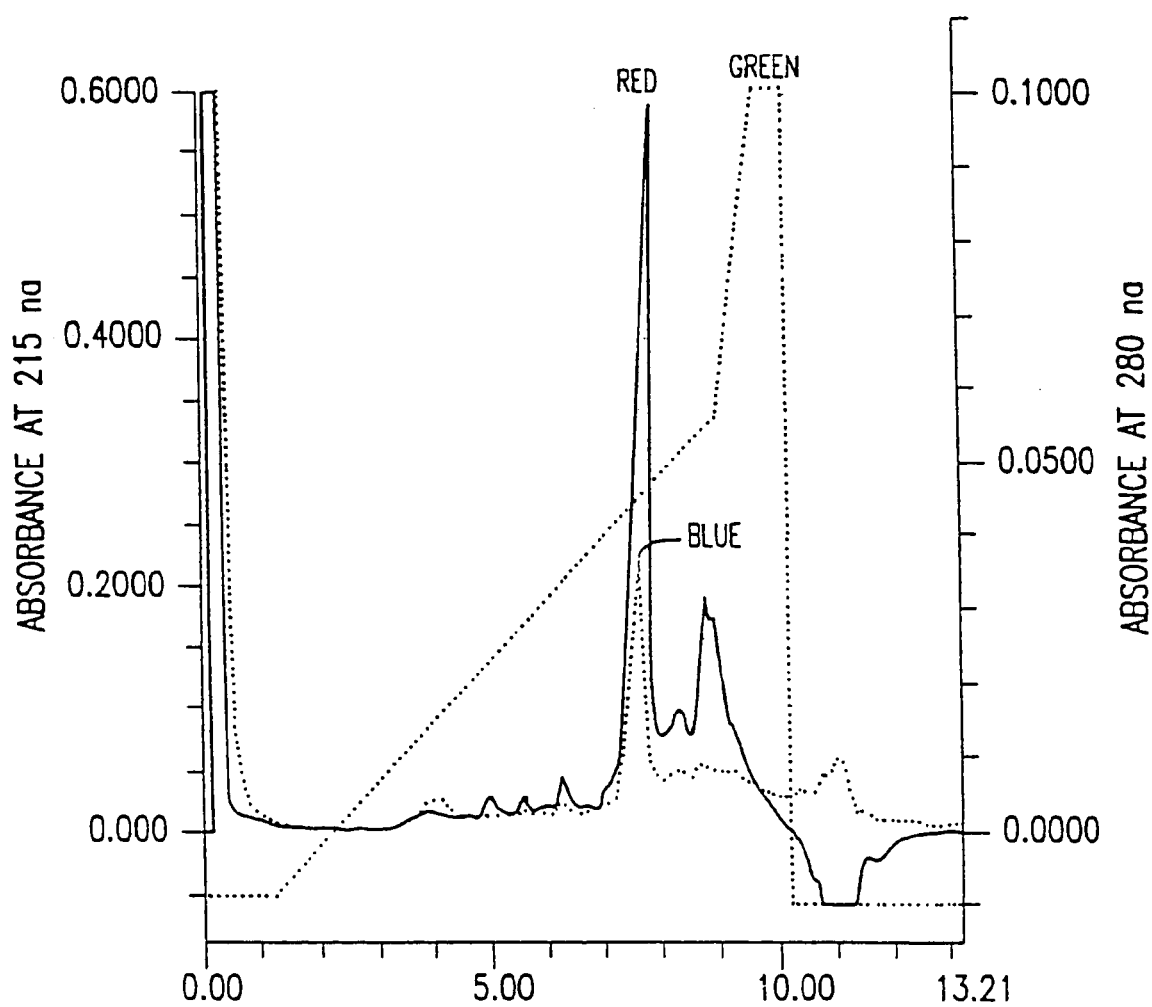
FIG. 11 depicts reverse phase HPLC analysis of purified VEGF2 using a RP-300 column (0.21×3 cm, Applied Biosystems, Inc.). The column was equilibrated with 0.1% trifluoroacetic acid (Solvent A) and the proteins eluted with a 7.5 min gradient from 0 to 60% Solvent B, composed of acetonitrile containing 0.07% TFA. The protein elution was monitored by absorbance at 215 nm ("red" line) and 280 nm ("blue" line). The percentage of Solvent B is shown by the "green" line.

The medium supernatant was also diluted 1:10 in 50 mM MES, pH 5.8 and applied to an SP-650M column (1.0×6.6 cm, Toyopearl) at a flow rate of 1 ml/min. Protein was eluted with step gradients at 200, 300 and 500 mM NaCl. The VEGF2 was obtained using the elution at 500 mM. The eluate was analyzed by SDS-PAGE in the presence or absence of reducing agent, β-mercaptoethanol and stained by Coommassie Brilliant Blue. See FIG. 10.

EXAMPLE 4

Expression of Recombinant VEGF2 in COS Cells

The expression of plasmid, VEGF2-HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire VEGF2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (Wilson et al., Cell 37:767 (1984)). The infusion of HA tag to the target protein allows easy detection of the recombinant protein with an antibody that recognizes the HA epitope.

The plasmid construction strategy is described as follows: The DNA sequence encoding VEGF2, ATCC No. 97149, was constructed by PCR using two primers: the 5' primer (CGC GGA TCC ATG ACT GTA CTC TAC CCA) (SEQ ID NO:14) contains a BamH1 site followed by 18 nucleotides of VEGF2 coding sequence starting from the initiation codon; the 3' sequence (CGC TCT AGA TCA AGC GTA GTC TGG GAC GTC GTA TGG GTA CTC GAG GCT CAT TTG TGG TCT 3') (SEQ ID NO:15) contains complementary sequences to an XbaI site, HA tag, XhoI site, and the last 15 nucleotides of the VEGF2 coding sequence (not including the stop codon). Therefore, the PCR product contains a BamHI site, coding sequence followed by an XhoI restriction endonuclease site and HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into *E. coli* strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant VEGF2, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the VEGF2-HA protein was detected by radiolabelling and immunoprecipitation method (E. Harlow and D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP40, 0.1% SDS, 1% NP40, 0.5% DOC, 50 mM Tris, pH 7.5) (Wilson et al., Cell 37:767 (1984)). Both cell lysate and culture media were precipitated with an HA specific monoclonal antibody. Proteins precipitated were analyzed on 15% SDS-PAGE gels.

EXAMPLE 5

The Effect of Partially Purified VEGF2 Protein on the Growth of Vascular Endothelial Cells On day 1, human umbilical vein endothelial cells (HUVEC) were seeded at $2-5\times10^4$ cells/35 mm dish density in M199 medium containing 4% fetal bovine serum (FBS), 16 units/ml hepanin, and 50 units/ml endothelial cell growth supplements (ECGS, Biotechnique, Inc.). On day 2, the medium was replaced with M199 containing 10% FBS, 8 units/ml heparin. VEGF2 protein of SEQ ID NO. 2 minus the initial 45 amino acid residues, (VEGF) and basic FGF (bFGF) were added, at the concentration shown. On days 4 and 6, the medium was replaced. On day 8, cell number was determined with a Coulter Counter (See FIG. 12).

EXAMPLE 6

The Effect of Purified VEGF2 Protein on the Growth of Vascular Endothelial Cells On day 1, human umbilical vein endothelial cells (HUVEC) were seeded at $2-5\times10^4$ cells/35 mm dish density in M199 medium containing 4% fetal bovine serum (FBS), 16 units/ml heparin, 50 units/ml endothelial cell growth supplements (ECGS, Biotechnique, Inc). On day 2, the medium was replaced with M199 containing 10% FBS, 8 units/ml heparin. Purified VEGF2 protein of SEQ ID NO:2 minus initial 45 amino acid residues was added to the medium at this point. On days 4 and 6, the medium was replaced with fresh medium and supplements. On day 8, cell number was determined with a Coulter Counter (See FIG. 13).

EXAMPLE 7

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed-to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA 7:219-225 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 8

Expression of VEGF2 mRNA in Human Fetal and Adult Tissues

Experimental Design

Northern blot analysis was carried out to examine the levels of expression of VEGF2 mRNA in human fetal and adult tissues. A cDNA probe containing the entire nucleotide sequence of the VEGF-2 protein was labeled with $^{32}$p using the rediprime* DNA labeling system (Amersham Life Science), according to the manufacturer's instructions. After labeling, the probe was purified using a CHROMA SPIN-100* column (Clontech Laboratories, Inc.), according to manufacturer's protocol number PT1200-T. The purified labeled probe was then used to examine various human tissues for VEGF-2 mRNA.

A Multiple Tissue Northern (MTN) blot containing various human tissues (Fetal Kidney, Fetal Lung, Fetal Liver, Brain, Kidney, Lung, Liver, Spleen, Thymus, Bone Marrow, Testes, Placenta, and Skeletal Muscle) was obtained from Clontech. The MTN blot was examined with the labeled probe using ExpressHyb* hybridization solution (Clontech) according to manufacturer's protocol number PT1190-1. Following hybridization and washing, the blot was exposed to film at −70° C. overnight with an intensifying screen and developed according to standard procedures.

Results

Figure 14A:
FIGS. 14A-14B depict expression of VEGF2 mRNA in human fetal and adult tissues.
Figure 14B:

Expression of VEGF2 mRNA is abundant in vascular smooth muscle and several highly vascularized tissues. VEGF2 is expressed at significantly higher levels in tissues associated with hematopoetic or angiogenic activities, i.e. fetal kidney, fetal lung, bone marrow, placental, spleen and lung tissue. The expression level of VEGF2 is low in adult kidney, fetal liver, adult liver, testes; and is almost undetectable in fetal brain, and adult brain (See FIG. 14).

Figure 15:
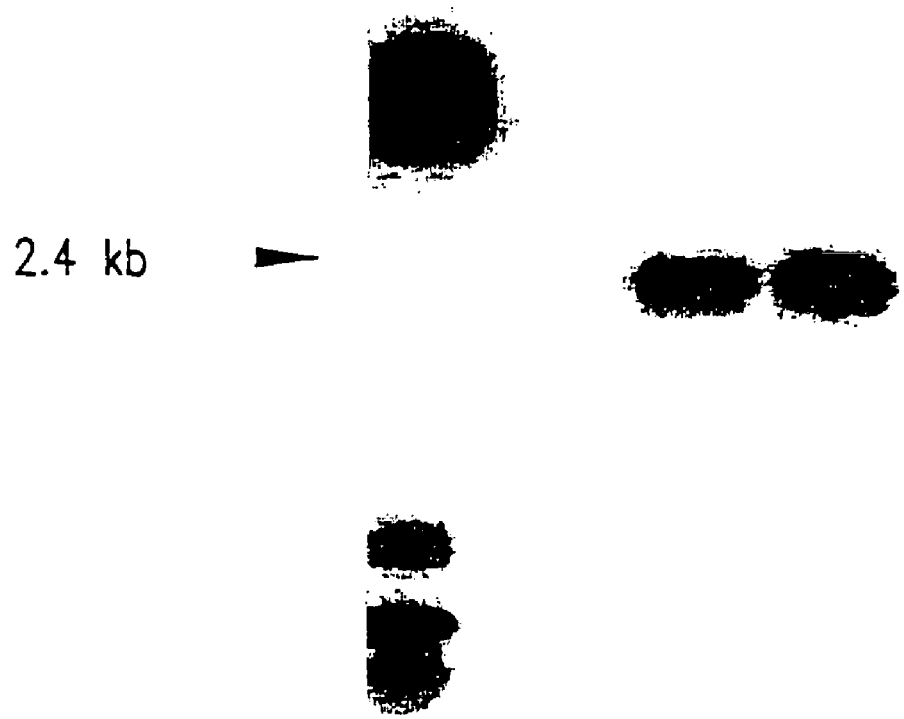
FIG. 15 depicts expression of VEGF2 mRNA in human primary culture cells.

In primary cultured cells, the expression of VEGF-2 mRNA is abundant in vascular smooth muscle cells and dermal fibroblast cells, but much lower in human umbilical vein endothelial cells (see FIG. 15). This mRNA distribution pattern is very similar to that of VEGF.

EXAMPLE 9

Construction of Amino Terminal and Carboxy Terminal Deletion Mutants

In order to identify and analyze biologically active VEGF-2 polypeptides, a panel of deletion mutants of VEGF-2 was constructed using the expression vector pHE4a.

1. Construction of VEGF-2 T103-L215 in pHE4

To permit Polymerase Chain Reaction directed amplification and sub-cloning of VEGF-2 T103-L215 (amino acids 103 to 215 in FIG. 1 or SEQ ID NO:18) into the *E. coli* protein expression vector, pHE4, two oligonucleotide primers complementary to the desired region of VEGF2 were synthesized with the following base sequence:

5' Primer (Nde 1/START and 18 nt of coding sequence):

(SEQ ID NO:19)
5'-GCA GCA CAT ATG ACA GAA GAG ACT ATA AAA-3'

3' Primer (Asp718, STOP, and 15 nt of coding sequence):

```
                                          (SEQ ID NO:20)
5'-GCA GCA GGT ACC TCA CAG TTT AGA CAT GCA-3'
```

The above described 5' primer (SEQ ID NO: 19), incorporates an NdeI restriction site and the above described 3' Primer (SEQ ID NO:20), incorporates an Asp718 restriction site. The 5' primer (SEQ ID NO: 19) also contains an ATG sequence adjacent and in frame with the VEGF-2 coding region to allow translation of the cloned fragment in *E. coli*, while the 3'primer (SEQ ID NO:20) contains one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24419 in SEQ ID NO: 18) as, for example, constructed in Example 3 as template. The resulting amplicon was restriction digested with NdeI and Asp718 and subcloned into NdeI/Asp718 digested pHE4a expression vector.

2. Construction of VEGF-2 T103-R227 in pHE4

To permit Polymerase Chain Reaction directed amplification and sub-cloning of VEGF-2 T103-R227 (amino acids 103 to 227 in FIG. 1 or SEQ ID NO: 18) into the *E. coli* protein expression vector, pHE4, two oligonucleotide primers complementary to the desired region of VEGF2 were synthesized with the following base sequence:

5 5' Primer (Nde I/START and 18 nt of coding sequence):

```
                                          (SEQ ID NO:19)
5'-GCA GCA CAT ATG ACA GAA GAG ACT ATA AAA-3'
```

3' Primer (Asp 718, STOP, and 15 nt of coding sequence):

```
                                          (SEQ ID NO:21)
5'-GCA GCA GGT ACC TCA ACG TCT AAT AAT GGA-3'
```

In the case of the above described primers, an NdeI or Asp718 restriction site was incorporated he 5'primer and 3'primer, respectively. The 5'primer (SEQ ID NO:19) also contains an ATG sequence adjacent and in frame with the VEGF-2 coding region to allow translation of the cloned fragment in *E. coli*, while the 3' Primer (SEQ ID NO:21) contains one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24-419 in SEQ ID NO:18) as, for example, constructed in Example 3, as template. The resulting amplicon was restriction digested with NdeI and Asp718 and subcloned into NdeI/Asp718 digested pHE4a protein expression vector.

3. Construction of VEGF-2 T103-L215 in pA2GP

In this illustrative example, the plasmid shuttle vector pA2 GP is used to insert the cloned DNA encoding the N-terminal and C-terminal deleted VEGF-2 protein (amino acids 103-215 in FIG. 1 or SEQ ID NO:18), into a baculovirus to express the N-terminal and C-terminal deleted VEGF-2 protein, using a baculovirus leader and standard methods as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

The cDNA sequence encoding the VEGF-2 protein without 102 amino acids at the N-terminus and without 204 amino acids at the C-terminus in FIG. 1, was amplified using PCR oligonucleotide primers corresponding to the 5' and 3' sequences of the gene.

The 5' primer has the sequence 5'-GCA GCA GGA TCC CAC AGA AGA GAC TAT AAA-3' (SEQ ID NO:22) containing the BamHI restriction enzyme site (in bold) followed by 1 spacer nt to stay in-frame with the vector-supplied signal peptide, and 17 nt of coding sequence bases of VEGF-2 protein. The 3' primer has the sequence 5'-GCA GCA TCT AGA TCA CAG TTT AGA CAT GCA-3' (SEQ ID NO:23) containing the XbaI restriction site (in bold) followed by a stop codon and 17 nucleotides complementary to the 3' coding sequence of VEGF-2.

The amplified sequences were isolated from a 1% agarose gel using a commercially available kit ("Geneclean," BIO 101, Inc., La Jolla, Calif.). The fragment was then digested with the endonuclease BamHI and XbaI and then purified again on a 1% agarose gel. This fragment was ligated to pA2 GP baculovirus transfer vector (Supplier) at the BamH1 and Xba1 sites. Through this ligation, VEGF2 cDNA representing the N-terminal and C-terminal deleted VEGF-2 protein (amino acids 103-215 in FIG. 1 or SEQ ID NO: 18) was cloned in frame with the signal sequence of baculovirus GP gene and was located at the 3' end of the signal sequence in the vector. This is designated pA2GPVEGF2. T103-L215.

4. Construction of VEGF-2 T103-R27 in pA2GP

The cDNA sequence encoding the VEGF-2 protein without 102 amino acids at the N-terminus and without 192 amino acids at the C-terminus in FIG. 1 (i.e., amino acids 103-227 of SEQ ID NO: 18) was amplified using PCR oligonucleotide primers corresponding to the 5' and 3' sequences of the gene.

The 5'-GCA GCA GGA TCC CAC AGA AGA GAC TAT AAA ATT TGC TGG-3' primer has the sequence (SEQ ID NO:24) containing the BamHI restriction enzyme site (in bold) followed by 1 spacer nt to stay in-frame with the vector-supplied signal peptide, and 26 nt of coding sequence bases of VEGF-2 protein. The 3'primer has the sequence 5'-GCA GCA TCT AGA TCA ACG TCT AAT AAT GGA ATG AAC- 3' (SEQ ID NO:25) containing the Xba1 restriction site (in bold) followed by a stop codon and 21 nucleotides complementary to the 3' coding sequence of VEGF-2.

The amplified sequences were isolated from a 1% agarose gel using a commercially available kit ("Geneclean," BIO 101, Inc., La Jolla, Calif.). The fragment was then digested with the endonuclease BamH1 and XbaI and then purified again on a 1% agarose gel. This fragment was ligated to pA2 GP baculovirus transfer vector (Supplier) at the BamH1 and XbaI sites. Through this ligation, VEGF2 cDNA representing the N-terminal and C-terminal deleted VEGF-2 protein (amino acids 103-227 in FIG. 1 or SEQ ID NO:18) was cloned in frame with the signal sequence of baculovirus GP gene and was located at the 3' end of the signal sequence in the vector. This construct is designated pA2GPVEGF2.T103-R227.

5. Construction of VEGF-2 in pC1

The expression vectors pC1 and pC4 contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

The vector pC1 is used for the expression of VEGF-2 protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R T., 1978, J. Biol. Chem. 253: 1357-1370, Hamlin, J. L. and Ma, C. 1990, Biochem. et Biophys. Acta, 1097:107-143, Page, M. J. and Sydenham, M. A. 1991, Biotechnology Vol. 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438-4470) plus a fragment isolated from the enhancer of the immediate early gene of human cytomegalovirus (CMV) (Boshart et al., Cell 41:521-530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding VEGF-2, ATCC Accession No. 97149, was constructed by PCR using two primers corresponding to the 5' and 3' ends of the VEGF-2 gene: the 5' Primer (5'-GAT CGA TCC ATC ATG CAC TCG CTG GGC TTC TTC TCT GTG GCG TGT TCT CTG CTC G-3' (SEQ ID NO:26)) contains a Klenow-filled BamHI site and 40 nt of VEGF-2 coding sequence starting from the initiation codon; the 3' primer (5'-GCA GGG TAC GGA TCC TAG ATT AGC TCA TTF GTG GTC TTT-3' (SEQ ID NO:27)) contains a BamHI site and 16 nt of VEGF-2 coding sequence not including the stop codon.

The PCR amplified DNA fragment is isolated from a 1% agarose gel as described above and then digested with the endonuclease BamHI and then purified again on a 1% agarose gel. The isolated fragment and the dephosphorylated vector are then ligated with T4 DNA ligase. *E. coli* HB101 cells are then transformed and bacteria identified that contained the plasmid pC1. The sequence and orientation of the inserted gene is confirmed by DNA sequencing. This construct is designated pC1VEGF-2.

6. Construction of pC4SigVEGF-2 T103-L215

Insert Description for pC4Sig

Plasmid pC4Sig is plasmid pC4 (Accession No. 209646) containing a human IgG Fc portion as well as a protein signal sequence.

To permit Polymerase Chain Reaction directed amplification and sub-cloning of VEGF-2 T103-L215 (amino acids 103 to 215 in FIG. 1 or SEQ ID NO:18) into pC4Sig, two oligonucleotide primers complementary to the desired region of VEGF2 were synthesized with the following base sequence:

5' Primer (Bam HI and 26 nt of coding sequence):

```
                                       SEQ ID NO:34
  5'-GCA GCA GGA TCC ACA GAA GAG ACT ATA AAA TTT

GCT GC-3'
```

3' Primer (Xba I, STOP, and 15 nt of coding sequence):

```
                                       SEQ ID NO:35
  5'-CGT CGT TCT AGA TCA CAG TTT AGA CAT GCA TCG

GCA G-3'
```

The Polymerase Chain Reaction was performed using standard conditions well known to those skilled in the art and the nucleotide sequence for the mature VEGF-2 (aa 24-419) as, for example, constructed in Example 3, as template. The resulting amplicon was restriction digested with BamHI and XbaI and subcloned into BamHI/XbaI digested pC4Sig vector.

7. Construction of pC4SigVEGF-2 T103-R227

To permit Polymerase Chain Reaction directed amplification and sub-cloning of VEGF-2 T103-L215 (amino acids 103 to 227 in FIG. 1 or SEQ ID NO:18) into pC4Sig, two oligonucleotide primers complementary to the desired region of VEGF2 were synthesized with the following base sequence:

5' Primer (Bam HI and 26 nt of coding sequence):

```
                                       SEQ ID NO:34
5'-GCA GCA GGA TCC ACA GAA GAG ACT ATA AAA TTT

GCT GC-3'
```

3' Primer (Xba I, STOP, and 21 nt of coding sequence):

```
                                       SEQ ID NO:25
5'-GCA GCA TCT AGA TCA ACG TCT AAT AAT GGA ATG

AAC-3'
```

The Polymerase Chain Reaction was performed using standard conditions well known to those skilled in the art and the nucleotide sequence for the mature VEGF-2 (aa 24-419) as, for example, constructed in Example 3, as template. The resulting amplicon was restriction with BamHI and XbaI and subcloned into BamHI/XbaI digested pC4Sig vector.

8. Construction of pC4VEGF-2 M1-M263

The expression vector pC4 contains the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vector contains in addition the 3' intron, the polyadenylation and termination signal of the rat preproinsulin gene.

In this illustrative example, the cloned DNA encoding the C-terminal deleted VEGF-2 M1-M263 protein (amino acids 1-263 in FIG. 1 or SEQ ID NO:18) is inserted into the plasmid vector pC4 to express the C-terminal deleted VEGF-2 protein.

To permit Polymerase Chain Reaction directed amplification and sub-cloning of VEGF-2 M1-M263 into the expression vector, pC4, two oligonucleotide primers complementary to the desired region of VEGF2 were synthesized with the following base sequence:

```
                                        (SEQ ID NO:28)
5' Primer
5'-GAC TGG ATC CGC CAC CAT GCA CTC GCT GGG GTT

CTT CTC-3'

(SEQ ID NO:29)
3' Primer
5'-GAC TGG TAC CTT ATC ACA TAA AAT CTT CCT

GAG CC-3'
```

In the case of the above described 5' primer, an BamH1 restriction site was incorporated, while in the case of the 3' primer, an ASP718 restriction site was incorporated. The 5' primer also contains 6 nt, 20 nt of VEGF-2 coding sequence, and an ATG sequence adjacent and in frame with the VEGF-2 coding region to allow translation of the cloned fragment in *E. coli,* while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli.*

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction with BamH1 and Asp718 and subcloned into BamHI/Asp718 digested pC4 protein expression vector. This construct is designated pC4VEGF-2 M1-M263.

9. Construction of pC4VEGF-2 M1-D311

In this illustrative example, the cloned DNA encoding the C-terminal deleted VEGF-2 M1-D311 protein (amino acids 1-311 in FIG. 1 or SEQ ID NO:18) is inserted into the plasmid vector pC4 to express the C-terminal deleted VEGF-2 protein.

To permit Polymerase Chain Reaction directed amplification and sub-cloning of VEGF-2 M1-D311 into the expression vector, pC4, two oligonucleotide primers complementary to the desired region of VEGF2 were synthesized with the following base sequence:

```
                                        (SEQ ID NO:30)
5' Primer
5'-GAC TGG ATC CGC CAC CAT GCA CTC GCT GGG CTT

CTT CTC-3'

(SEQ ID NO:31)
3' Primer
5'-GAC TGG TAC CTT ATC AGT CTA GTT CTT TGT

GGG G-3'
```

In the case of the above described 5' primer, an BamH1 restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in *E. coli,* while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli.*

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamH1 and Asp718 and subcloned into BamH1/Asp718 digested pC4 protein expression vector.

10. Construction of pC4VEGF-2 M1-Q367

In this illustrative example, the cloned DNA encoding the C-terminal deleted VEGF-2 M1-D311 protein (amino acids 1-311 in SEQ ID NO:18) is inserted into the plasmid vector pC4 to express the C-terminal deleted VEGF-2 protein.

To permit Polymerase Chain Reaction directed amplification and sub-cloning of VEGF-2 M1-D311 into the expression vector, pC4, two oligonucleotide primers complementary to the desired region of VEGF2 were synthesized with the following base sequence:

```
5' Primer
                                                (SEQ ID NO:32)
5'-GAC TGG ATC CGC CAC CAT GCA CTC GCT GGG CTT
CTT CTC-3'

3' Primer
                                                (SEQ ID NO:33)
5'-GAG TGG TAC CTC ATT ACT GTG GAC TTT CTG TAC
ATT C-3'
```

In the case of the above described 5' primer, an BamH1 restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in E. coli, while the 3' primer contains 2 nt, 20 nt of VEGF-2 coding sequence, and one stop codon (preferentially utilized in E. coli) adjacent and in frame with the VEGF-2 coding region which ensures correct translational termination in E. coli.

The Polymerase Chain Reaction was performed using standard conditions well known to those skilled in the art and the nucleotide sequence for the mature VEGF-2 (aa 24419) as constructed, for example, in Example 3 as template. The resulting amplicon was restriction digested with BamH1 and Asp718 and subcloned into BamH1/Asp718 digested pC4 protein expression vector. This construct is designated pC4VEGF-2 M1-Q367.

EXAMPLE 10

Transient Expression of VEGF-2 Protein in COS-7 Cells

Experimental Design

Expression of the VEGF-2-HA fusion protein from the construct made in Example 4, for example, was detected by radiolabeling and immunoprecipitation, using methods described in, for example Harlow and colleagues (Antibodies: A Laboratory Manual, 2nd Ed.; Cold Spring Harbor Laboratory Press, Cold Spring Harbor, N.Y. (1988)). To this end, two days after transfection, the cells were labeled by incubation in media containing 35S-cysteine for 8 hours. The cells and the media were collected, and the cells were washed and then lysed with detergent-containing RIPA buffer: 150 mM NaCl, 1% NP-40, 0.1% SDS, 1% NP-40, 0.5% DOC, 50 mM TRIS, pH 7.5, described by Wilson and colleagues (supra). Proteins were precipitated from the cell lysate and from the culture media using an HA-specific monoclonal antibody. The precipitated proteins then were analyzed by SDS-PAGE and autoradiography.

Results

Figure 16A:
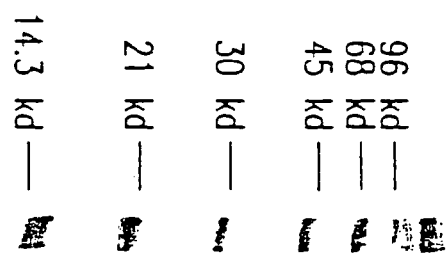
FIGS. 16A-16B depict transient expression of VEGF2 protein in COS-7 cells.
Figure 16B:
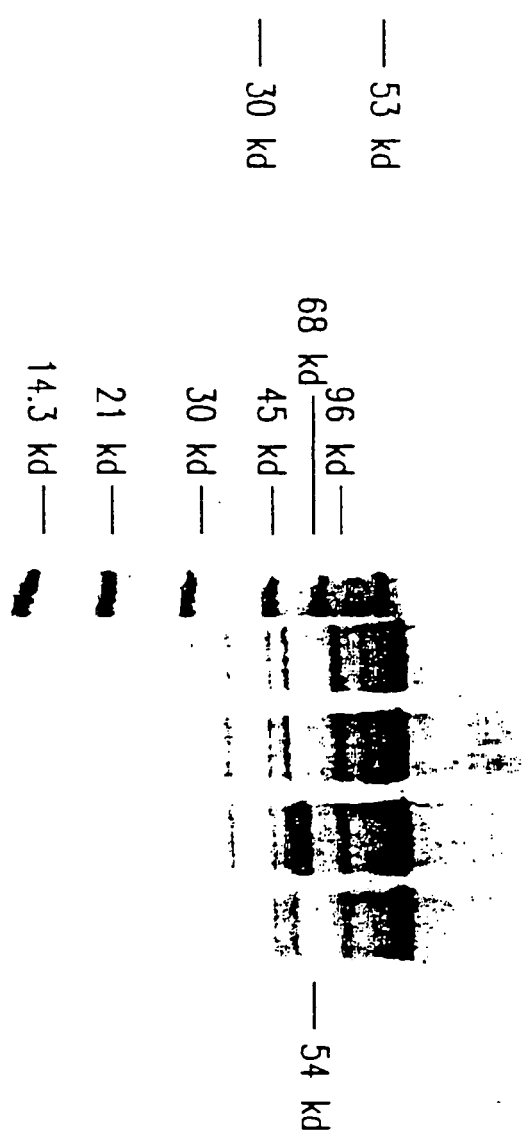

As shown in FIG. 16, cells transfected with pcDNA1 VEGF-2HA secreted a 56 kd and a 30 kd protein. The 56 kd protein, but not the 30 kd protein, could also be detected in the cell lysate but is note detected in controls. This suggests the 30 kd protein is likely to result from cleavage of the 56 kd protein. Since the HA-tag is on the C-terminus of VEGF-2, the 30 kd protein must represent the C-terminal portion of the cleaved protein, whereas the N-terminal portion of the cleaved protein would not be detected by immunoprecipitation. These data indicate that VEGF-2 protein expressed in mammalian cells is secreted and processed.

EXAMPLE 11

Stimulatory Effect of VEGF2 on Proliferation of Vascular Endothelial Cells

Experimental Design

Expression of VEGF2 is abundant in highly vascularized tissues. Therefore the role of VEGF2 in regulating proliferation of several types of endothelial cells was examined.

Endothelial Cell Proliferation Assay

For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells were seeded in a 96-well plate (5,000 cells/well) in 0.1 mL serum-supplemented medium and allowed to attach overnight. After serum-starvation for 12 hours in 0.5% FBS, conditions (bFGF, VEFG$_{165}$ or VEFG-2 in 0.5% FBS) with or without Heparin (8 U/ml) were added to wells for 48 hours. 20 μg of MTS/PMS mixture (1:0.05) were added per well and allowed to incubate for 1 hour at 37° C. before measuring the absorbance at 490 nm in an ELISA plate reader. Background absorbance from control wells (some media, no cells) was subtracted, and seven wells were performed in parallel for each condition. See, Leak et al. In Vitro Cell. Dev. Biol. 30A:512-518 (1994)

Results

Figure 17:
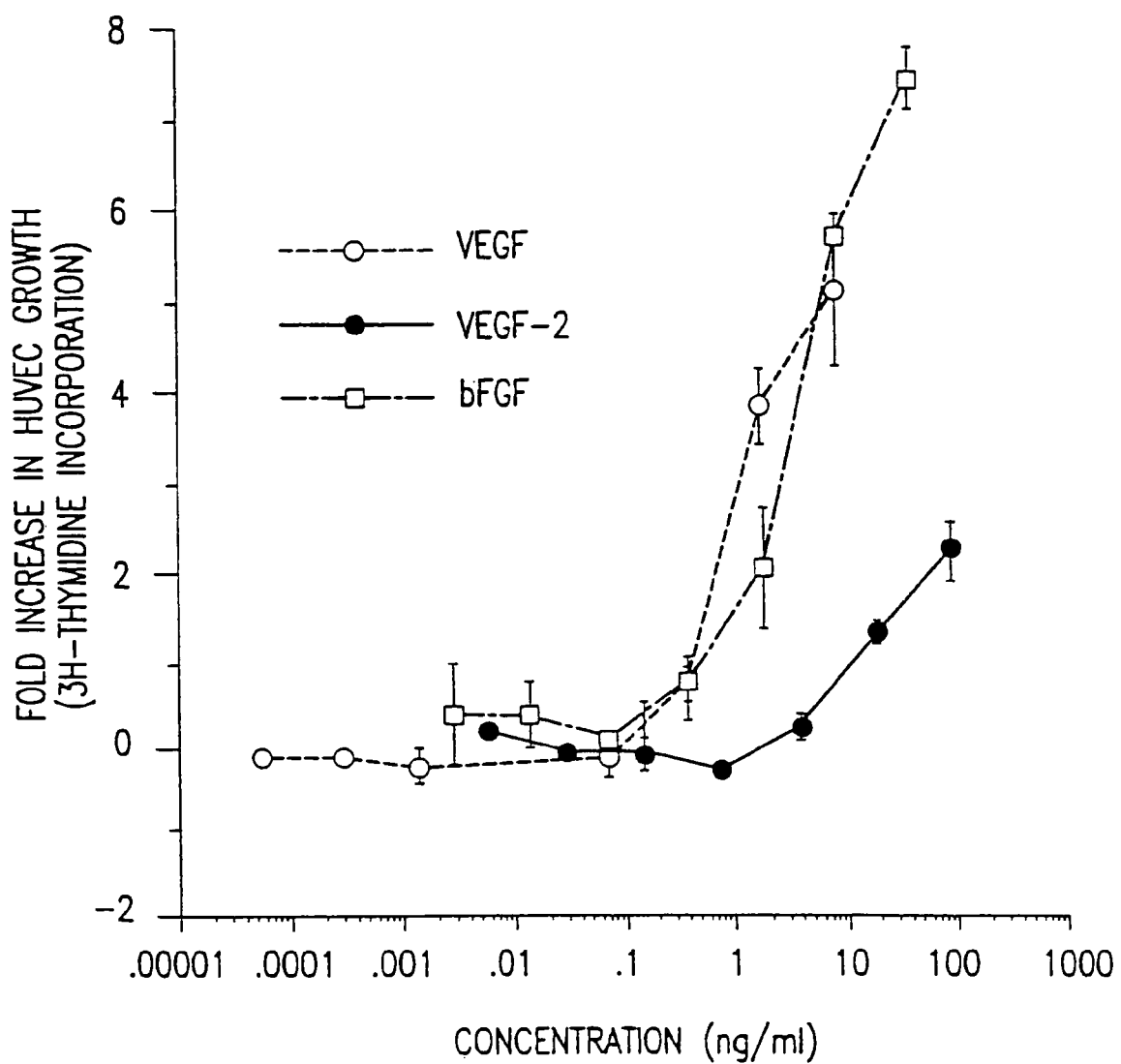
FIG. 17 depicts VEGF2 stimulated proliferation of human umbilical vein endothelial cells (HUVEC).
Figure 18:
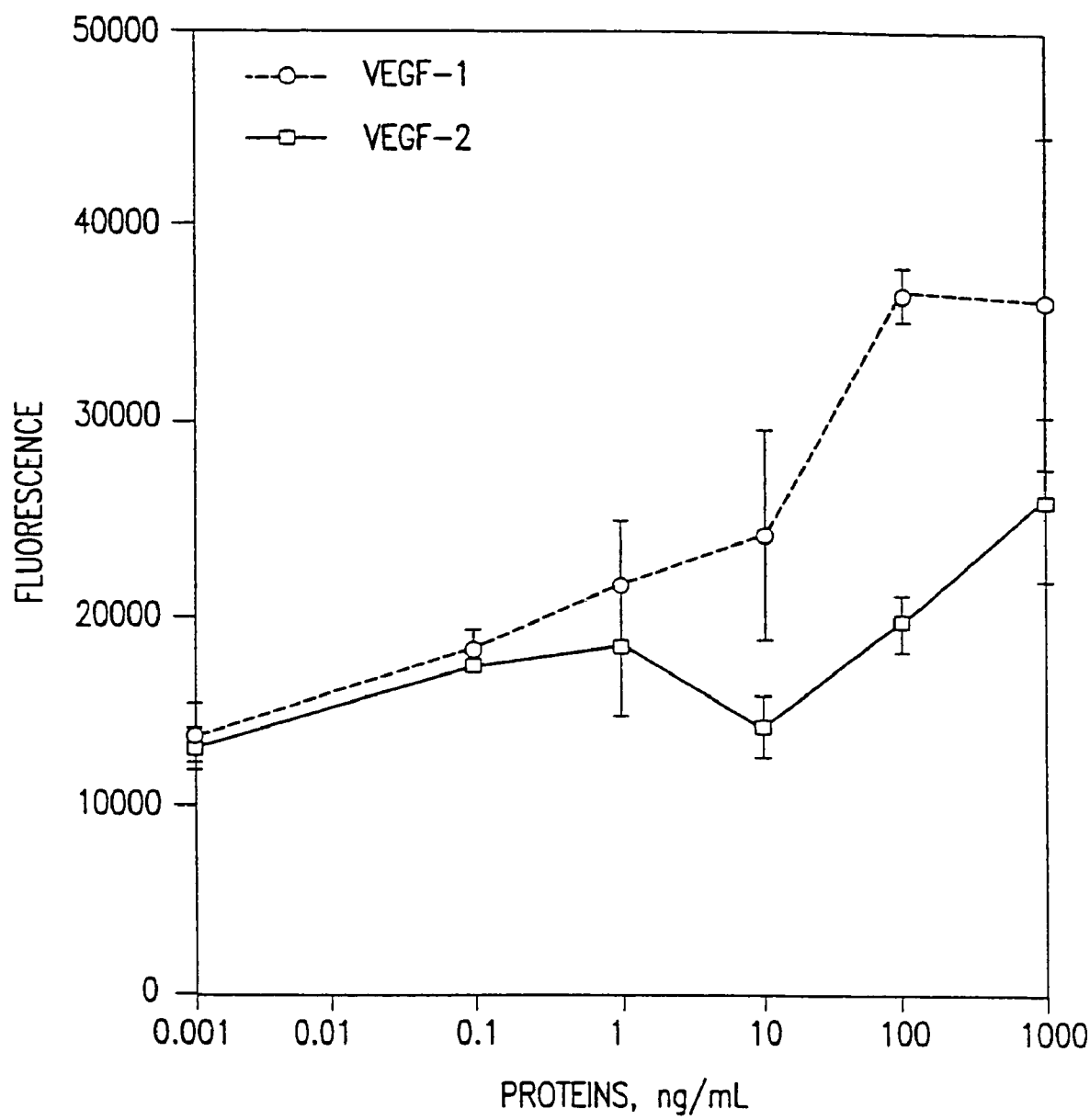
FIG. 18 depicts VEGF2 stimulated proliferation of dermal microvascular endothelial cells.
Figure 19:
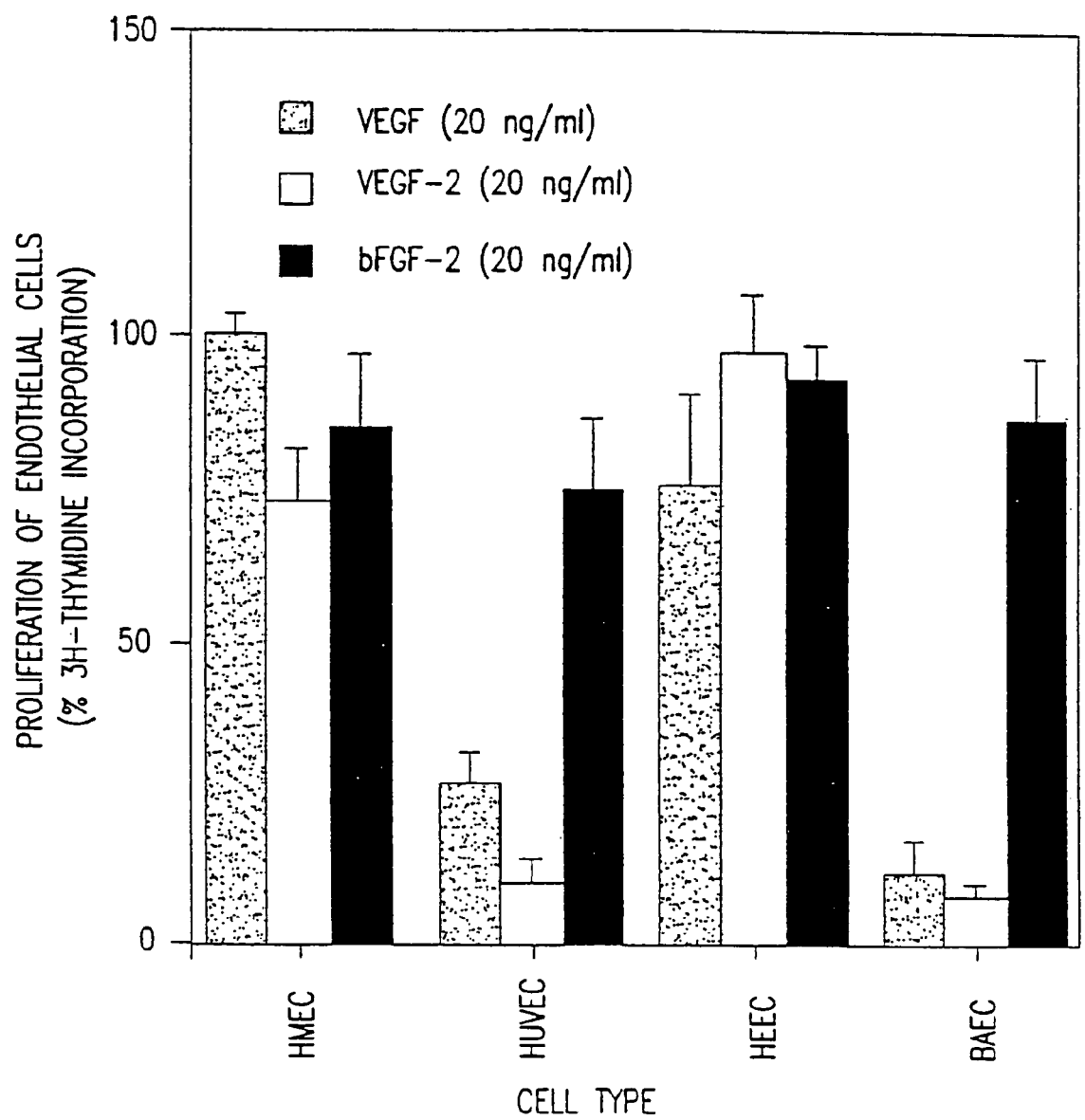
FIG. 19 depicts the stimulatory effect of VEGF2 on proliferation of microvascular, umbilical cord, endometrial, and bovine aortic endothelial cells.

VEGF2 stimulated proliferation of human umbilical vein endothelial cells (HUVEC) and dermal microvascular endothelial cells slightly (FIGS. 17 and 18). The stimulatory effect of VEGF2 is more pronounced on proliferation of endometrial and microvascular endothelial cells (FIG. 19). Endometrial endothelial cells (HEEC) demonstrated the greatest response to VEGF2 (96% of the effect of VEGF on microvascular endothelial cells). The response of microvascular endothelial cells (HMEC) to VEGF2 was 73% compared to VEGF. The response of HUVEC and BAEC (bovine aortic endothelial cells) to VEGF2 was substantially lower at 10% and 7%, respectively. The activity of VEGF2 protein has varied between different purification runs with the stimulatory effect of certain batches on HUVEC proliferation being significantly higher than that of other batches.

EXAMPLE 12

Inhibition of PDGF-induced Vascular Smooth Muscle Cell Proliferation

VEGF2 expression is high in vascular smooth muscle cells. Smooth muscle is an important therapeutic target for vascular diseases, such as restenosis. To evaluate the potential effects of VEGF2 on smooth muscle cells, the effect of VEGF2 on human aortic smooth muscle cell (HAoSMC) proliferation was examined.

Experimental Design

HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 μg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after exposing to denaturing solution and then with the streptavidin-peroxidase and diaminobenzidine. After counterstining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6; 271(36):21985-21992 (1996).

Results

Figure 20A:
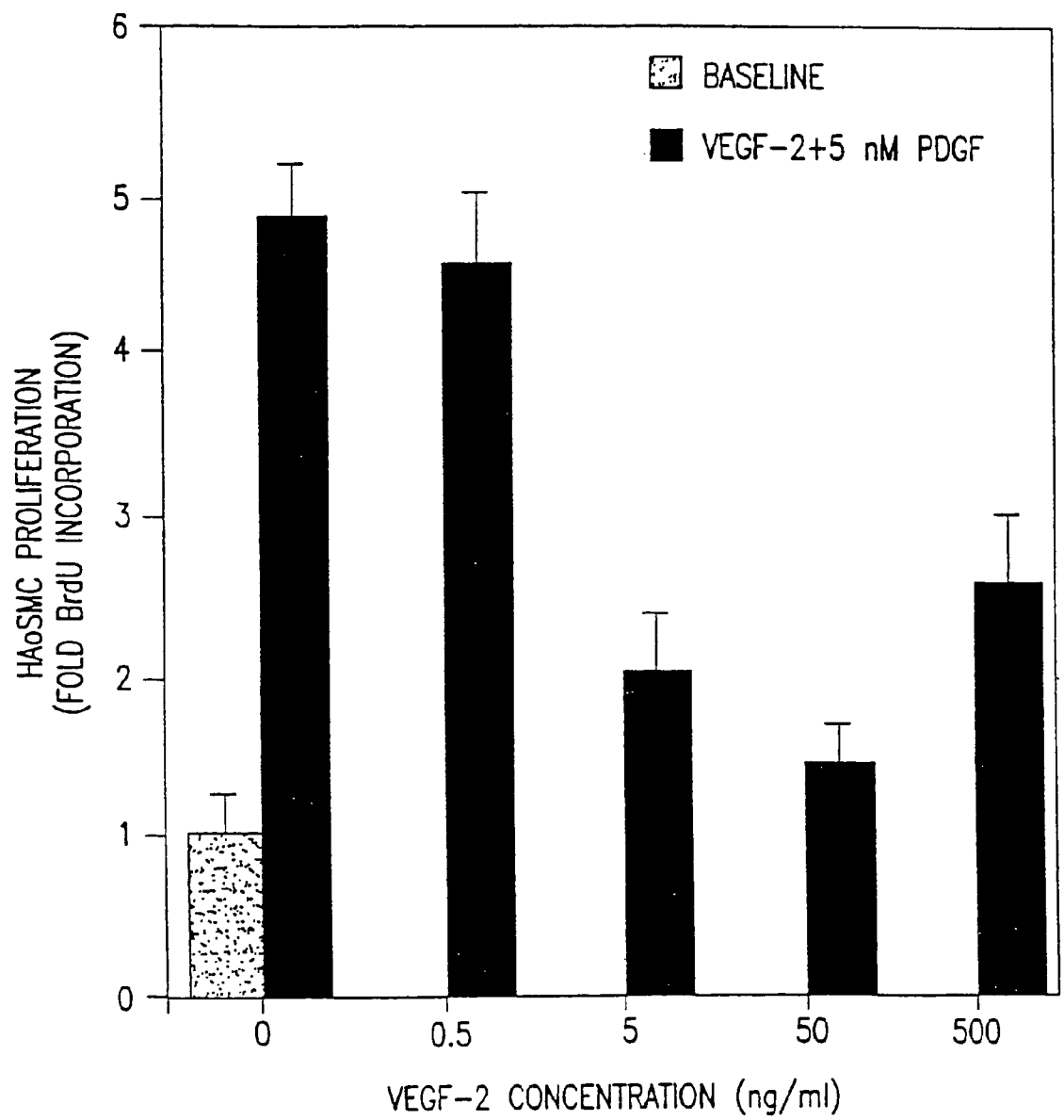
FIGS. 20A-20B depict inhibition of PDGF-induced vascular (human aortic) smooth muscle cell proliferation.
Figure 20B:
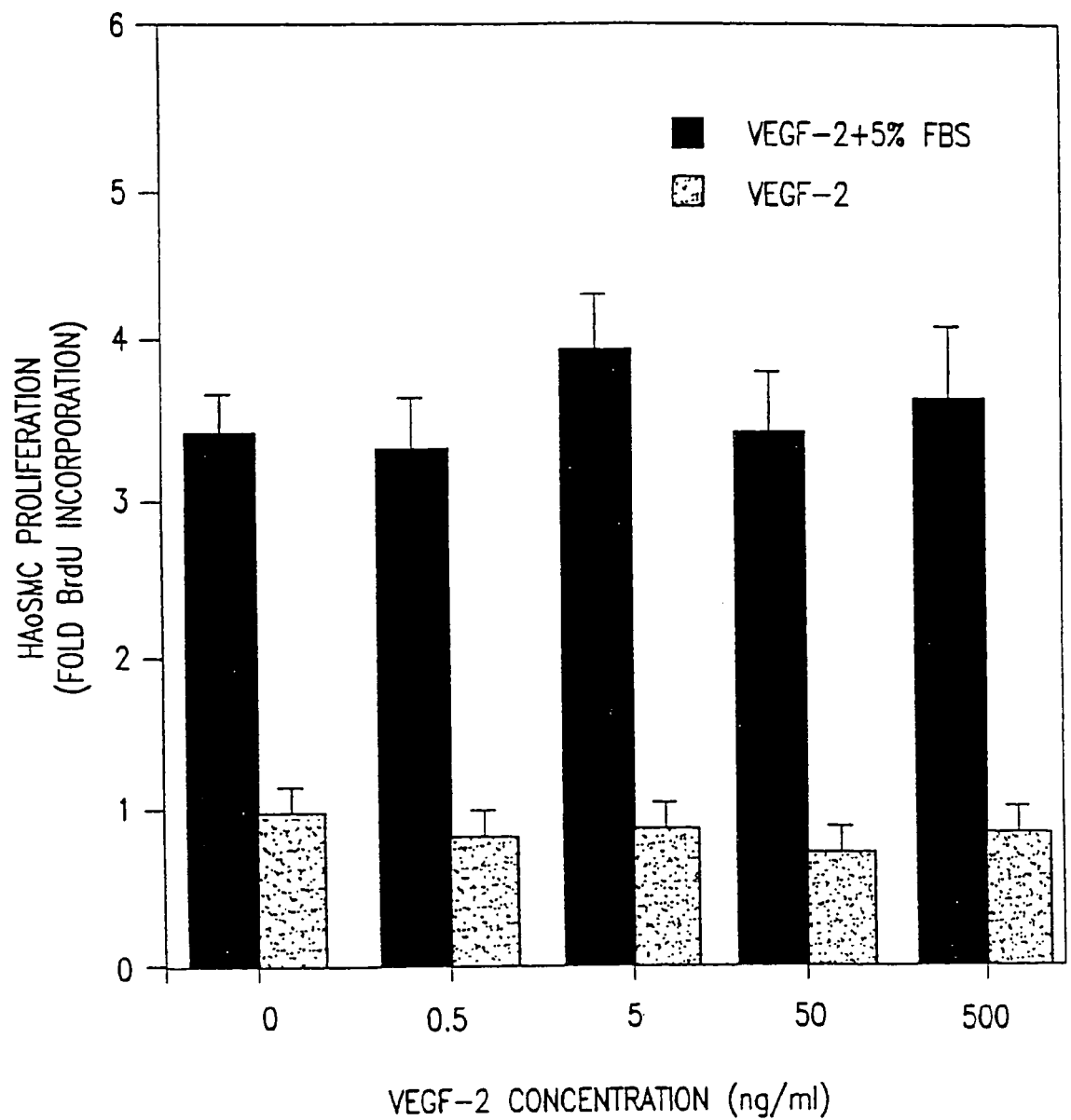

VEGF2 has an inhibitory effect on proliferation of vascular smooth muscle cells induced by PDGF, but not by Fetal Bovine Serum (FBS) (FIG. 20).

EXAMPLE 13

Stimulation of Endothelial Cell Migration

Endothelial cell migration is an important step involved in angiogenesis.

Experimental Design

This example will be used to explore the possibility that VEGF-2 may stimulate lymphatic endothelial cell migration. Currently, there are no published reports of such a model. However, we will be adapting a model of vascular endothelial cell migration for use with lymphatic endothelial cells essentially as follows:

Endothelial cell migration assays are performed using a 48 well microchemotaxis chamber (Neuroprobe Inc., Cabin John, M D; Falk, W., Goodwin, R. H. J., and Leonard, E. J. "A 48 well micro chemotaxis assembly for rapid and accurate measurement of leukocyte migration." J. Immunological Methods 1980; 33:239-247). Polyvinylpyrrolidone-free polycarbonate filters with a pore size of 8 urn (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2-6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37?C in a humidified chamber with 5% $CO_2$ to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

Results

Figure 21A:
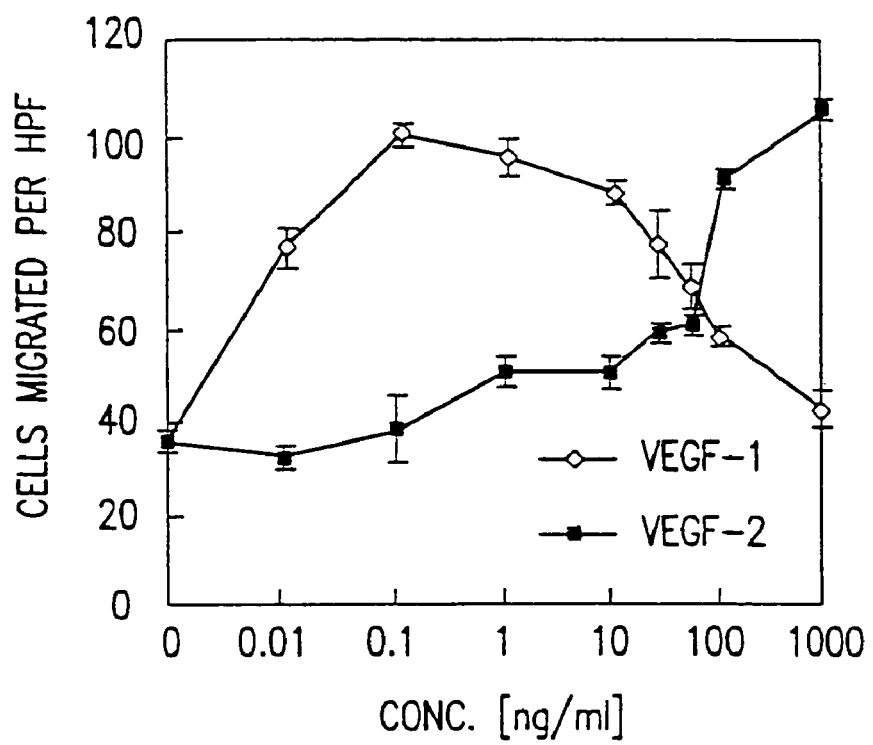
FIGS. 21A-21B depict stimulation of migration of HUVEC and bovine microvascular endothelial cells (BMEC) by VEGF-2.
Figure 21B:
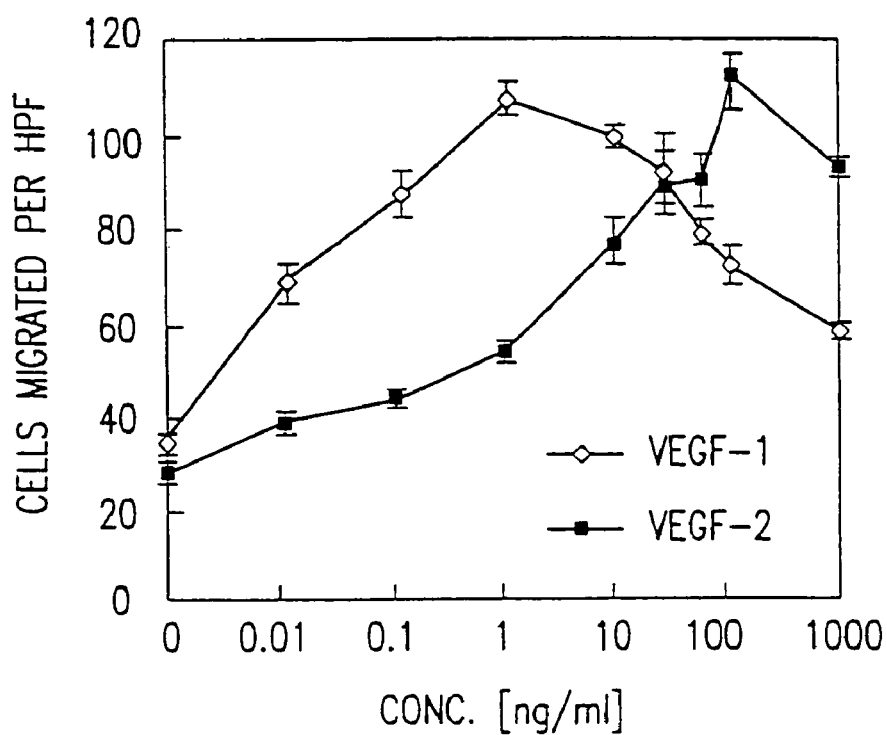

In an assay examining HUVEC migration using a 43-well microchemotaxis chamber, VEGF2 was able to stimulate migration of HUVEC (FIG. 21).

EXAMPLE 14

Stimulation of Nitric Oxide Production by Endothelial Cells

Nitric oxide released by the vascular endothelium is believed to be a mediator of vascular endothelium relaxation. VEGF-1 has been demonstrated to induce nitric oxide production by endothelial cells in response to VEGF-1. As a result, VEGF-2 activity can be assayed by determining nitric oxide production by endothelial cells in response to VEGF-2.

Experimental Design

Nitric oxide is measured in 96-well plates of confluent microvascular endothelial cells after 24 hours starvation and a subsequent 4 hr exposure to various levels of VEGF-1 and VEGF-2. Nitric oxide in the medium is determined by use of the Griess reagent to measure total nitrite after reduction of nitric oxide-derived nitrate by nitrate reductase. The effect of VEGF2 on nitric oxide release was examined on HUVEC.

Briefly, NO release from cultured HUVEC monolayer was measured with a NO-specific polarographic electrode connected to a NO meter (Iso-NO, World Precision Instruments Inc.) (1049). Calibration of the NO elements was performed according to the following equation:

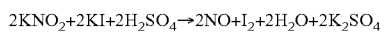

$$2KNO_2 + 2KI + 2H_2SO_4 \rightarrow 2NO + I_2 + 2H_2O + 2K_2SO_4$$

The standard calibration curve was obtained by adding graded concentrations of KNO2 (0, 5, 10, 25, 50, 100, 250, and 500 mmol/L) into the calibration solution containing KI and $H_2SO_4$. The specificity of the Iso-NO electrode to NO was previously determined by measurement of NO from authentic NO gas (1050). The culture medium was removed and HUVECs were washed twice with Dulbecco's phosphate buffered saline. The cells were then bathed in 5 ml of filtered Krebs-Henseleit solution in 6-well plates, and the cell plates were kept on a slide warmer (Lab Line Instruments Inc.) To maintain the temperature at 37° C. The NO sensor probe was inserted vertically into the wells, keeping the tip of the electrode 2 mm under the surface of the solution, before addition of the different conditions. S-nitroso acetyl penicillamin (SNAP) was used as a positive control. The amount of released NO was expressed as picomoles per $1 \times 10^6$ endothelial cells. All values reported were means of four to six measurements in each group (number of cell culture wells). See, Leak et al. Biochem. and Biophys. Res. Comm 217:96-105 (1995).

Results

Figure 22:
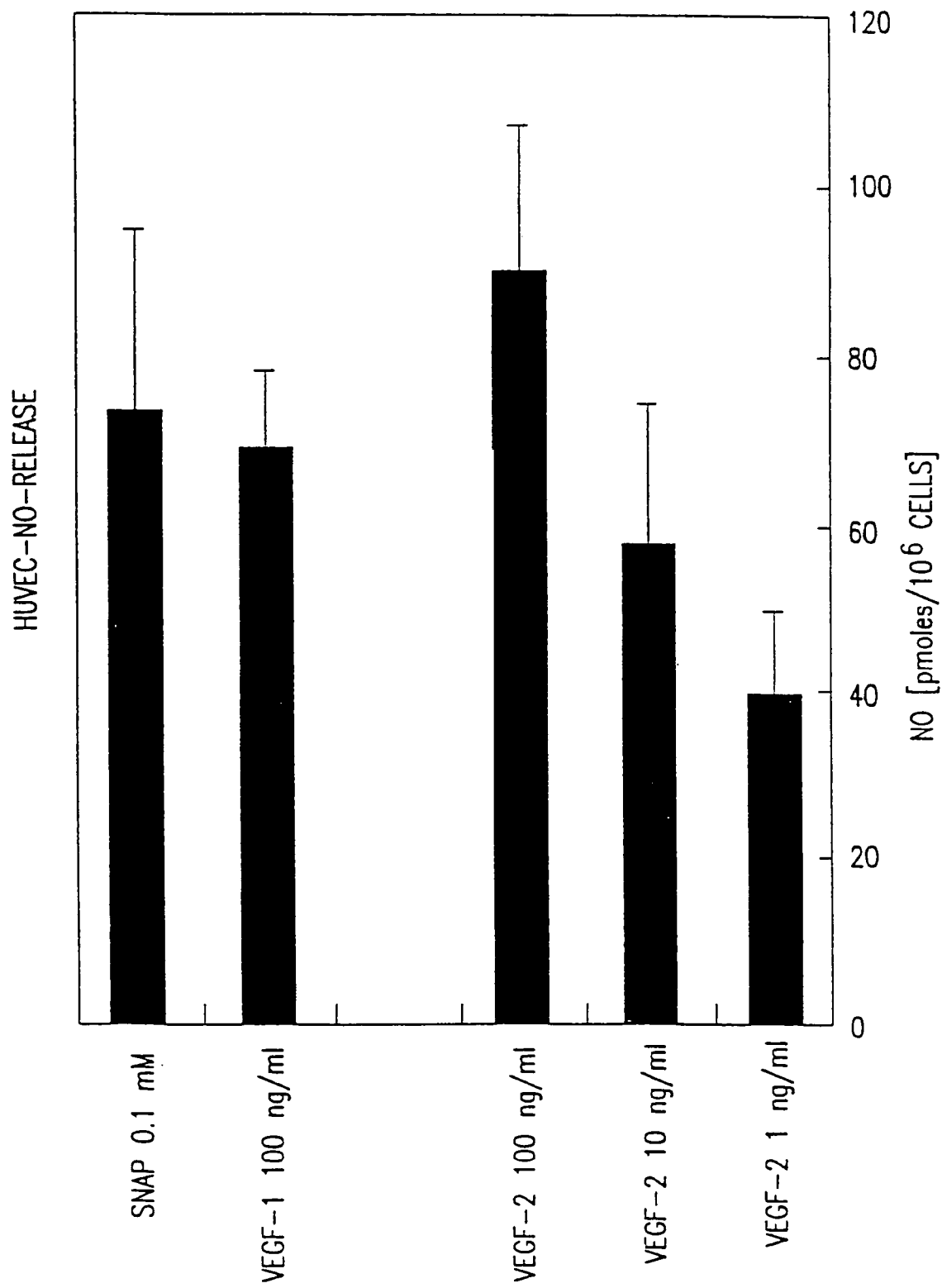
FIG. 22 depicts stimulation of nitric oxide release of HUVEC by VEGF-2 and VEGF-1.

VEGF-2 was capable of stimulating nitric oxide release on HUVEC (FIG. 22) to a higher level than VEGF. This suggested that VEGF2 may modify vascular permeability and vessel dilation.

EXAMPLE 15

Effect of VEGF-2 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

Experimental Design

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 µl/well) for 30 min. at 37° C. CADMEC are seeded onto the coated wells at 7,500 cells/well and cultured overnight in Growth Medium. The Growth Medium is then replaced with 300 µg Cell Applications' Chord Formation Medium containing control buffer or HGS protein (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. β-esteradiol (1 ng/ml) is used as a negative control. The appropriate buffer (without protein) is also utilized as a control.

Results

Figure 23:
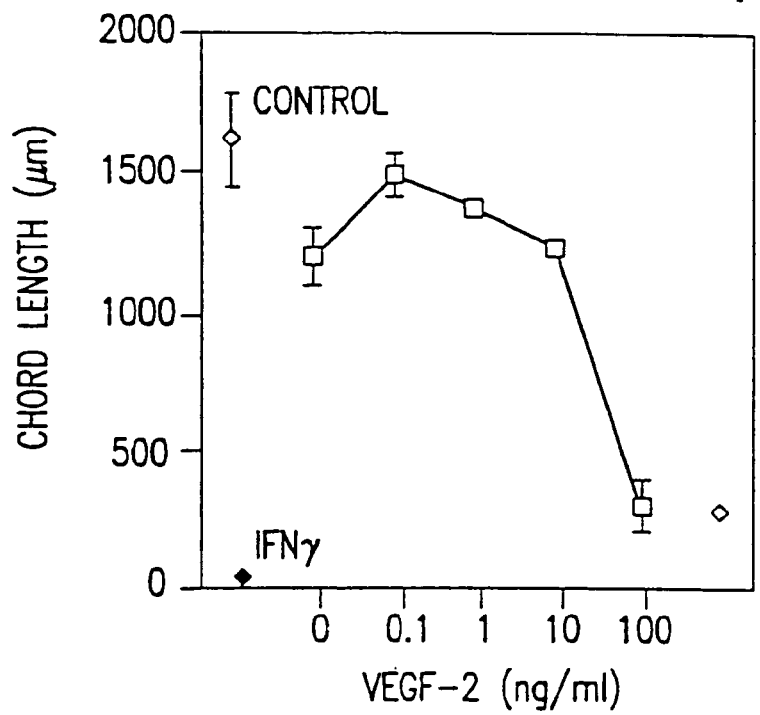
FIG. 23 depicts inhibition of cord formation of microvascular endothelial cells (CADMEC) by VEGF-2.

It has been observed that VEGF2 inhibits cord formation similar to IFNα which also stimulates endothelial cell proliferation (FIG. 23). This inhibitory effect may be a secondary effect of endothelial proliferation which is mutually exclusive with the cord formation process.

EXAMPLE 16

Angiogenic Effect on Chick Chorioallantoic Membrane

Chick chorioallantoic membrane (CAM) is a well-established system to examine angiogenesis. Blood vessel formation on CAM is easily visible and quantifiable. The ability of VEGF2 to stimulate angiogenesis in CAM was examined.

Experimental Design

Embryos

Fertilized eggs of the White Leghorn chick (*Gallus gallus*) and the Japanese quail (*Coturnix coturnix*) were incubated at 37.8° C. and 80% humidity. Differentiated CAM of 16-day-old chick and 13-day-old quail embryos was studied with the following methods.

CAM Assay

On Day 4 of development, a window was made into the egg shell of chick eggs. The embryos were checked for normal development and the eggs sealed with cellotape. They were further incubated until Day 13. Thermanox coverslips (Nunc, Naperville, Ill.) were cut into disks of about 5 mm in diameter. Sterile and salt-free growth factors were dissolved in distilled water and about 3.3 µg/5 µl was pipetted on the disks. After air-drying, the inverted disks were applied on CAM. After 3 days, the specimens were fixed in 3% glutaraldehyde and 2% formaldehyde and rinsed in 0.12 M sodium cacodylate buffer. They were photographed with a stereo microscope [Wild M8] and embedded for semi- and ultrathin sectioning as described above. Controls were performed with carrier disks alone.

Results

Figure 24:
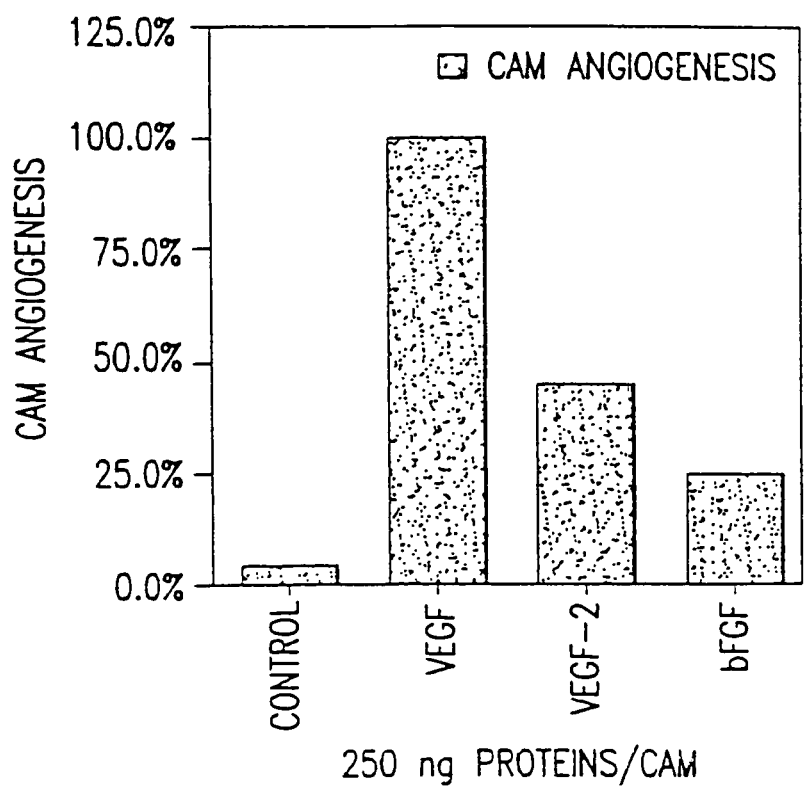
FIG. 24 depicts stimulation of angiogenesis by VEGF, VEGF-2, and bFGF in the CAM assay.
Figure 25A:
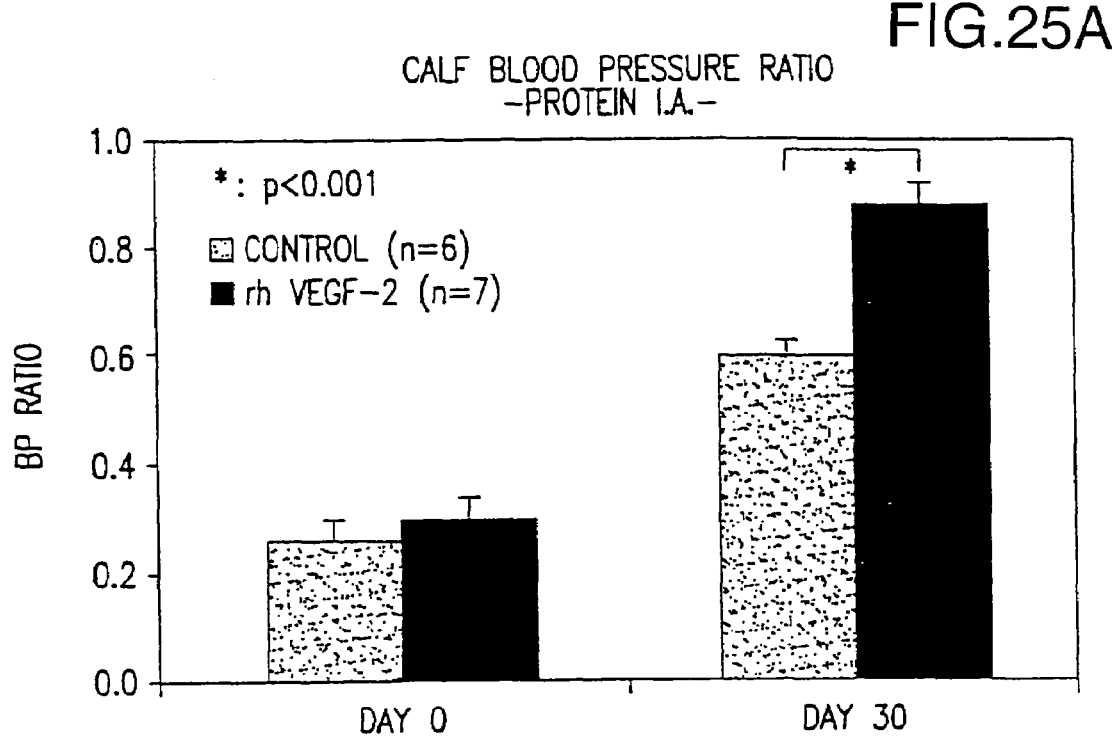
FIGS. 25A-25O depict restoration of certain parameters in the ischemic limb by VEGF2 protein (FIGS. 25A, 25D, 25E, 25J, and 25M) and naked expression plasmid (FIGS. 25B, 25F, 25G, 25K, and 25N): BP ratio (FIGS. 25A-25C); Blood Flow and Flow Reserve FIGS. 25D-25I); Angiographic Score (FIGS. 25J-25L); Capillary density (FIGS. 25M-25O).
Figure 25B:
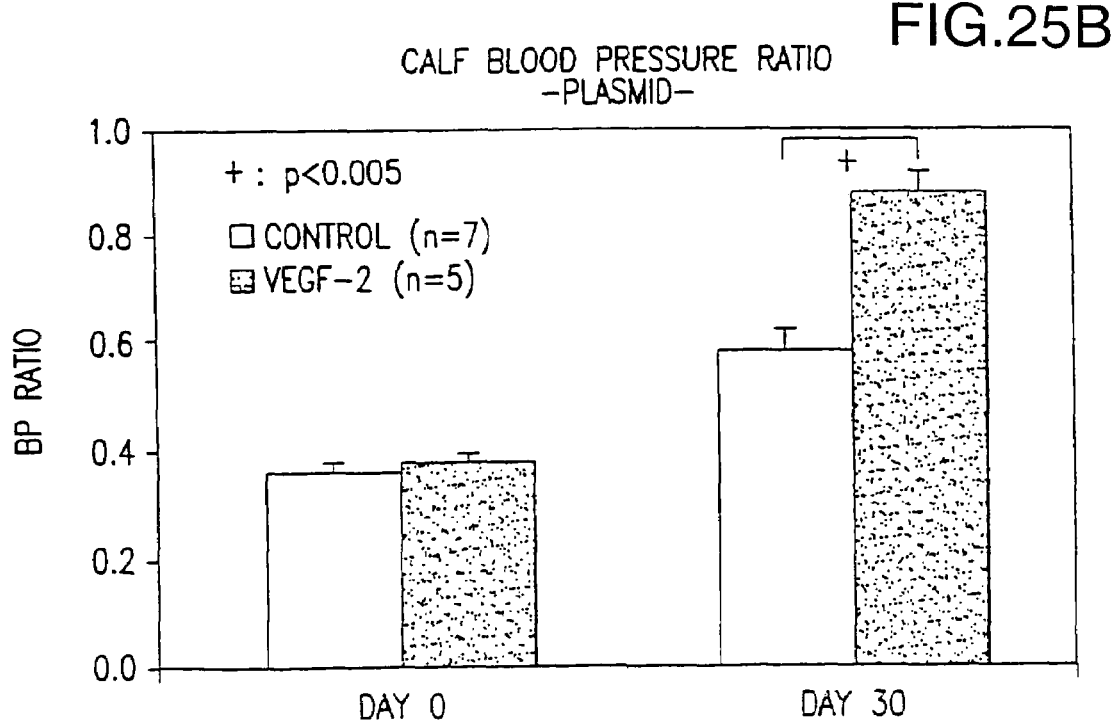
Figure 25C:
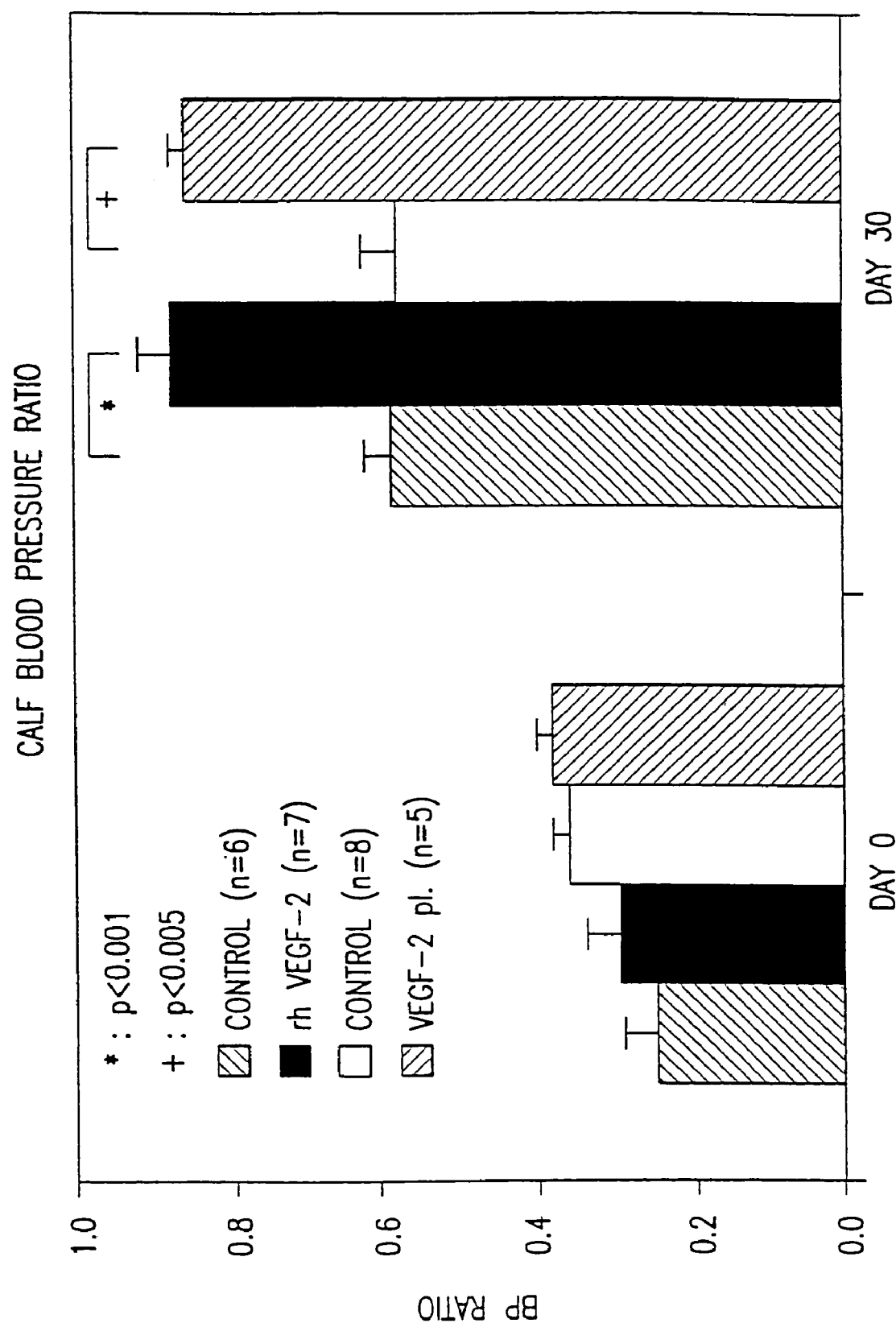
Figure 25D:
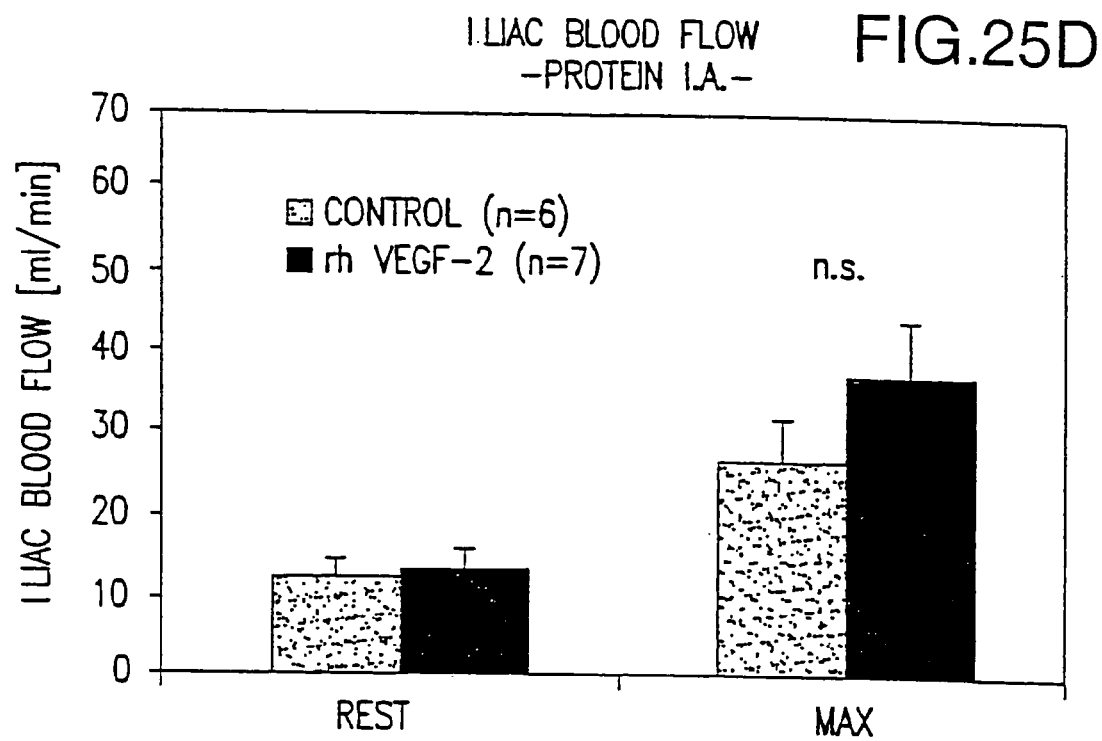
Figure 25E:
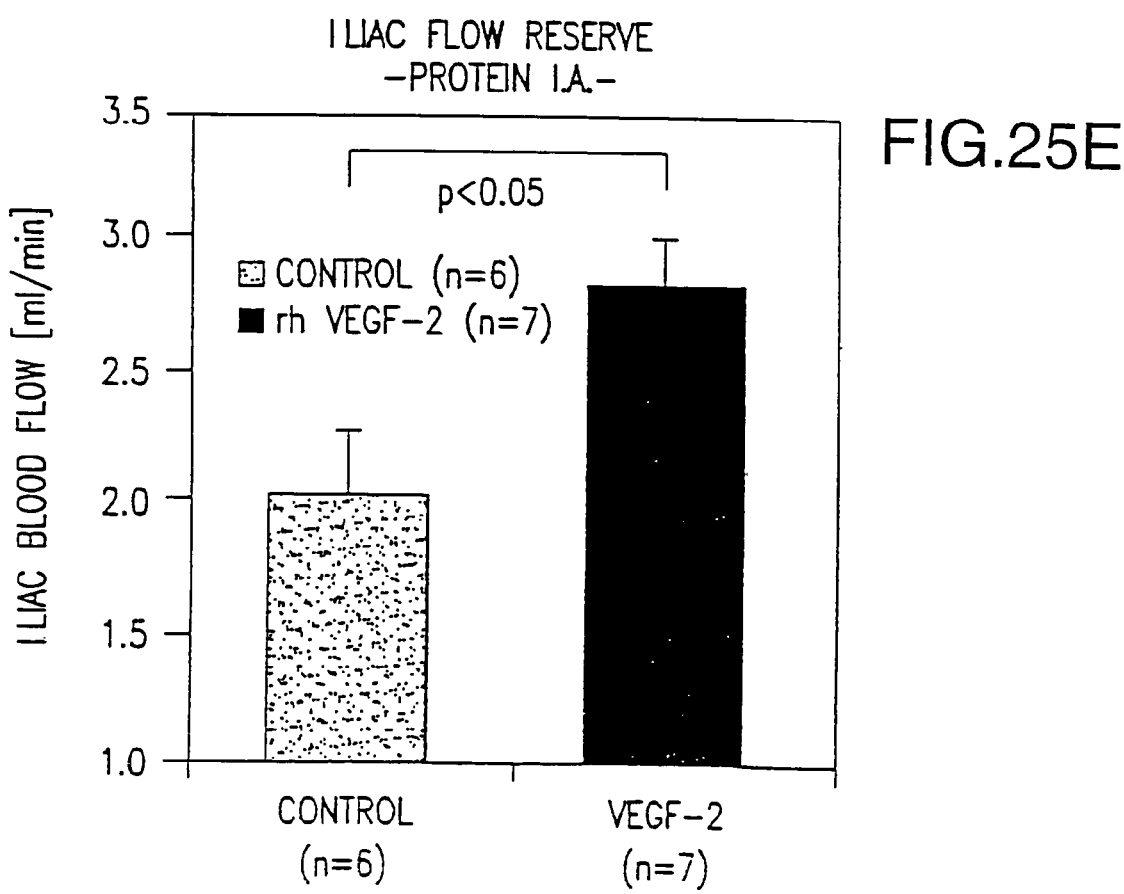
Figure 25F:
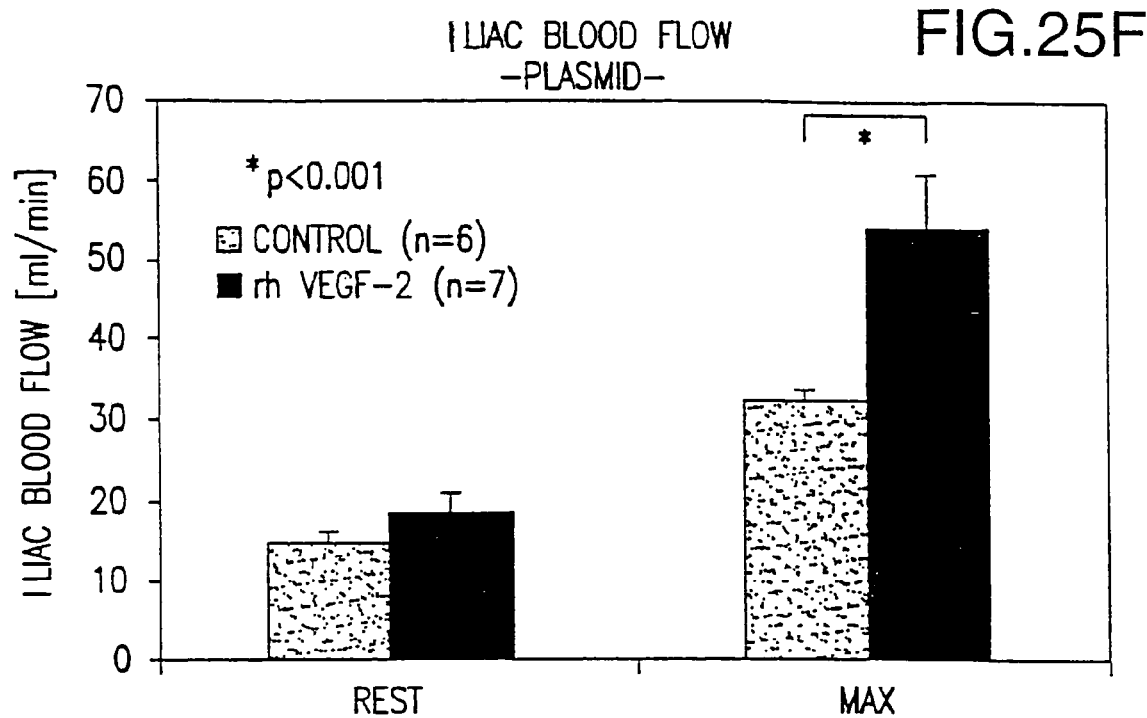
Figure 25G:
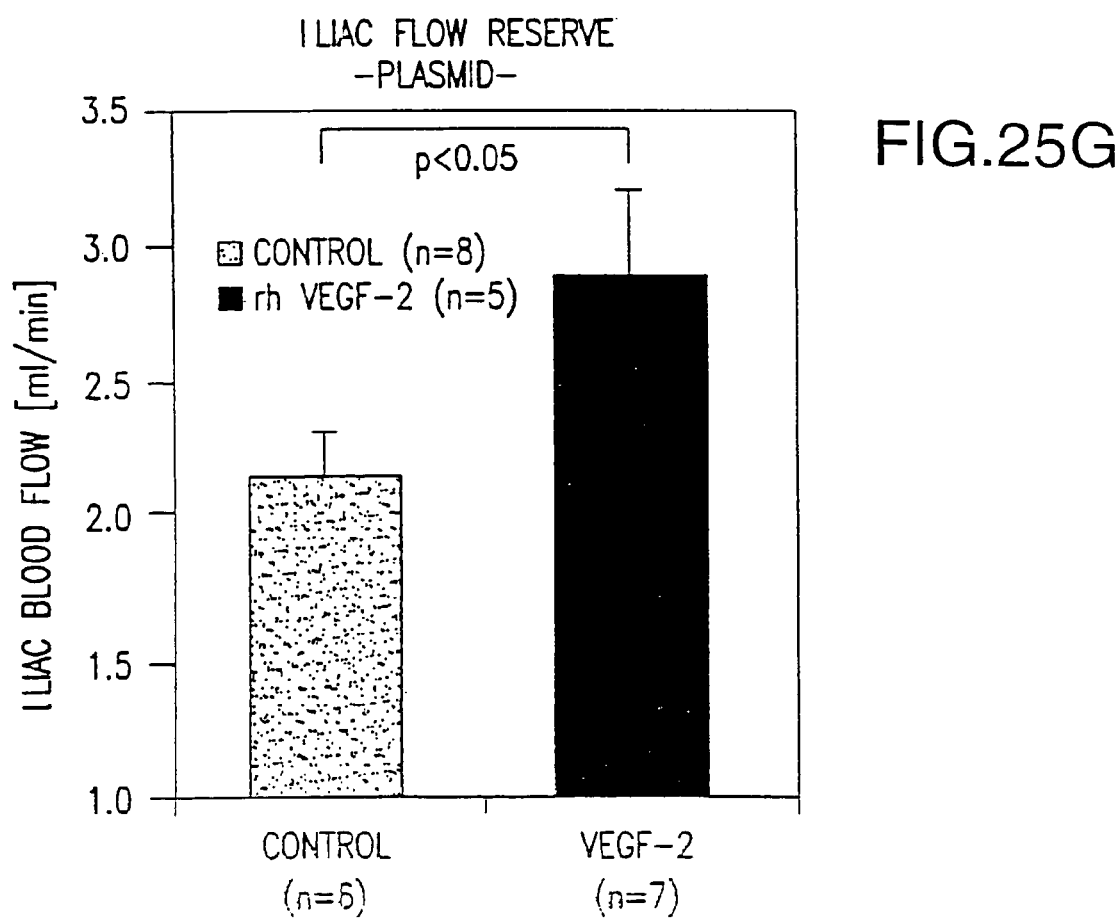
Figure 25H:
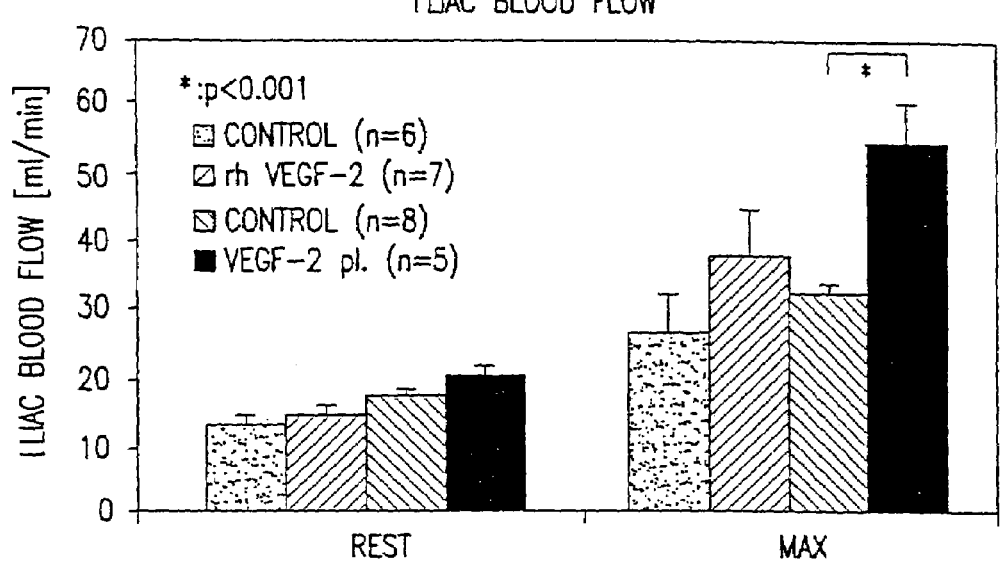
Figure 25I:
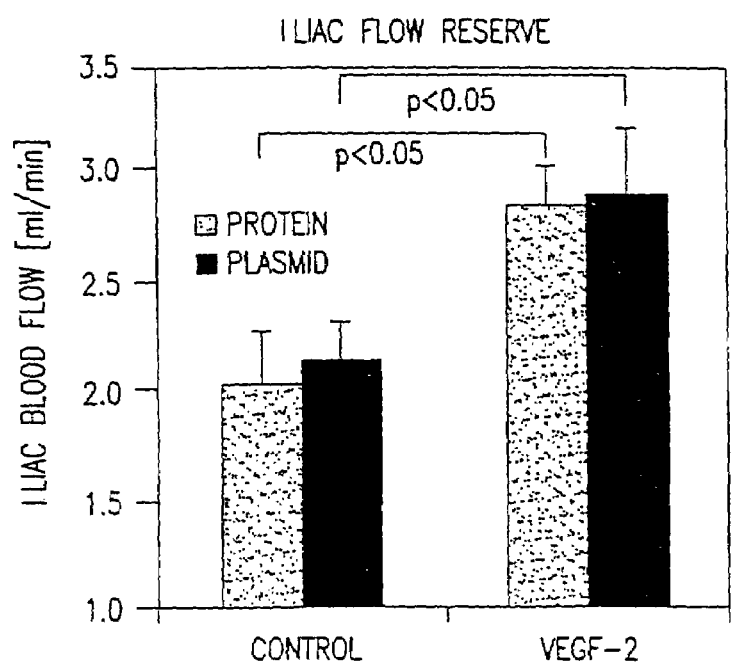
Figure 25J:
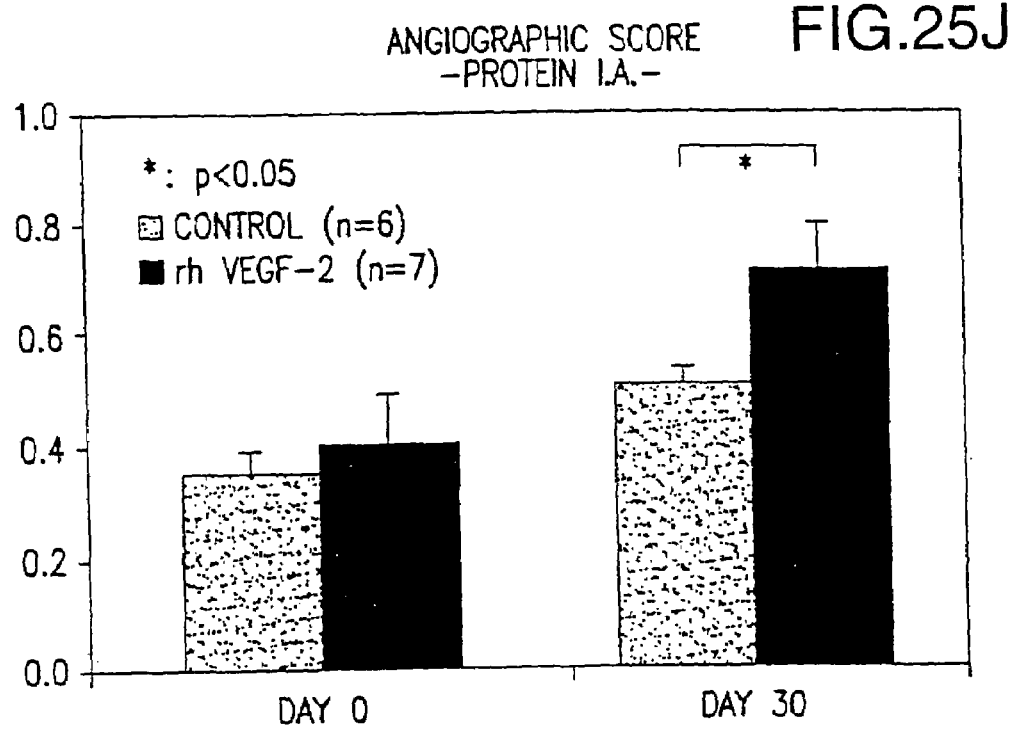
Figure 25K:
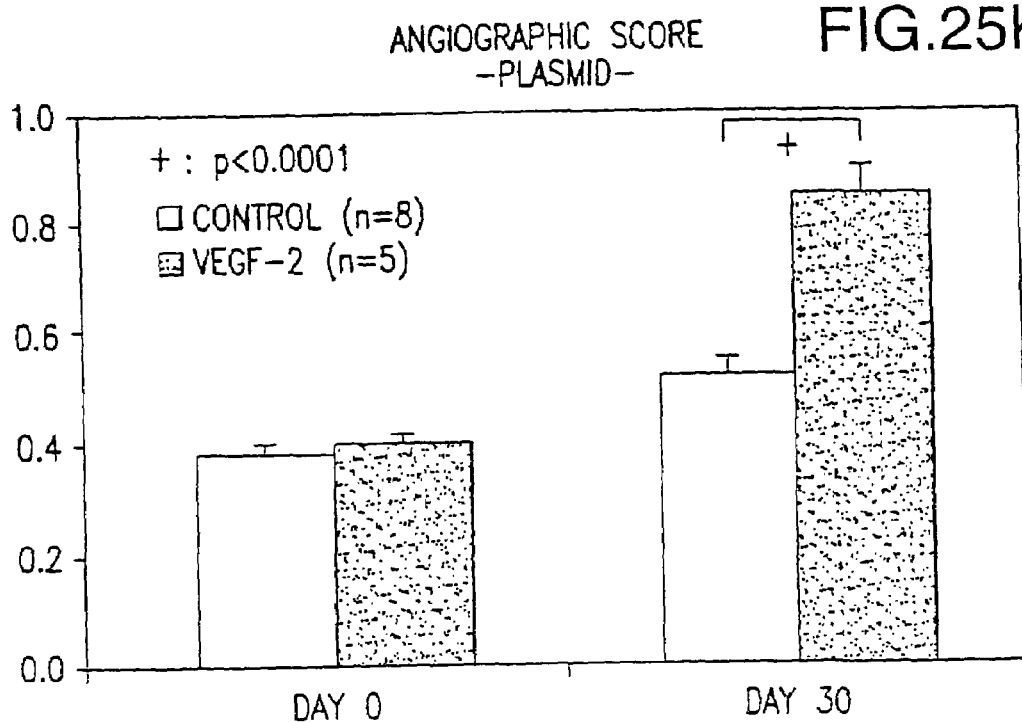
Figure 25L:
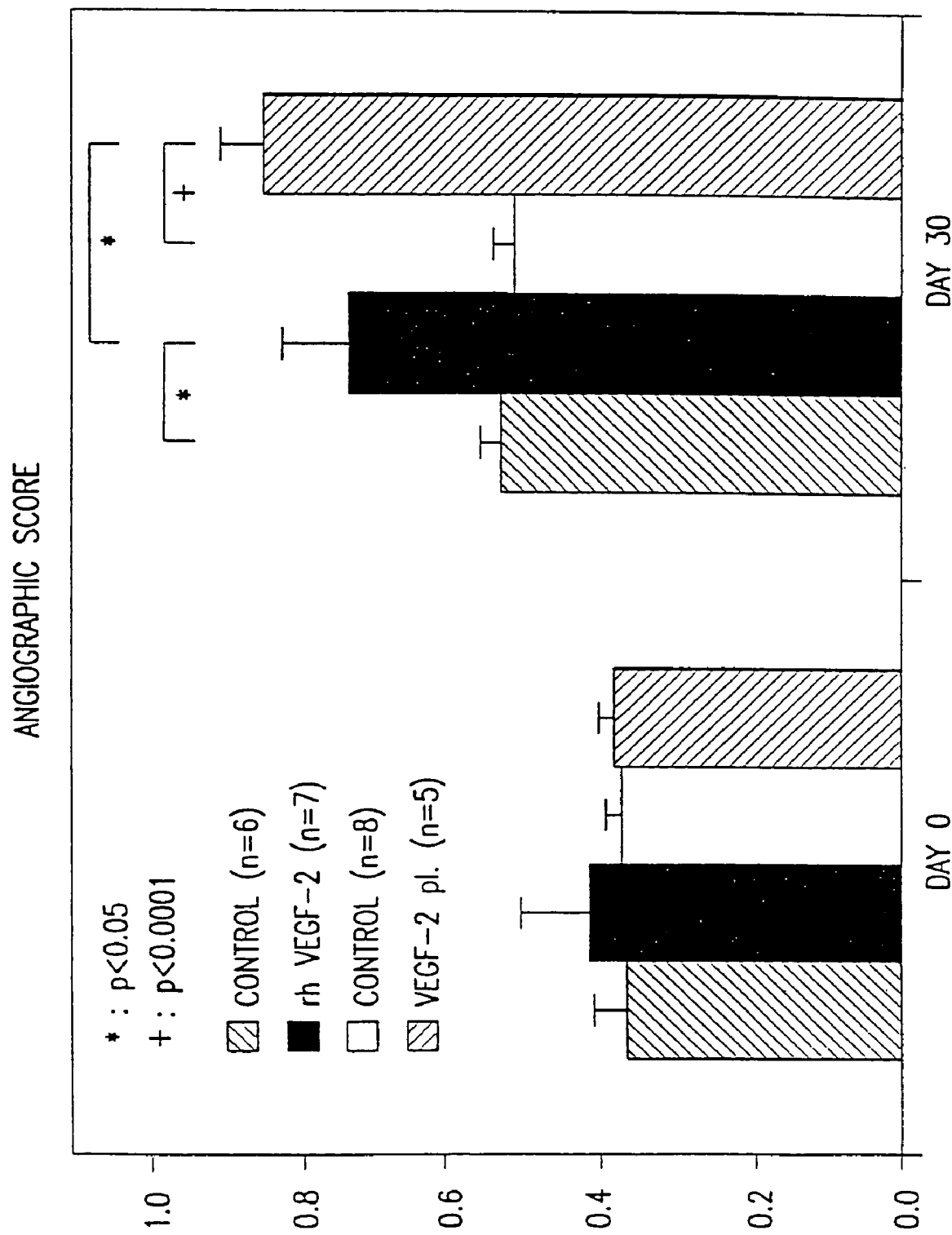
Figure 25M:
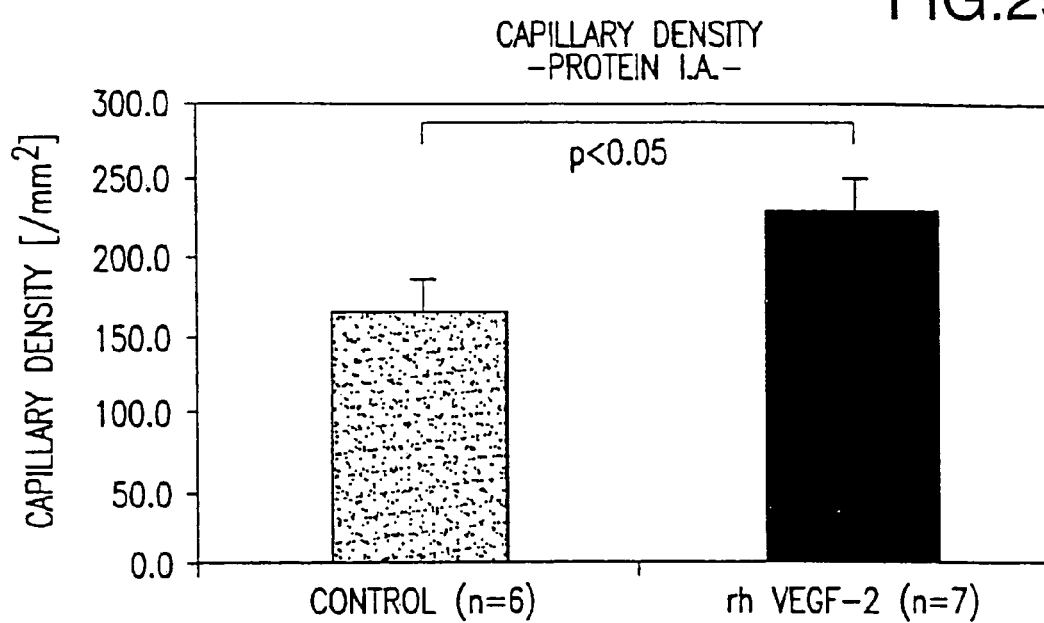
Figure 25N:
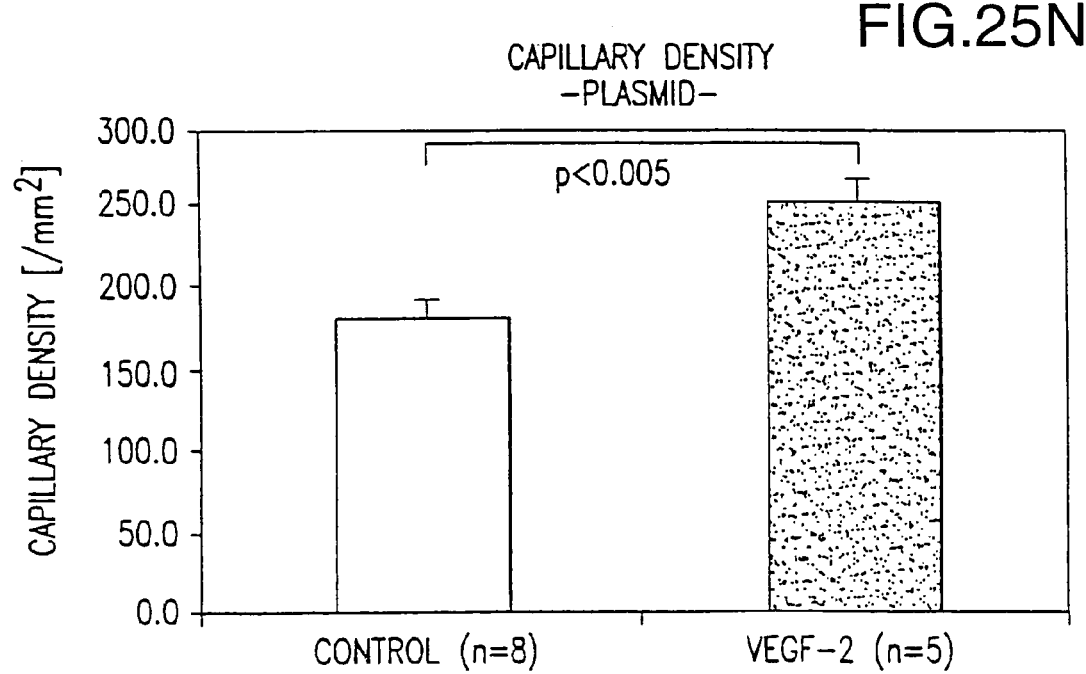
Figure 25O:
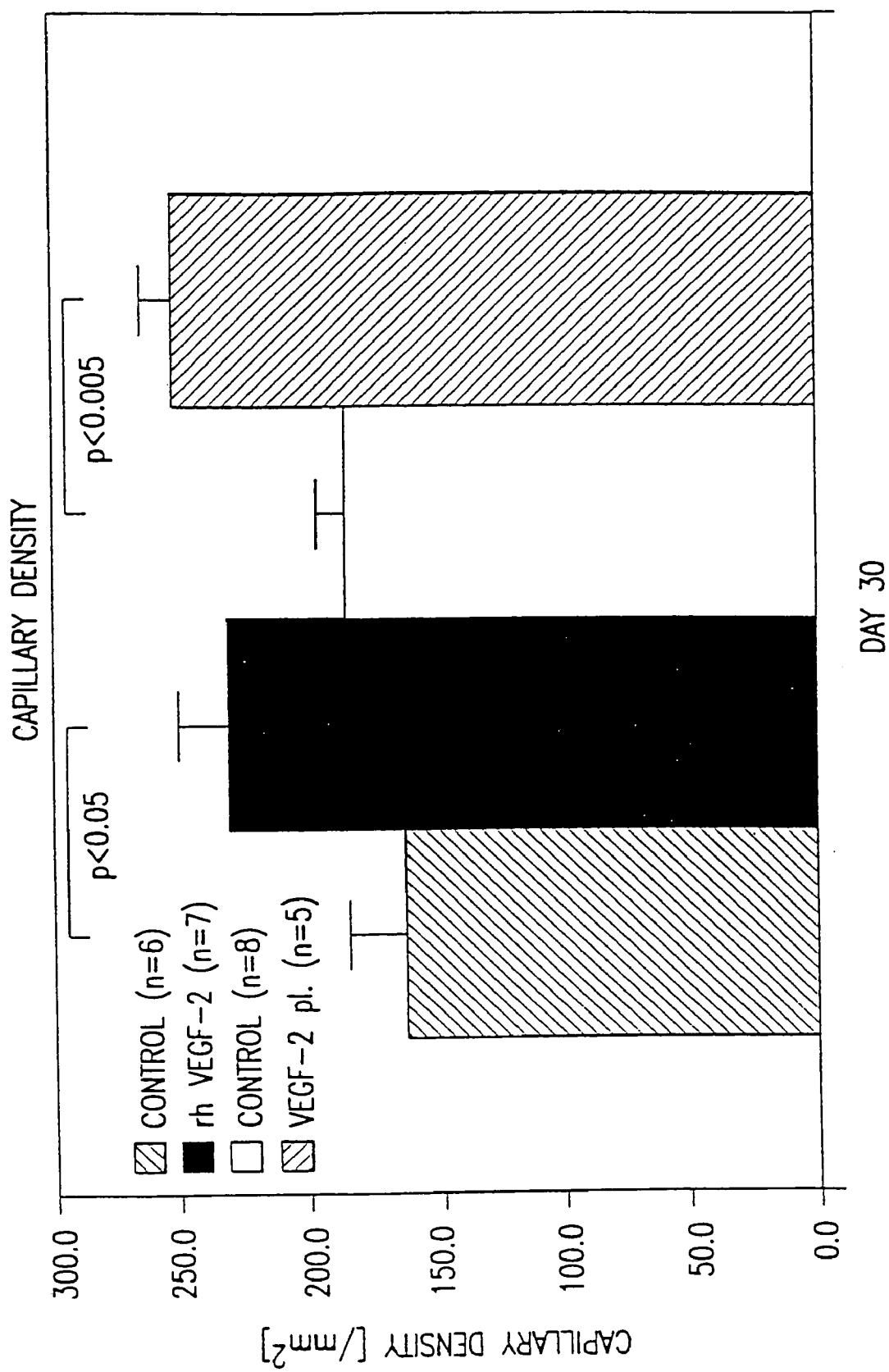

This data demonstrates that VEGF2 can stimulate angiogenesis in the CAM assay nine-fold compared to the untreated control. However, this stimulation is only 45% of the level of VEGF stimulation (FIG. 24).

EXAMPLE 17

Angiogenesis Assay Using a Matrigel Implant in Mouse

Experimental Design

In order to establish an in vivo model for angiogenesis to test protein activities, mice and rats have been implanted subcutaneous with methylcellulose disks containing either 20 mg of BSA (negative control) and 1 mg of bFGF and 0.5 mg of VEFG-1 (positive control).

It appeared as though the BSA disks contained little vascularization, while the positive control disks showed signs of vessel formation. At day 9, one mouse showed a clear response to the bFGF.

Results

Both VEGF proteins appeared to enhance Matrigel cellularity by a factor of approximately 2 by visual estimation.

An additional 30 mice were implanted with disks containing BSA, bFGF, and varying amounts of VEGF-1, VEGF-2-B8, and VEGF-2-C4. Each mouse received two identical disks, rather than one control and one experimental disk.

Samples of all the disks recovered were immunostained with Von Willebrand's factor to detect for the presence of endothelial cells in the disks, and flk-1 and flt-4 to distinguish between vascular and lymphatic endothelial cells. However, definitive histochemical analysis of neovascularization and lymphangiogenesis could not be determined.

EXAMPLE 18

Rescue of Ischemia in Rabbit Lower Limb Model

Experimental Design

To study the in vivo effects of VEGF2 on ischemia, a rabbit hindlimb ischemia model was created by surgical removal of one femoral arteries as described previously (Takeshita, S. et al. Am J. Pathol 147:1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. Am J. Pathol 147:1649-1660 (1995)). An interval of 10 days was allowed for postoperative recovery of rabbits and development of endogenous collateral vessels. At 10 day postoperatively (day 0), after performing a baseline angiogram, the internal iliac artery of the ischemic limb was transfected with 500 µg naked VEGF2 expression plasmid by arterial gene transfer technology using a hydrogel-coated balloon catheter as described (Riessen, R. et al. Hum Gene Ther. 4:749-758 (1993); Leclerc, G. et al. J. Clin. Invest. 90: 936-944 (1992)). When VEGF2 was used in the treatment, a single bolus of 500 µg VEGF2 protein or control was delivered into the internal iliac artery of the ischemic limb over a period of 1 min. through an infusion catheter. On day 30, various parameters were measured in these rabbits.

Results

Both VEGF2 protein (FIG. 25, top panels) and naked expression plasmid (FIG. 25, middle panels) were able to restore the following parameters in the ischemic limb. Restoration of blood flow, angiographic score seem to be slightly more by administration of 500 µg plasmid compared with by 500 µg protein (FIG. 25, bottom panels) The extent of the restoration is comparable with that by VEGF in separate experiments (data not shown). A vessel dilator was not able to achieve the same effect, suggesting that the blood flow restoration is not simply due to a vascular dilation effect.

a. BP ratio (FIGS. 25A-C)
  The blood pressure ratio of systolic pressure of the ischemic limb to that of normal limb.
b. Blood Flow and Flow Reserve (FIGS. 25D-I)
  Resting FL: the blood flow during un-dilated condition
  Max FL: the blood flow during fully dilated condition (also an indirect measure of the blood vessel amount)
  Flow Reserve is reflected by the ratio of max FL: resting FL.
c. Angiographic Score (FIGS. 25J-L)
  This is measured by the angiogram of collateral vessels. A score was determined by the percentage of circles in an overlaying grid that with crossing opacified arteries divided by the total number m the rabbit thigh.
d. Capillary density (FIGS. 25M-O)
  The number of collateral capillaries determined in light microscopic sections taken from hindlimbs.

As discussed, VEGF2 is processed to an N-terminal and a C-terminal fragment which are co-purified. The N-terminal fragment contains the intact putative functional domain and may be responsible for the biologic activity.

EXAMPLE 19

Effect of VEGF2 on Vasodilation

Figure 26A:
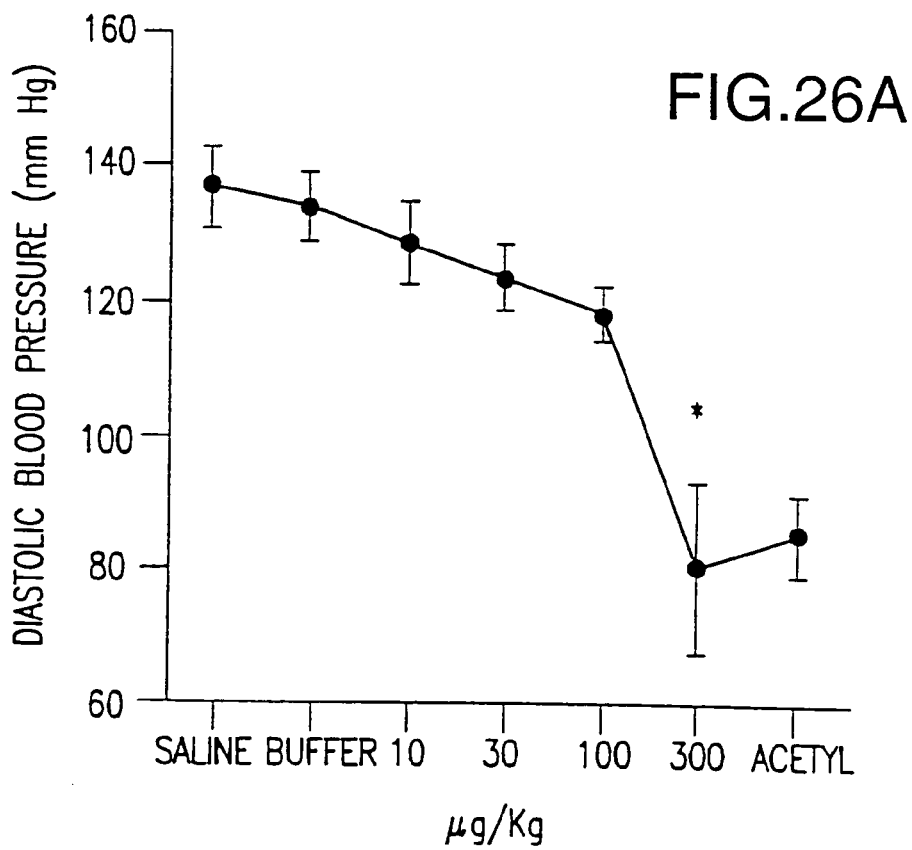
Figure 26B:
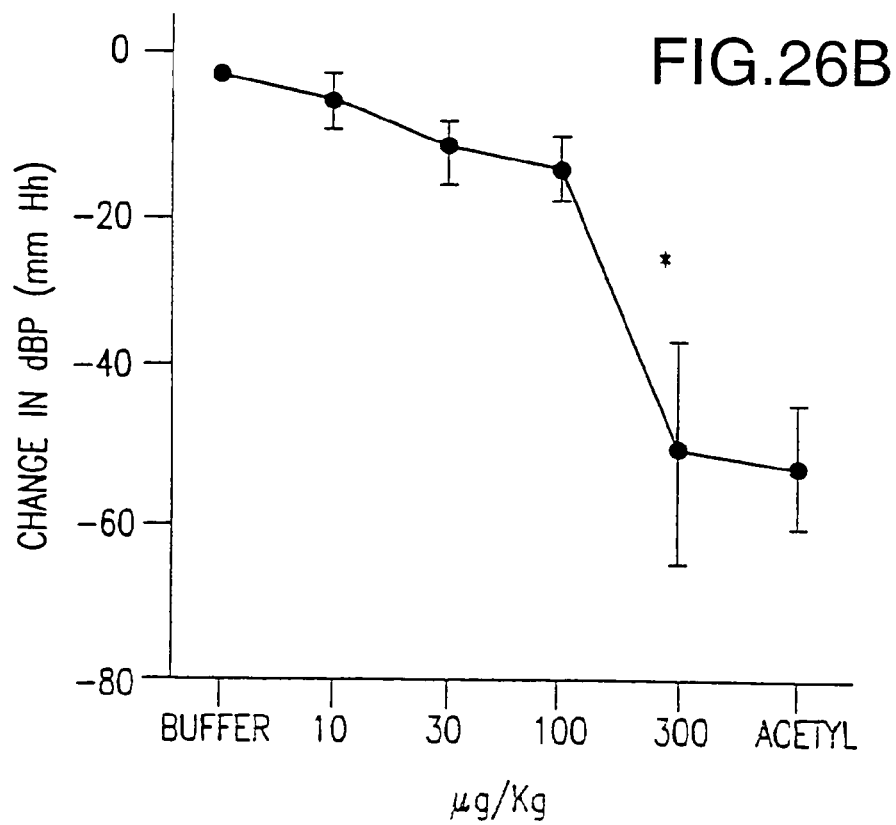
Figure 26E:
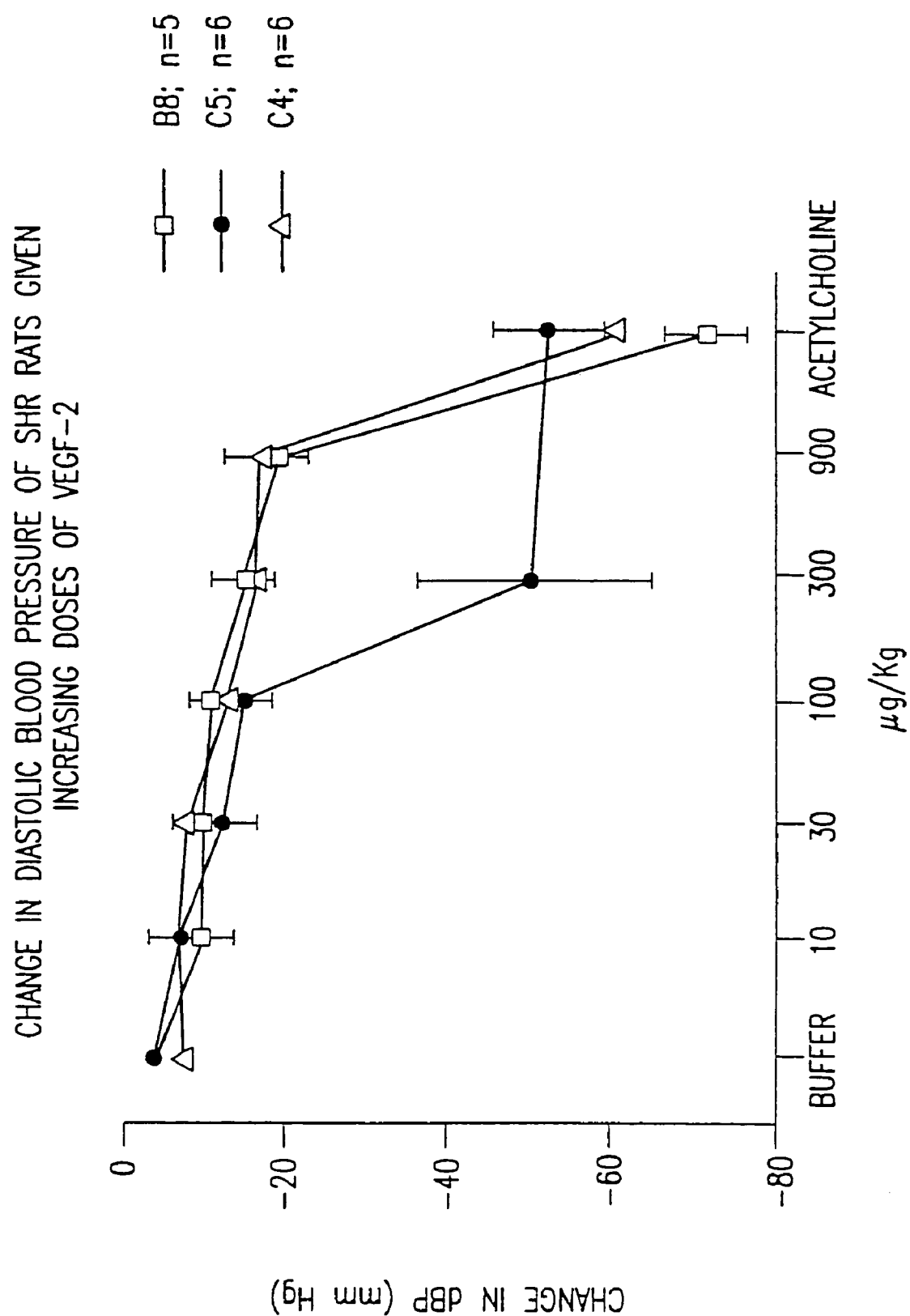
Figure 26F:
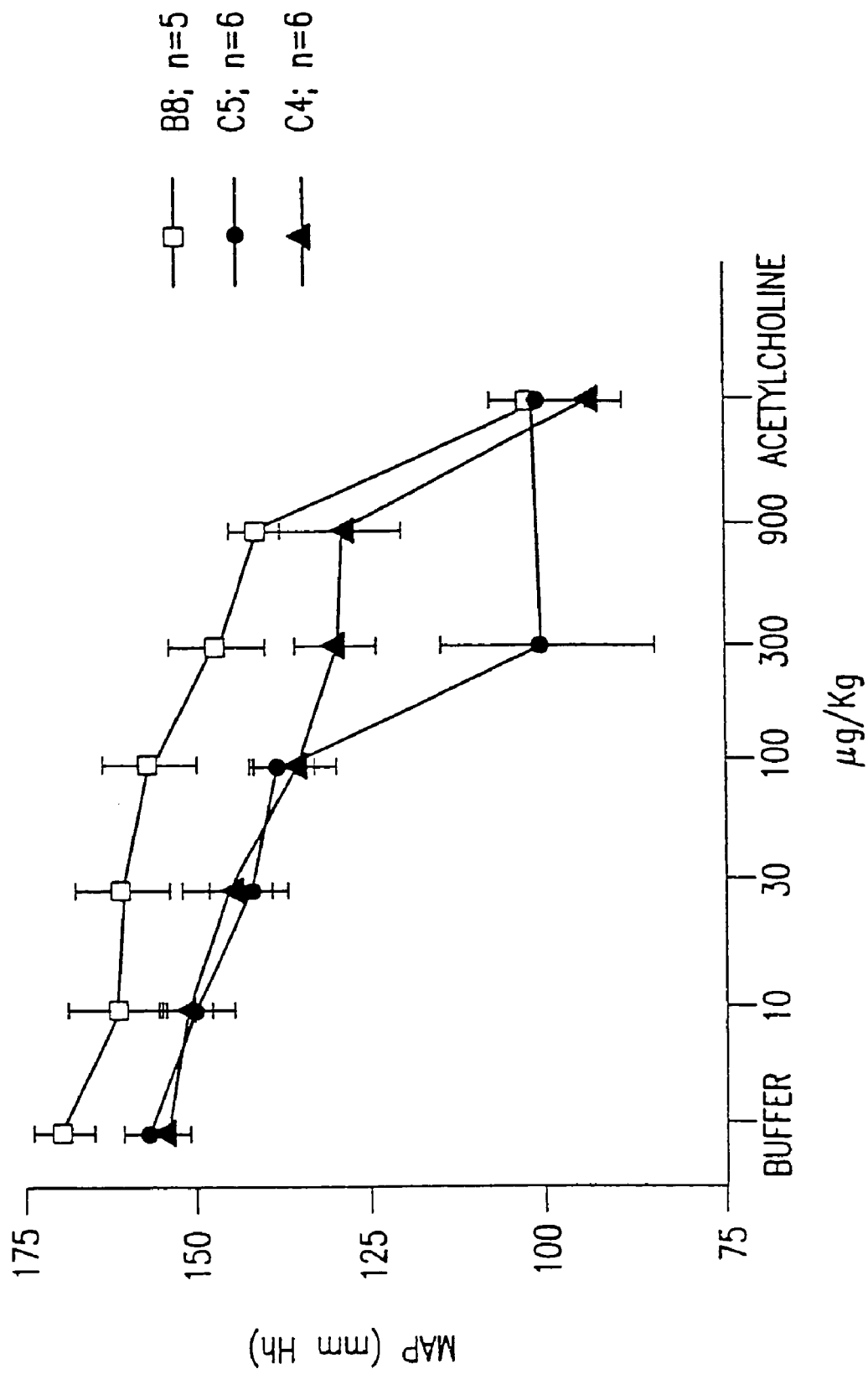
Figure 26G:
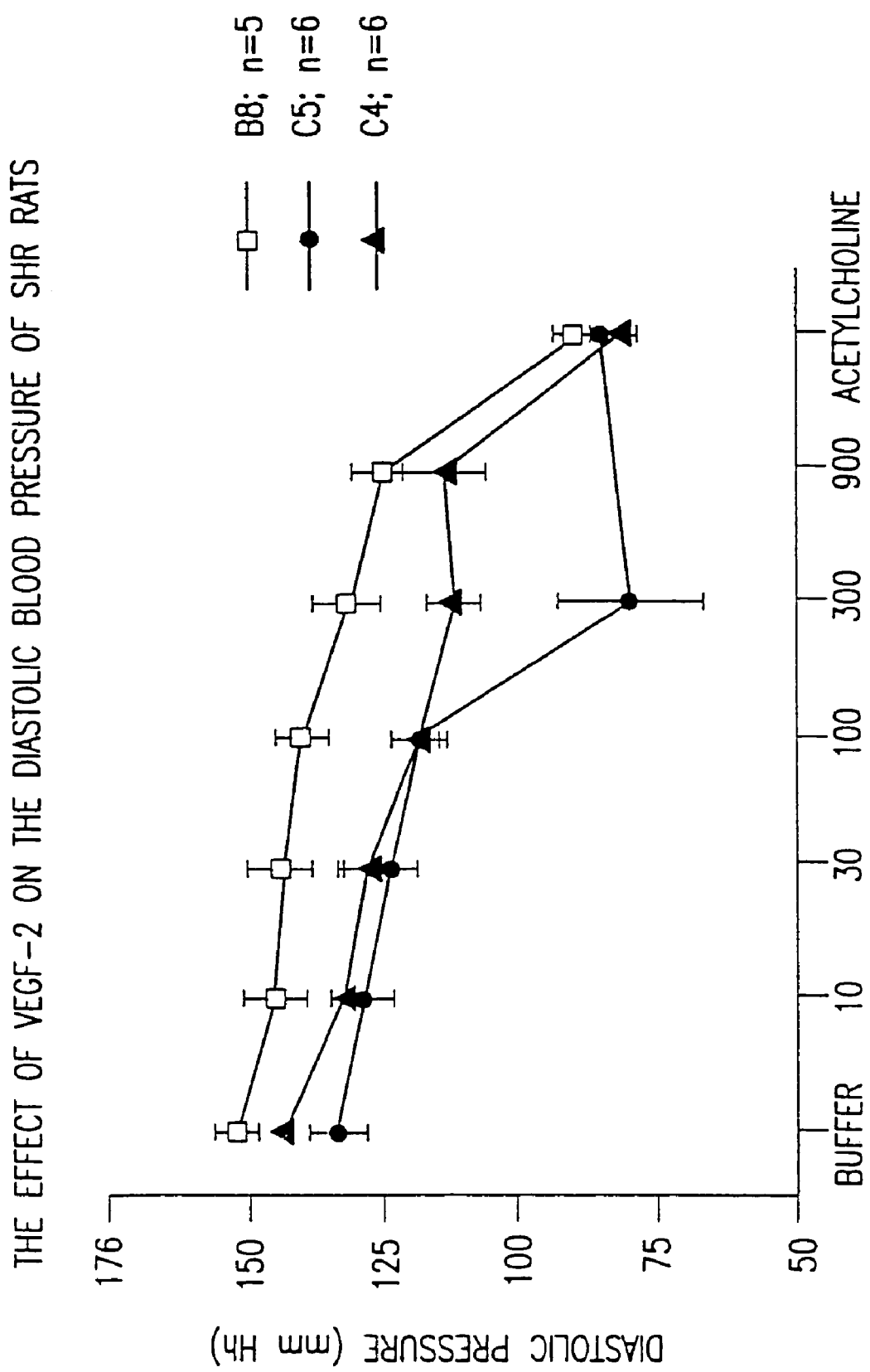
Figure 27:
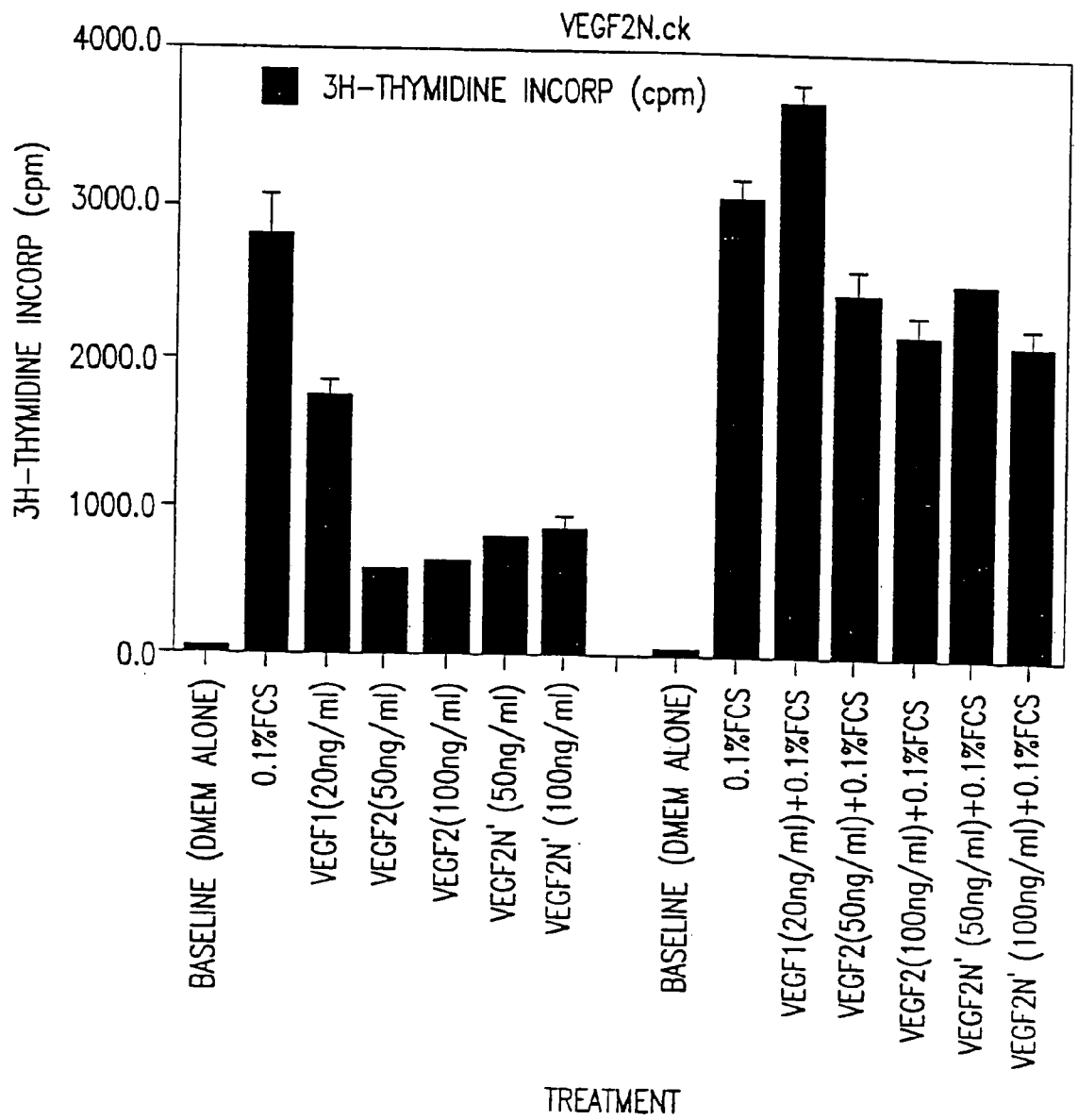
FIG. 27 depicts inhibition of VEGF-2N' and VEGF-2-induced proliferation.

As described above, VEGF2 can stimulate NO release, a mediator of vascular endothelium dilation. Since dilation of vascular endothelium is important in reducing blood pressure, the ability of VEGF2 to affect the blood pressure in spontaneously hypertensive rats (SHR) was examined. VEGF2 caused a dose-dependent decrease in diastolic blood pressure (FIGS. 26a and b). There was a steady decline in diastolic blood pressure with increasing doses of VEGF2 which attained statistical significance when a dose of 300 μg/kg was administered. The changes observed at this dose were not different than those seen with acetylcholine (0.5 μg/kg). Decreased mean arterial pressure (MAP) was observed as well (FIGS. 26c and d). VEGF2 (300 μg/kg) and acetylcholine reduced the MAP of these SHR animals to normal levels.

Additionally, increasing doses (0, 10, 30, 100, 300, and 900 μg/kg) of the B8, C5, and C4 preps of VEGF-2 were administered to 13-14 week old spontaneously hypertensive rats (SHR). Data are expressed as the mean +/−SEM. Statistical analysis was performed with a paired t-test and statistical significance was defined as $p<0.05$ vs. the response to buffer alone.

Studies with VEGF-2 (C5 prep) revealed that although it significantly decreased the blood pressure, the magnitude of the response was not as great as that seen with VEGF-2 (B8 prep) even when used at a dose of 900 μg/kg.

Studies with VEGF-2 (C4 preparation) revealed that this CHO expressed protein preparation yielded similar results to that seen with C5 (i.e. statistically significant but of far less magnitude than seen with the B8 preparation) (see FIGS. 26A-D).

As a control and since the C4 and C5 batches of VEGF-2 yielded minor, but statistically significant, changes in blood pressure, experiments were performed experiments with another CHO-expressed protein, M-CIF. Administration of M-CIF at doses ranging from 10-900 μg/kg produced no significant changes in diastolic blood pressure. A minor statistically significant reduction in mean arterial blood pressure was observed at doses of 100 and 900 μg/kg but no dose response was noted. These results suggest that the reductions in blood pressure observed with the C4 and C5 batches of VEGF-2 were specific, i.e. VEGF-2 related.

EXAMPLE 20

Rat Ischemic Skin Flap Model

Experimental Design

The evaluation parameters include skin blood flow, skin temperature, and factor VIII immunohistochemistry or endothelial alkaline phosphatase reaction. VEGF-2 expression, during the skin ischemia, is studied using in situ hybridization.

The study in this model is divided into three parts as follows:
  a) Ischemic skin
  b) Ischemic skin wounds
  c) Normal wounds The experimental protocol includes:
  a) Raising a 3×4 cm, single pedicle full-thickness random skin flap (myocutaneous flap over the lower back of the animal).
  b) An excisional wounding (4-6 mm in diameter) in the ischemic skin (skin-flap).
  c) Topical treatment with VEGF-2 of the excisional wounds (day 0, 1, 2, 3, 4 post-wounding) at the following various dosage ranges 1 μg to 100 μg.
  d) Harvesting the wound tissues at day 3, 5, 7, 10, 14 and 21 post-wounding for histological, immunohistochemical, and in situ studies

EXAMPLE 22

Peripheral Arterial Disease Model

Angiogenic therapy using VEGF-2 has been developed as a novel therapeutic strategy to obtain restoration of blood flow around the ischemia in case of peripheral arterial diseases.

Experimental Design

The experimental protocol includes:
a) One side of the femoral artery is ligated to create ischemic muscle of the hindlimb, the other side of hindlimb serves as a control.
b) VEGF-2 protein, in a dosage range of 20 μg-500 μg, is delivered intravenously and/or intramuscularly 3 times (perhaps more) per week for 2-3 weeks.
c) The ischemic muscle tissue is collected after ligation of the femoral artery at 1, 2, and 3 weeks for the analysis of VEGF-2 expression and histology. Biopsy is also performed on the other side of normal muscle of the contralateral hindlimb.

EXAMPLE 23

Ischemic Myocardial Disease Model

VEGF-2 is evaluated as a potent mitogen capable of stimulating the development of collateral vessels, and restructuring new vessels after coronary artery occlusion. Alteration of VEGF-2 expression is investigated in situ.

Experimental Design

The experimental protocol includes:
a) The heart is exposed through a left-side thoracotomy in the rat. Immediately, the left coronary artery is occluded with a thin suture (6-0) and the thorax is closed.
b) VEGF-2 protein, in a dosage range of 20 µg-500 µg, is delivered intravenously and/or intramuscularly 3 times (perhaps more) per week for 24 weeks.
c) Thirty days after the surgery, the heart is removed and cross-sectioned for morphometric and in situ analyzes.

EXAMPLE 24

Rat Corneal Wound Healing Model

This animal model shows the effect of VEGF-2 on neovascularization. Experimental Design The experimental protocol includes:
a) Making a 1-1.5 mm long incision from the center of cornea into the stromal layer.
b) Inserting a spatula below the lip of the incision facing the outer corner of the eye.
c) Making a pocket (its base is 1-1.5 mm form the edge of the eye).
d) Positioning a pellet, containing 50 µg-500 µg VEGF-2, within the pocket.
e) VEGF-2 treatment can also be applied topically to the corneal wounds in a dosage range of 20 µg-500 µg (daily treatment for five days).

EXAMPLE 25

Diabetic Mouse and Glucocorticoid-impaired Wound Healing Models

Experimental Design

The experimental protocol includes:

A. Diabetic db+/db+Mouse Model.

To demonstrate that VEGF-2 accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., J. Surg. Res. 52:389 (1992); Greenhalgh, D. G. et a., Am. J. Pathol. 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. Proc. Natl. Acad. Sci. USA 77:283-293 (1982)). Animals show ployphagia, polydipsia and polyuria. Mutant diabetic mice (db+/db+) have elevated blood glucose, increased or normal insulin levels, and suppressed cell-mediated immunity (Mandel et al., J. Immunol. 120:1375 (1978); Debray-Sachs, M. et al., Clin. Exp. Immunol. 51(1):1-7 (1983); Leiter et. al., Am. J of Pathol. 114:46-55 (1985)). Peripheral neuropathy, myocardial complications, and microvascular lesions, basement membrane thickening and glomerular filtration abnormalities have been described in these animals (Norido, F. et al., Exp. Neurol. 83(2):221-232 (1994); Robertson et al., Diabetes 29(1):60-67 (1980); Giacomelli et al., Lab Invest. 40(4):460-473 (1979); Coleman, D. L., Diabetes 31 (Suppl):1-6 (1982)). These homozygous diabetic mice develop hyperglycemia that is resistant to insulin analogous to human type II diabetes (Mandel et al., J. Immunol. 120:1375-1377 (1978)).

The characteristics observed in these animals suggests that healing in this model may be similar to the healing observed in human diabetes (Greenhalgh, et al., Am. J. of Pathol. 136:1235-1246 (1990)).

Animals

Genetically diabetic female C57BL/KsJ (db+/db+) mice and their non-diabetic (db+/+m) heterozygous littermates were used in this study (Jackson Laboratories). The animals were purchased at 6 weeks of age and were 8 weeks old at the beginning of the study. Animals were individually housed and received food and water ad libitum. All manipulations were performed using aseptic techniques. The experiments were conducted according to the rules and guidelines of Human Genome Sciences, Inc. Institutional Animal Care and Use Committee and the Guidelines for the Care and Use of Laboratory Animals.

Surgical Wounding

Wounding protocol is performed according to previously reported methods (Tsuboi, R and Rifkin, D. B., J. Exp. Med. 172:245-251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

VEGF-2 is administered using at a range different doses of VEGF-2, from 4 µg to 500 µg per wound per day for 8 days in vehicle. Vehicle control groups received 50 µL of vehicle solution.

Animals are euthanized on day 8 with an intraperitoneal injection of sodium pentobarbital (300 mg/kg). The wounds an surrounding skin are then harvested for histology and immunohistochemistry. Tissue specimens are placed in 10% neutral buffered formalin in tissue cassettes between biopsy sponges for further processing.

Experimental Design

Three groups of 10 animals each (5 diabetic and 5 non-diabetic controls) were evaluated: 1) Vehicle placebo control, 2) VEGF-2.

Measurement of Wound Area and Closure

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 was 64

$mm^2$, the corresponding size of the dermal punch. Calculations were made using the following formula:

[Open area on day 8]−[Open area on day 1]/[Open area on day 1]

Histology

Specimens are fixed in 10% buffered formalin and paraffin embedded blocks are sectioned perpendicular to the wound surface (5 µm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with KGF-2. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)). A calibrated lens micrometer is used by a blinded observer.

Immunohistochemistry

Re-epithelialization

Tissue sections are stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Cell Proliferation Marker

Proliferating cell nuclear antigen/cyclin (PCNA) in skin specimens is demonstrated by using anti-PCNA antibody (1:50) with a ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0-8, the lower side of the scale reflecting slight proliferation to the higher side reflecting intense proliferation.

Statistical Analysis

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In Anti-Inflammatory Steroid Action: Basic and Clinical Aspects. 280-302 (1989); Wahl, S. M. et al., J. Immunol. 115: 476-481 (1975); Werb, Z. et al., J. Exp. Med. 147:1684-1694 (1978)). Glucocorticoids retard wound healing by inhibiting angiogenesis, decreasing vascular permeability (Ebert, R. H., et al., An. Intern. Med 37:701-705 (1952)), fibroblast proliferation, and collagen synthesis (Beck, L. S. et al., Growth Factors. 5: 295-304 (1991); Haynes, B. F., et al., J. Clin. Invest. 61: 703-797 (1978)) and producing a transient reduction of circulating monocytes (Haynes, B. F., et al., J. Clin. Invest. 61: 703-797 (1978); Wahl, S. M. Glucocorticoids and wound healing. In Antiinflammatory Steroid Action: Basic and Clinical Aspects. Academic Press. New York. pp. 280-302 (1989)). The systemic administration of steroids to impaired wound healing is a well establish phenomenon in rats (Beck, L. S. et al., Growth Factors. 5: 295-304 (1991); Haynes, B. F., et al., J. Clin. Invest. 61: 703-797 (1978); Wahl, S. M. Glucocorticoids and wound healing. In Antiinflammatory Steroid Action: Basic and Clinical Aspects. Academic Press. New York. pp. 280-302 (1989); Pierce, G. F., et al., Proc. Natl. Acad Sci. USA. 86: 2229-2233 (1989)).

To demonstrate that VEGF-2 can accelerate the healing process, the effects of multiple topical applications of VEGF-2 on full thickness excisional skin wounds in rats in which healing has been impaired by the systemic administration of methylprednisolone is assessed.

Animals

Young adult male Sprague Dawley rats weighing 250-300 g (Charles River Laboratories) are used in this example. The animals are purchased at 8 weeks of age and were 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

Surgical Wounding

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1-5 and on day 8 for Figure. Wounds are measured horizontally and vertically using a calibrated Jameson caliper. Wounds are considered healed if granulation tissue was no longer visible and the wound is covered by a continuous epithelium.

VEGF-2 is administered using at a range different doses of VEGF-2, from 4 µg to 500 µg per wound per day for 8 days in vehicle. Vehicle control groups received 50 µL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Experimental Design

Four groups of 10 animals each (5 with methylprednisolone and 5 without glucocorticoid) were evaluated: 1) Untreated group 2) Vehicle placebo control 3) VEGF-2 treated groups.

Measurement of Wound Area and Closure

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 was 64 mm.sup.2, the corresponding size of the dermal punch. Calculations were made using the following formula:

[Open area on day 8]−[Open area on day 1]/[Open area on day 1]

Histology

Specimens are fixed in 10% buffered formalin and paraffin embedded blocks are sectioned perpendicular to the wound surface (5 μm) and cut using an Olympus microtome. Routine hematoxylin-eosin (H&E) staining was performed on cross-sections of bisected wounds. Histologic examination of the wounds allows assessment of whether the healing process and the morphologic appearance of the repaired skin was improved by treatment with VEGF-2. A calibrated lens micrometer was used by a blinded observer to determine the distance of the wound gap.

Statistical Analysis

Experimental data are analyzed using an unpaired t test. A p value of <0.05 is considered significant.

EXAMPLE 26

Specific Peptide Fragments to Generate VEGF-2 Monoclonal Antibodies

Four specific peptides (designated SP-40, SP-41, SP-42 and SP-43) have been generated. These will be used to generate monoclonal antibodies to analyze VEGF-2 processing. The peptides are shown below:

1. "SP-40": MTVLYPEYWKMY (amino acids 70-81 in SEQ ID NO:18)
2. "SP-41": KSIDNEWRKTQSMPREV (amino acids 120-136(note C->S mutation at position 131) in SEQ ID NO:18)
3. "SP-42": MSKLDVYRQVHSIIRR (amino acids 212-227 in SEQ ID NO: 18)
4. "SP-43": MFSSDAGDDSTDGFHDI (amino acids 263-279 in SEQ ID NO: 18)

EXAMPLE 27

Lymphadema Animal Model

The purpose of this experimental approach is to create an appropriate and consistent lymphedema model for testing the therapeutic effects of VEGF-2 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Experimental Procedure

Prior to beginning surgery, blood sample was drawn for protein concentration analysis. Male rats weighing approximately ~350 g are dosed with Pentobarbital. Subsequently, the right legs were shaved from knee to hip. The shaved area is swabbed with gauze soaked in 70% EtOH. Blood is drawn for serum total protein testing. Circumference and volumetric measurements were made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues. Care was taken to control any mild bleeding resulting from this procedure. After lymphatics were occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals were checked daily through the optimal edematous peak, which typically occurred by day 5-7. The plateau edematous peak was then observed. To evaluate the intensity of the lymhedema, we measured the circumference and volumes of 2 designated places on each paw before operation and daily for 7 days. The effect plasma proteins have on lymphedema and determined if protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(ChenNictor). Data is recorded by one person, while the other is dipping the limb to marked area.

Blood-plasma Protein Measurements: Blood is drawn, spun, and serum separated prior to surgery and then at conclusion for total protein and Ca2+ comparison.

Limb Weight Comparison: After drawing blood, the animal is prepared for tissue collection. The limbs were amputated using a quillitine, then both experimental and control legs were cut at the ligature and weighed. A second weighing is done as the tibio-cacaneal joint was disarticulated and the foot was weighed.

Histological Preparations: The transverse muscle located behind the knee (popliteal) area is dissected and arranged in a metal mold, filled with freezeGel, dipped into cold methylbutane, placed into labeled sample bags at −80° C. until sectioning. Upon sectioning, the muscle was observed under fluorescent microscopy for lymphatics. Other immuno/histological methods are currently being evaluated.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence at least 95% identical to a member selected from the group consisting of:
   (a) amino acids 1 to 419 of SEQ ID NO:18;
   (b) amino acids 2 to 419 of SEQ ID NO:18; and
   (c) amino acids 47 to 419 of SEQ ID NO:18;
   wherein said polypeptide promotes angiogenesis, endothelialization or vascularization.

2. The isolated polypeptide of claim 1, which is produced in a recombinant host cell.

3. An isolated polypeptide comprising:
   (a) amino acids 154-167 of SEQ ID NO:18;
   (b) 30 or more contiguous amino acids of SEQ ID NO: 18; or
   (c) 50 or more contiguous amino acids of SEQ ID NO: 18.

4. The isolated polypeptide of claim 3, which
   (a) is antigenic;
   (b) promotes angiogenesis;
   (c) promotes epithelialization; or
   (d) promotes vascularization.

5. The isolated polypeptide of claim 1, wherein the polypeptide comprises amino acid residues selected from the group consisting of:
   (a) amino acids from 154 to 167 of SEQ ID NO:18; and
   (b) Cys residues at positions 38, 80, 116, 118, 131, 173, 209 and 211 of SEQ ID NO:18.

* * * * *

SEQUENCE LISTING

<160> NUMBER OF SEQ ID NOS: 35

<210> SEQ ID NO 1
<211> LENGTH: 1674
<212> TYPE: DNA
<213> ORGANISM: Homo sapiens
<220> FEATURE:
<221> NAME/KEY: sig_peptide
<222> LOCATION: (12)..(80)
<220> FEATURE:
<221> NAME/KEY: CDS
<222> LOCATION: (12)..(1268)
<220> FEATURE:
<221> NAME/KEY: mat_peptide
<222> LOCATION: (81)..()

<400> SEQUENCE: 1

```
gtccttccac c atg cac tcg ctg ggc ttc ttc tct gtg gcg tgt tct ctg      50
            Met His Ser Leu Gly Phe Phe Ser Val Ala Cys Ser Leu
                -20                     -15 ctc gcc gct gcg ctg ctc ccg ggt cct cgc gag gcg ccc gcc gcc gcc      98
Leu Ala Ala Ala Leu Leu Pro Gly Pro Arg Glu Ala Pro Ala Ala Ala
-10              -5              -1  1               5 gcc gcc ttc gag tcc gga ctc gac ctc tcg gac gcg gag ccc gac gcg     146
Ala Ala Phe Glu Ser Gly Leu Asp Leu Ser Asp Ala Glu Pro Asp Ala
            10                  15                  20 ggc gag gcc acg gct tat gca agc aaa gat ctg gag gag cag tta cgg     194
Gly Glu Ala Thr Ala Tyr Ala Ser Lys Asp Leu Glu Glu Gln Leu Arg
        25                  30                  35 tct gtg tcc agt gta gat gaa ctc atg act gta ctc tac cca gaa tat     242
Ser Val Ser Ser Val Asp Glu Leu Met Thr Val Leu Tyr Pro Glu Tyr
    40                  45                  50 tgg aaa atg tac aag tgt cag cta agg aaa gga ggc tgg caa cat aac     290
Trp Lys Met Tyr Lys Cys Gln Leu Arg Lys Gly Gly Trp Gln His Asn
55                  60                  65                  70 aga gaa cag gcc aac ctc aac tca agg aca gaa gag act ata aaa ttt     338
Arg Glu Gln Ala Asn Leu Asn Ser Arg Thr Glu Glu Thr Ile Lys Phe
                75                  80                  85 gct gca gca cat tat aat aca gag atc ttg aaa agt att gat aat gag     386
Ala Ala Ala His Tyr Asn Thr Glu Ile Leu Lys Ser Ile Asp Asn Glu
            90                  95                  100 tgg aga aag act caa tgc atg cca cgg gag gtg tgt ata gat gtg ggg     434
Trp Arg Lys Thr Gln Cys Met Pro Arg Glu Val Cys Ile Asp Val Gly
        105                 110                 115 aag gag ttt gga gtc gcg aca aac acc ttc ttt aaa cct cca tgt gtg     482
Lys Glu Phe Gly Val Ala Thr Asn Thr Phe Phe Lys Pro Pro Cys Val
    120                 125                 130 tcc gtc tac aga tgt ggg ggt tgc tgc aat agt gag ggg ctg cag tgc     530
Ser Val Tyr Arg Cys Gly Gly Cys Cys Asn Ser Glu Gly Leu Gln Cys
135                 140                 145                 150 atg aac acc agc acg agc tac ctc agc aag acg tta ttt gaa att aca     578
Met Asn Thr Ser Thr Ser Tyr Leu Ser Lys Thr Leu Phe Glu Ile Thr
                155                 160                 165 gtg cct ctc tct caa ggc ccc aaa cca gta aca atc agt ttt gcc aat     626
Val Pro Leu Ser Gln Gly Pro Lys Pro Val Thr Ile Ser Phe Ala Asn
            170                 175                 180 cac act tcc tgc cga tgc atg tct aaa ctg gat gtt tac aga caa gtt     674
His Thr Ser Cys Arg Cys Met Ser Lys Leu Asp Val Tyr Arg Gln Val
        185                 190                 195 cat tcc att att aga cgt tcc ctg cca gca aca cta cca cag tgt cag     722
His Ser Ile Ile Arg Arg Ser Leu Pro Ala Thr Leu Pro Gln Cys Gln
```

-continued

```
                200                 205                 210
gca gcg aac aag acc tgc ccc acc aat tac atg tgg aat aat cac atc    770
Ala Ala Asn Lys Thr Cys Pro Thr Asn Tyr Met Trp Asn Asn His Ile
215                 220                 225                 230 tgc aga tgc ctg gct cag gaa gat ttt atg ttt tcc tcg gat gct gga    818
Cys Arg Cys Leu Ala Gln Glu Asp Phe Met Phe Ser Ser Asp Ala Gly
                235                 240                 245 gat gac tca aca gat gga ttc cat gac atc tgt gga cca aac aag gag    866
Asp Asp Ser Thr Asp Gly Phe His Asp Ile Cys Gly Pro Asn Lys Glu
250                 255                 260 ctg gat gaa gag acc tgt cag tgt gtc tgc aga gcg ggg ctt cgg cct    914
Leu Asp Glu Glu Thr Cys Gln Cys Val Cys Arg Ala Gly Leu Arg Pro
    265                 270                 275 gcc agc tgt gga ccc cac aaa gaa cta gac aga aac tca tgc cag tgt    962
Ala Ser Cys Gly Pro His Lys Glu Leu Asp Arg Asn Ser Cys Gln Cys
280                 285                 290 gtc tgt aaa aac aaa ctc ttc ccc agc caa tgt ggg gcc aac cga gaa   1010
Val Cys Lys Asn Lys Leu Phe Pro Ser Gln Cys Gly Ala Asn Arg Glu
295                 300                 305                 310 ttt gat gaa aac aca tgc cag tgt gta tgt aaa aga acc tgc ccc aga   1058
Phe Asp Glu Asn Thr Cys Gln Cys Val Cys Lys Arg Thr Cys Pro Arg
                315                 320                 325 aat caa ccc cta aat cct gga aaa tgt gcc tgt gaa tgt aca gaa agt   1106
Asn Gln Pro Leu Asn Pro Gly Lys Cys Ala Cys Glu Cys Thr Glu Ser
            330                 335                 340 cca cag aaa tgc ttg tta aaa gga aag aag ttc cac cac caa aca tgc   1154
Pro Gln Lys Cys Leu Leu Lys Gly Lys Lys Phe His His Gln Thr Cys
        345                 350                 355 agc tgt tac aga cgg cca tgt acg aac cgc cag aag gct tgt gag cca   1202
Ser Cys Tyr Arg Arg Pro Cys Thr Asn Arg Gln Lys Ala Cys Glu Pro
360                 365                 370 gga ttt tca tat agt gaa gaa gtg tgt cgt tgt gtc cct tca tat tgg   1250
Gly Phe Ser Tyr Ser Glu Glu Val Cys Arg Cys Val Pro Ser Tyr Trp
375                 380                 385                 390 caa aga cca caa atg agc taagattgta ctgttttcca gttcatcgat          1298
Gln Arg Pro Gln Met Ser
                395 tttctattat ggaaaactgt gttgccacag tagaactgtc tgtgaacaga gagacccttg  1358 tgggtccatg ctaacaaaga caaaagtctg tctttcctga accatgtgga taactttaca  1418 gaaatggact ggagctcatc tgcaaaaggc ctcttgtaaa gactggtttt ctgccaatga  1478 ccaaacagcc aagattttcc tcttgtgatt tctttaaaag aatgactata taatttattt  1538 ccactaaaaa tattgtttct gcattcattt ttatagcaac aacaattggt aaaactcact  1598 gtgatcaata ttttatatc atgcaaaata tgtttaaaat aaaatgaaaa ttgtatttat  1658 aaaaaaaaaa aaaaaa                                                 1674

<210> SEQ ID NO 2
<211> LENGTH: 419
<212> TYPE: PRT
<213> ORGANISM: Homo sapiens

<400> SEQUENCE: 2

Met His Ser Leu Gly Phe Phe Ser Val Ala Cys Ser Leu Leu Ala Ala
                -20                 -15                 -10

Ala Leu Leu Pro Gly Pro Arg Glu Ala Pro Ala Ala Ala Ala Phe
        -5                  -1 1                 5

Glu Ser Gly Leu Asp Leu Ser Asp Ala Glu Pro Asp Ala Gly Glu Ala
```

```
            10                  15                  20                  25
    Thr Ala Tyr Ala Ser Lys Asp Leu Glu Glu Gln Leu Arg Ser Val Ser
                    30                  35                  40

Ser Val Asp Glu Leu Met Thr Val Leu Tyr Pro Glu Tyr Trp Lys Met
                    45                  50                  55

Tyr Lys Cys Gln Leu Arg Lys Gly Gly Trp Gln His Asn Arg Glu Gln
                    60                  65                  70

Ala Asn Leu Asn Ser Arg Thr Glu Glu Thr Ile Lys Phe Ala Ala Ala
                75                  80                  85

His Tyr Asn Thr Glu Ile Leu Lys Ser Ile Asp Asn Glu Trp Arg Lys
     90                  95                 100                 105

Thr Gln Cys Met Pro Arg Glu Val Cys Ile Asp Val Gly Lys Glu Phe
                        110                 115                 120

Gly Val Ala Thr Asn Thr Phe Phe Lys Pro Cys Val Ser Val Tyr
                    125                 130                 135

Arg Cys Gly Gly Cys Cys Asn Ser Glu Gly Leu Gln Cys Met Asn Thr
                    140                 145                 150

Ser Thr Ser Tyr Leu Ser Lys Thr Leu Phe Glu Ile Thr Val Pro Leu
                    155                 160                 165

Ser Gln Gly Pro Lys Pro Val Thr Ile Ser Phe Ala Asn His Thr Ser
    170                 175                 180                 185

Cys Arg Cys Met Ser Lys Leu Asp Val Tyr Arg Gln Val His Ser Ile
                        190                 195                 200

Ile Arg Arg Ser Leu Pro Ala Thr Leu Pro Gln Cys Gln Ala Ala Asn
                    205                 210                 215

Lys Thr Cys Pro Thr Asn Tyr Met Trp Asn Asn His Ile Cys Arg Cys
                    220                 225                 230

Leu Ala Gln Glu Asp Phe Met Phe Ser Ser Asp Ala Gly Asp Asp Ser
                    235                 240                 245

Thr Asp Gly Phe His Asp Ile Cys Gly Pro Asn Lys Glu Leu Asp Glu
    250                 255                 260                 265

Glu Thr Cys Gln Cys Val Cys Arg Ala Gly Leu Arg Pro Ala Ser Cys
                        270                 275                 280

Gly Pro His Lys Glu Leu Asp Arg Asn Ser Cys Gln Cys Val Cys Lys
                    285                 290                 295

Asn Lys Leu Phe Pro Ser Gln Cys Gly Ala Asn Arg Glu Phe Asp Glu
                    300                 305                 310

Asn Thr Cys Gln Cys Val Cys Lys Arg Thr Cys Pro Arg Asn Gln Pro
                    315                 320                 325

Leu Asn Pro Gly Lys Cys Ala Cys Glu Cys Thr Glu Ser Pro Gln Lys
    330                 335                 340                 345

Cys Leu Leu Lys Gly Lys Lys Phe His His Gln Thr Cys Ser Cys Tyr
                    350                 355                 360

Arg Arg Pro Cys Thr Asn Arg Gln Lys Ala Cys Glu Pro Gly Phe Ser
                    365                 370                 375

Tyr Ser Glu Glu Val Cys Arg Cys Val Pro Ser Tyr Trp Gln Arg Pro
                    380                 385                 390

Gln Met Ser
        395

<210> SEQ ID NO 3
<211> LENGTH: 1525
<212> TYPE: DNA
<213> ORGANISM: Homo sapiens
```

```
<220> FEATURE:
<221> NAME/KEY: sig_peptide
<222> LOCATION: (71)..(142)
<220> FEATURE:
<221> NAME/KEY: CDS
<222> LOCATION: (71)..(1120)
<220> FEATURE:
<221> NAME/KEY: mat_peptide
<222> LOCATION: (143)..()

<400> SEQUENCE: 3
cgaggccacg gcttatgcaa gcaaagatct ggaggagcag ttacggtctg tgtccagtgt      60
agatgaactc atg act gta ctc tac cca gaa tat tgg aaa atg tac aag        109
            Met Thr Val Leu Tyr Pro Glu Tyr Trp Lys Met Tyr Lys
                    -20                 -15 tgt cag cta agg aaa gga ggc tgg caa cat aac aga gaa cag gcc aac       157
Cys Gln Leu Arg Lys Gly Gly Trp Gln His Asn Arg Glu Gln Ala Asn
        -10                 -5                  -1   1               5 ctc aac tca agg aca gaa gag act ata aaa ttt gct gca gca cat tat       205
Leu Asn Ser Arg Thr Glu Glu Thr Ile Lys Phe Ala Ala Ala His Tyr
                10                  15                  20 aat aca gag atc ttg aaa agt att gat aat gag tgg aga aag act caa       253
Asn Thr Glu Ile Leu Lys Ser Ile Asp Asn Glu Trp Arg Lys Thr Gln
            25                  30                  35 tgc atg cca cgg gag gtg tgt ata gat gtg ggg aag gag ttt gga gtc       301
Cys Met Pro Arg Glu Val Cys Ile Asp Val Gly Lys Glu Phe Gly Val
        40                  45                  50 gcg aca aac acc ttc ttt aaa cct cca tgt gtg tcc gtc tac aga tgt       349
Ala Thr Asn Thr Phe Phe Lys Pro Pro Cys Val Ser Val Tyr Arg Cys
    55                  60                  65 ggg ggt tgc tgc aat agt gag ggg ctg cag tgc atg aac acc agc acg       397
Gly Gly Cys Cys Asn Ser Glu Gly Leu Gln Cys Met Asn Thr Ser Thr
70                  75                  80                  85 agc tac ctc agc aag acg tta ttt gaa att aca gtg cct ctc tct caa       445
Ser Tyr Leu Ser Lys Thr Leu Phe Glu Ile Thr Val Pro Leu Ser Gln
                90                  95                  100 ggc ccc aaa cca gta aca atc agt ttt gcc aat cac act tcc tgc cga       493
Gly Pro Lys Pro Val Thr Ile Ser Phe Ala Asn His Thr Ser Cys Arg
            105                 110                 115 tgc atg tct aaa ctg gat gtt tac aga caa gtt cat tcc att att aga       541
Cys Met Ser Lys Leu Asp Val Tyr Arg Gln Val His Ser Ile Ile Arg
        120                 125                 130 cgt tcc ctg cca gca aca cta cca cag tgt cag gca gcg aac aag acc       589
Arg Ser Leu Pro Ala Thr Leu Pro Gln Cys Gln Ala Ala Asn Lys Thr
    135                 140                 145 tgc ccc acc aat tac atg tgg aat aat cac atc tgc aga tgc ctg gct       637
Cys Pro Thr Asn Tyr Met Trp Asn Asn His Ile Cys Arg Cys Leu Ala
150                 155                 160                 165 cag gaa gat ttt atg ttt tcc tcg gat gct gga gat gac tca aca gat       685
Gln Glu Asp Phe Met Phe Ser Ser Asp Ala Gly Asp Asp Ser Thr Asp
                170                 175                 180 gga ttc cat gac atc tgt gga cca aac aag gag ctg gat gaa gag acc       733
Gly Phe His Asp Ile Cys Gly Pro Asn Lys Glu Leu Asp Glu Glu Thr
            185                 190                 195 tgt cag tgt gtc tgc aga gcg ggg ctt cgg cct gcc agc tgt gga ccc       781
Cys Gln Cys Val Cys Arg Ala Gly Leu Arg Pro Ala Ser Cys Gly Pro
        200                 205                 210 cac aaa gaa cta gac aga aac tca tgc cag tgt gtc tgt aaa aac aaa       829
His Lys Glu Leu Asp Arg Asn Ser Cys Gln Cys Val Cys Lys Asn Lys
    215                 220                 225 ctc ttc ccc agc caa tgt ggg gcc aac cga gaa ttt gat gaa aac aca       877
```

-continued

```
Leu Phe Pro Ser Gln Cys Gly Ala Asn Arg Glu Phe Asp Glu Asn Thr
230                 235                 240                 245 tgc cag tgt gta tgt aaa aga acc tgc ccc aga aat caa ccc cta aat      925
Cys Gln Cys Val Cys Lys Arg Thr Cys Pro Arg Asn Gln Pro Leu Asn
                250                 255                 260 cct gga aaa tgt gcc tgt gaa tgt aca gaa agt cca cag aaa tgc ttg      973
Pro Gly Lys Cys Ala Cys Glu Cys Thr Glu Ser Pro Gln Lys Cys Leu
            265                 270                 275 tta aaa gga aag aag ttc cac cac caa aca tgc agc tgt tac aga cgg     1021
Leu Lys Gly Lys Lys Phe His His Gln Thr Cys Ser Cys Tyr Arg Arg
        280                 285                 290 cca tgt acg aac cgc cag aag gct tgt gag cca gga ttt tca tat agt     1069
Pro Cys Thr Asn Arg Gln Lys Ala Cys Glu Pro Gly Phe Ser Tyr Ser
    295                 300                 305 gaa gaa gtg tgt cgt tgt gtc cct tca tat tgg caa aga cca caa atg     1117
Glu Glu Val Cys Arg Cys Val Pro Ser Tyr Trp Gln Arg Pro Gln Met
310                 315                 320                 325 agc taagattgta ctgttttcca gttcatcgat tttctattat ggaaaactgt          1170
Ser gttgccacag tagaactgtc tgtgaacaga gagaccttg tgggtccatg ctaacaaga     1230 caaaagtctg tctttcctga accatgtgga taactttaca gaaatggact ggagctcatc  1290 tgcaaaggc ctcttgtaaa gactggtttt ctgccaatga ccaaacagcc aagattttcc   1350
tcttgtgatt tctttaaaag aatgactata taatttattt ccactaaaaa tattgtttct  1410
gcattcattt ttatagcaac aacaattggt aaaactcact gtgatcaata tttttatatc  1470
atgcaaaata tgtttaaaat aaaatgaaaa ttgtattata aaaaaaaaaa aaaaa        1525

<210> SEQ ID NO 4
<211> LENGTH: 350
<212> TYPE: PRT
<213> ORGANISM: Homo sapiens

<400> SEQUENCE: 4

Met Thr Val Leu Tyr Pro Glu Tyr Trp Lys Met Tyr Lys Cys Gln Leu
                -20                 -15                 -10

Arg Lys Gly Gly Trp Gln His Asn Arg Glu Gln Ala Asn Leu Asn Ser
        -5                  -1  1                   5

Arg Thr Glu Glu Thr Ile Lys Phe Ala Ala His Tyr Asn Thr Glu
    10                  15                  20

Ile Leu Lys Ser Ile Asp Asn Glu Trp Arg Lys Thr Gln Cys Met Pro
25                  30                  35                  40

Arg Glu Val Cys Ile Asp Val Gly Lys Glu Phe Gly Val Ala Thr Asn
                45                  50                  55

Thr Phe Phe Lys Pro Pro Cys Val Ser Val Tyr Arg Cys Gly Gly Cys
            60                  65                  70

Cys Asn Ser Glu Gly Leu Gln Cys Met Asn Thr Ser Thr Ser Tyr Leu
        75                  80                  85

Ser Lys Thr Leu Phe Glu Ile Thr Val Pro Leu Ser Gln Gly Pro Lys
    90                  95                  100

Pro Val Thr Ile Ser Phe Ala Asn His Thr Ser Cys Arg Cys Met Ser
105                 110                 115                 120

Lys Leu Asp Val Tyr Arg Gln Val His Ser Ile Ile Arg Arg Ser Leu
                125                 130                 135

Pro Ala Thr Leu Pro Gln Cys Gln Ala Ala Asn Lys Thr Cys Pro Thr
            140                 145                 150
```

```
Asn Tyr Met Trp Asn Asn His Ile Cys Arg Cys Leu Ala Gln Glu Asp
        155                 160                 165

Phe Met Phe Ser Ser Asp Ala Gly Asp Asp Ser Thr Asp Gly Phe His
    170                 175                 180

Asp Ile Cys Gly Pro Asn Lys Glu Leu Asp Glu Thr Cys Gln Cys
185                 190                 195                 200

Val Cys Arg Ala Gly Leu Arg Pro Ala Ser Cys Gly Pro His Lys Glu
                205                 210                 215

Leu Asp Arg Asn Ser Cys Gln Cys Val Cys Lys Asn Lys Leu Phe Pro
                220                 225                 230

Ser Gln Cys Gly Ala Asn Arg Glu Phe Asp Glu Asn Thr Cys Gln Cys
            235                 240                 245

Val Cys Lys Arg Thr Cys Pro Arg Asn Gln Pro Leu Asn Pro Gly Lys
        250                 255                 260

Cys Ala Cys Glu Cys Thr Glu Ser Pro Gln Lys Cys Leu Leu Lys Gly
265                 270                 275                 280

Lys Lys Phe His His Gln Thr Cys Ser Cys Tyr Arg Arg Pro Cys Thr
                285                 290                 295

Asn Arg Gln Lys Ala Cys Glu Pro Gly Phe Ser Tyr Ser Glu Glu Val
            300                 305                 310

Cys Arg Cys Val Pro Ser Tyr Trp Gln Arg Pro Gln Met Ser
        315                 320                 325

<210> SEQ ID NO 5
<211> LENGTH: 196
<212> TYPE: PRT
<213> ORGANISM: Homo sapiens

<400> SEQUENCE: 5

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
195
```

<210> SEQ ID NO 6
<211> LENGTH: 241
<212> TYPE: PRT
<213> ORGANISM: Homo sapiens

<400> SEQUENCE: 6

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 7
<211> LENGTH: 232
<212> TYPE: PRT
<213> ORGANISM: Homo sapiens

<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

```
Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 8
<211> LENGTH: 14
<212> TYPE: PRT
<213> ORGANISM: Homo sapiens
<220> FEATURE:
<221> NAME/KEY: SITE
<222> LOCATION: (2)..(2)
<223> OTHER INFORMATION: X is equal to any of the naturally occurring
      amino acids
<220> FEATURE:
<221> NAME/KEY: SITE
<222> LOCATION: (5)..(5)
<223> OTHER INFORMATION: X is equal to any of the naturally occurring
      amino acids
<220> FEATURE:
<221> NAME/KEY: SITE
<222> LOCATION: (6)..(6)
<223> OTHER INFORMATION: X is equal to any of the naturally occurring
      amino acids
<220> FEATURE:
<221> NAME/KEY: SITE
<222> LOCATION: (7)..(7)
<223> OTHER INFORMATION: X is equal to any of the naturally occurring
      amino acids
<220> FEATURE:
<221> NAME/KEY: SITE
<222> LOCATION: (10)..(10)
<223> OTHER INFORMATION: X is equal to any of the naturally occurring
      amino acids

<400> SEQUENCE: 8

Pro Xaa Cys Val Xaa Xaa Xaa Arg Cys Xaa Gly Cys Cys Asn
1               5                   10

<210> SEQ ID NO 9
<211> LENGTH: 18
<212> TYPE: DNA
<213> ORGANISM: Artificial sequence
<220> FEATURE:
<221> NAME/KEY: primer_bind
<222> LOCATION: (1)..(18)
<223> OTHER INFORMATION: 5' PCR oligonucleotide primer

<400> SEQUENCE: 9
atgcttccgg ctcgtatg                                                    18
```

<210> SEQ ID NO 10
<211> LENGTH: 19
<212> TYPE: DNA
<213> ORGANISM: Artificial sequence
<220> FEATURE:
<221> NAME/KEY: primer_bind
<222> LOCATION: (1)..(19)
<223> OTHER INFORMATION: M13-2 forward primer

<400> SEQUENCE: 10
gggttttccc agtcacgac                                              19

<210> SEQ ID NO 11
<211> LENGTH: 21
<212> TYPE: DNA
<213> ORGANISM: Artificial sequence
<220> FEATURE:
<221> NAME/KEY: primer_bind
<222> LOCATION: (1)..(21)
<223> OTHER INFORMATION: VEGF primer F4

<400> SEQUENCE: 11
ccacatggtt caggaaagac a                                           21

<210> SEQ ID NO 12
<211> LENGTH: 50
<212> TYPE: DNA
<213> ORGANISM: Artificial sequence
<220> FEATURE:
<221> NAME/KEY: primer_bind
<222> LOCATION: (1)..(50)
<223> OTHER INFORMATION: 5' PCR oligonucleotide primer

<400> SEQUENCE: 12
tgtaatacga ctcactatag ggatcccgcc atggaggcca cggcttatgc            50

<210> SEQ ID NO 13
<211> LENGTH: 28
<212> TYPE: DNA
<213> ORGANISM: Artificial sequence
<220> FEATURE:
<221> NAME/KEY: primer_bind
<222> LOCATION: (1)..(28)
<223> OTHER INFORMATION: 3' PCR oligonucleotide primer

<400> SEQUENCE: 13
gatctctaga ttagctcatt tgtggtct                                    28

<210> SEQ ID NO 14
<211> LENGTH: 27
<212> TYPE: DNA
<213> ORGANISM: Artificial sequence
<220> FEATURE:
<221> NAME/KEY: primer_bind
<222> LOCATION: (1)..(27)
<223> OTHER INFORMATION: 5' PCR primer

<400> SEQUENCE: 14
cgcggatcca tgactgtact ctaccca                                     27

<210> SEQ ID NO 15
<211> LENGTH: 60
<212> TYPE: DNA
<213> ORGANISM: Artificial sequence
<220> FEATURE:
<221> NAME/KEY: primer_bind
<222> LOCATION: (1)..(60)

-continued

<223> OTHER INFORMATION: 3' PCR primer

<400> SEQUENCE: 15
cgctctagat caagcgtagt ctgggacgtc gtatgggtac tcgaggctca tttgtggtct    60

<210> SEQ ID NO 16
<211> LENGTH: 3974
<212> TYPE: DNA
<213> ORGANISM: Escherichia coli

<400> SEQUENCE: 16
ggtacctaag tgagtagggc gtccgatcga cggacgcctt tttttgaat tcgtaatcat    60 ggtcatagct gtttcctgtg tgaaattgtt atccgctcac aattccacac aacatacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900
gaagaacagt atttggtatc tgcgctctgc tgaagccagt taccttcgga aaaagagttg   960
gtagctcttg atccggcaaa caaaccaccg ctggtagcgg tggttttttt gtttgcaagc  1020
agcagattac gcgcagaaaa aaaggatctc aagaagatcc tttgatcttt tctacggggt  1080
ctgacgctca gtggaacgaa aactcacgtt aagggatttt ggtcatgaga ttatcgtcga  1140
caattcgcgc gcgaaggcga agcggcatgc atttacgttg acaccatcga atggtgcaaa  1200
acctttcgcg gtatggcatg atagcgcccg gaagagagtc aattcagggt ggtgaatgtg  1260
aaaccagtaa cgttatacga tgtcgcagag tatgccggtg tctcttatca gaccgtttcc  1320
cgcgtggtga accaggccag ccacgtttct gcgaaaacgc gggaaaaagt ggaagcggcg  1380
atggcggagc tgaattacat tcccaaccgc gtggcacaac aactggcggg caaacagtcg  1440
ttgctgattg gcgttgccac ctccagtctg gccctgcacg cgccgtcgca aattgtcgcg  1500
gcgattaaat ctcgcgccga tcaactgggt gccagcgtgg tggtgtcgat ggtagaacga  1560
agcggcgtcg aagcctgtaa agcggcggtg cacaatcttc tcgcgcaacg cgtcagtggg  1620
ctgatcatta actatccgct ggatgaccag gatgccattg ctgtggaagc tgcctgcact  1680
aatgttccgg cgttatttct tgatgtctct gaccagacac ccatcaacag tattatttc   1740 tcccatgaag acggtacgcg actgggcgtg gagcatctgg tcgcattggg tcaccagcaa  1800
atcgcgctgt tagcgggccc attaagttct gtctcggcgc gtctgcgtct ggctggctgg  1860
cataaatatc tcactcgcaa tcaaattcag ccgatagcgg aacgggaagg cgactggagt  1920
gccatgtccg gttttcaaca aaccatgcaa atgctgaatg agggcatcgt tcccactgcg  1980

-continued

```
atgctggttg ccaacgatca gatggcgctg ggcgcaatgc gcgccattac cgagtccggg    2040
ctgcgcgttg gtgcggatat ctcggtagtg ggatacgacg ataccgaaga cagctcatgt    2100
tatatcccgc cgttaaccac catcaaacag gattttcgcc tgctgggca aaccagcgtg     2160 gaccgcttgc tgcaactctc tcagggccag gcggtgaagg gcaatcagct gttgcccgtc    2220
tcactggtga aaagaaaaac caccctggcg cccaatacgc aaaccgcctc tccccgcgcg    2280
ttggccgatt cattaatgca gctggcacga caggtttccc gactggaaag cgggcagtga    2340
gcgcaacgca attaatgtaa gttagcgcga attgtcgacc aaagcggcca tcgtgcctcc    2400
ccactcctgc agttcggggg catggatgcg cggatagccg ctgctggttt cctggatgcc    2460
gacggatttg cactgccggt agaactccgc gaggtcgtcc agcctcaggc agcagctgaa    2520
ccaactcgcg aggggatcga gcccggggtg ggcgaagaac tccagcatga gatccccgcg    2580
ctggaggatc atccagccgg cgtcccggaa aacgattccg aagcccaacc tttcatagaa    2640
ggcggcggtg gaatcgaaat ctcgtgatgg caggttgggc gtcgcttggt cggtcatttc    2700
gaacccagga gtcccgctca gaagaactcg tcaagaaggc gatagaaggc gatgcgctgc    2760
gaatcgggag cggcgatacc gtaaagcacg aggaagcggt cagcccattc gccgccaagc    2820
tcttcagcaa tatcacgggt agccaacgct atgtcctgat agcggtccgc cacacccagc    2880
cggccacagt cgatgaatcc agaaaagcgg ccattttcca ccatgatatt cggcaagcag    2940
gcatcgccat gggtcacgac gagatcctcg ccgtcgggca tgcgcgcctt gagcctggcg    3000
aacagttcgg ctggcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aaagaaccgg gcgcccctgc gctgacagcc ggaacacggc ggcatcagag    3420
cagccgattg tctgttgtgc ccagtcatag ccgaatagcc tctccaccca gcggccgga    3480 gaacctgcgt gcaatccatc ttgttcaatc atgcgaaacg atcctcatcc tgtctcttga    3540
tcagatcttg atccctgcg ccatcagatc cttggcggca agaaagccat ccagtttact    3600
ttgcagggct tcccaacctt accagagggc gccccagctg gcaattccgg ttcgcttgct    3660
gtccataaaa ccgcccagtc tagctatcgc catgtaagcc cactgcaagc tacctgcttt    3720
ctctttgcgc ttgcgttttc ccttgtccag atagcccagt agctgacatt catccggggt    3780
cagcaccgtt tctgcggact ggctttctac gtgttccgct tcctttagca gcccttgcgc    3840
cctgagtgct tgcggcagcg tgaagcttaa aaaactgcaa aaatagttt gacttgtgag    3900 cggataacaa ttaagatgta cccaattgtg agcggataac aatttcacac attaaagagg    3960
agaaattaca tatg                                                      3974
```

```
<210> SEQ ID NO 17
<211> LENGTH: 112
<212> TYPE: DNA
<213> ORGANISM: Artificial sequence
<220> FEATURE:
<221> NAME/KEY: promoter
<222> LOCATION: (1)..(112)
<223> OTHER INFORMATION: pHE4a promoter
```

<400> SEQUENCE: 17
aagcttaaaa aactgcaaaa aatagtttga cttgtgagcg ataacaatt aagatgtacc    60 caattgtgag cggataacaa tttcacacat taaagaggag aaattacata tg    112

<210> SEQ ID NO 18
<211> LENGTH: 419
<212> TYPE: PRT
<213> ORGANISM: Homo sapiens

<400> SEQUENCE: 18

```
Met His Ser Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350
```

```
Leu Asn Pro Gly Lys Cys Ala Cys Glu Cys Thr Glu Ser Pro Gln Lys
        355                 360                 365
Cys Leu Leu Lys Gly Lys Lys Phe His His Gln Thr Cys Ser Cys Tyr
        370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Gln Arg Pro
                405                 410                 415
Gln Met Ser
```

<210> SEQ ID NO 19
<211> LENGTH: 30
<212> TYPE: DNA
<213> ORGANISM: Artificial sequence
<220> FEATURE:
<221> NAME/KEY: primer_bind
<222> LOCATION: (1)..(30)
<223> OTHER INFORMATION: 5' PCR primer

<400> SEQUENCE: 19
gcagcacata tgacagaaga gactataaaa                                    30

<210> SEQ ID NO 20
<211> LENGTH: 30
<212> TYPE: DNA
<213> ORGANISM: Artificial sequence
<220> FEATURE:
<221> NAME/KEY: primer_bind
<222> LOCATION: (1)..(30)
<223> OTHER INFORMATION: 3' PCR primer

<400> SEQUENCE: 20
gcagcaggta cctcacagtt tagacatgca                                    30

<210> SEQ ID NO 21
<211> LENGTH: 30
<212> TYPE: DNA
<213> ORGANISM: Artificial sequence
<220> FEATURE:
<221> NAME/KEY: primer_bind
<222> LOCATION: (1)..(30)
<223> OTHER INFORMATION: 3' PCR primer

<400> SEQUENCE: 21
gcagcaggta cctcaacgtc taataatgga                                    30

<210> SEQ ID NO 22
<211> LENGTH: 30
<212> TYPE: DNA
<213> ORGANISM: Artificial sequence
<220> FEATURE:
<221> NAME/KEY: primer_bind
<222> LOCATION: (1)..(30)
<223> OTHER INFORMATION: 5' PCR primer

<400> SEQUENCE: 22
gcagcaggat cccacagaag agactataaa                                    30

<210> SEQ ID NO 23
<211> LENGTH: 30
<212> TYPE: DNA
<213> ORGANISM: Artificial sequence
<220> FEATURE:
<221> NAME/KEY: primer_bind
<222> LOCATION: (1)..(30)

<223> OTHER INFORMATION: 3' PCR primer

<400> SEQUENCE: 23
gcagcatcta gatcacagtt tagacatgca    30

<210> SEQ ID NO 24
<211> LENGTH: 39
<212> TYPE: DNA
<213> ORGANISM: Artificial sequence
<220> FEATURE:
<221> NAME/KEY: primer_bind
<222> LOCATION: (1)..(39)
<223> OTHER INFORMATION: 5' PCR primer

<400> SEQUENCE: 24
gcagcaggat cccacagaag agactataaa atttgctgc    39

<210> SEQ ID NO 25
<211> LENGTH: 36
<212> TYPE: DNA
<213> ORGANISM: Artificial sequence
<220> FEATURE:
<221> NAME/KEY: primer_bind
<222> LOCATION: (1)..(36)
<223> OTHER INFORMATION: 5' PCR primer

<400> SEQUENCE: 25
gcagcatcta gatcaacgtc taataatgga atgaac    36

<210> SEQ ID NO 26
<211> LENGTH: 55
<212> TYPE: DNA
<213> ORGANISM: Artificial sequence
<220> FEATURE:
<221> NAME/KEY: primer_bind
<222> LOCATION: (1)..(55)
<223> OTHER INFORMATION: 5' PCR primer

<400> SEQUENCE: 26
gatcgatcca tcatgcactc gctgggcttc ttctctgtgg cgtgttctct gctcg    55

<210> SEQ ID NO 27
<211> LENGTH: 39
<212> TYPE: DNA
<213> ORGANISM: Artificial sequence
<220> FEATURE:
<221> NAME/KEY: primer_bind
<222> LOCATION: (1)..(39)
<223> OTHER INFORMATION: 3' PCR primer

<400> SEQUENCE: 27
gcagggtacg gatcctagat tagctcattt gtggtcttt    39

<210> SEQ ID NO 28
<211> LENGTH: 39
<212> TYPE: DNA
<213> ORGANISM: Artificial sequence
<220> FEATURE:
<221> NAME/KEY: primer_bind
<222> LOCATION: (1)..(39)
<223> OTHER INFORMATION: 5' PCR primer

<400> SEQUENCE: 28
gactggatcc gccaccatgc actcgctggg cttcttctc    39

<210> SEQ ID NO 29
<211> LENGTH: 35

<212> TYPE: DNA
<213> ORGANISM: Artificial sequence
<220> FEATURE:
<221> NAME/KEY: primer_bind
<222> LOCATION: (1)..(35)
<223> OTHER INFORMATION: 3' PCR primer

<400> SEQUENCE: 29
gactggtacc ttatcacata aaatcttcct gagcc        35

<210> SEQ ID NO 30
<211> LENGTH: 39
<212> TYPE: DNA
<213> ORGANISM: Artificial sequence
<220> FEATURE:
<221> NAME/KEY: primer_bind
<222> LOCATION: (1)..(39)
<223> OTHER INFORMATION: 5' PCR primer

<400> SEQUENCE: 30
gactggatcc gccaccatgc actcgctggg cttcttctc        39

<210> SEQ ID NO 31
<211> LENGTH: 34
<212> TYPE: DNA
<213> ORGANISM: Artificial sequence
<220> FEATURE:
<221> NAME/KEY: primer_bind
<222> LOCATION: (1)..(34)
<223> OTHER INFORMATION: 3' PCR primer

<400> SEQUENCE: 31
gactggtacc ttatcagtct agttctttgt gggg        34

<210> SEQ ID NO 32
<211> LENGTH: 39
<212> TYPE: DNA
<213> ORGANISM: Artificial sequence
<220> FEATURE:
<221> NAME/KEY: primer_bind
<222> LOCATION: (1)..(39)
<223> OTHER INFORMATION: 5' PCR primer

<400> SEQUENCE: 32
gactggatcc gccaccatgc actcgctggg cttcttctc        39

<210> SEQ ID NO 33
<211> LENGTH: 37
<212> TYPE: DNA
<213> ORGANISM: Artificial sequence
<220> FEATURE:
<221> NAME/KEY: primer_bind
<222> LOCATION: (1)..(37)
<223> OTHER INFORMATION: 3' PCR primer

<400> SEQUENCE: 33
gactggtacc tcattactgt ggactttctg tacattc        37

<210> SEQ ID NO 34
<211> LENGTH: 38
<212> TYPE: DNA
<213> ORGANISM: Artificial sequence
<220> FEATURE:
<221> NAME/KEY: primer_bind

```
<222> LOCATION: (1)..(38)
<223> OTHER INFORMATION: 5' PCR primer

<400> SEQUENCE: 34
gcagcaggat ccacagaaga gactataaaa tttgctgc                              38

<210> SEQ ID NO 35
<211> LENGTH: 37
<212> TYPE: DNA
<213> ORGANISM: Artificial sequence
<220> FEATURE:
<221> NAME/KEY: primer_bind
<222> LOCATION: (1)..(37)
<223> OTHER INFORMATION: 3' PCR primer

<400> SEQUENCE: 35
cgtcgttcta gatcacagtt tagacatgca tcggcag                               37
```